(12) United States Patent
Jones et al.

(10) Patent No.: US 9,663,504 B2
(45) Date of Patent: *May 30, 2017

(54) SALTS OF HETEROCYCLIC MODULATORS OF HIF ACTIVITY FOR TREATMENT OF DISEASE

(71) Applicant: Board of Regents, University of Texas System, Austin, TX (US)

(72) Inventors: Philip Jones, Houston, TX (US); Maria Emilia Di Francesco, Houston, TX (US); Timothy McAfoos, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/631,454

(22) Filed: Feb. 25, 2015

(65) Prior Publication Data

US 2015/0239876 A1 Aug. 27, 2015

Related U.S. Application Data

(60) Provisional application No. 61/944,345, filed on Feb. 25, 2014.

(51) Int. Cl.
*C07D 413/14* (2006.01)

(52) U.S. Cl.
CPC .................. *C07D 413/14* (2013.01)

(58) Field of Classification Search
CPC .. C07D 405/14; C07D 513/04; C07D 413/04; C07D 417/14; C07D 417/04; C07D 413/14; C07D 471/04

USPC ........................................... 546/209; 514/326
See application file for complete search history.

(56) References Cited

U.S. PATENT DOCUMENTS

| 6,300,344 | B1 | 10/2001 | Taniguchi et al. |
|---|---|---|---|
| 8,470,811 | B2 * | 6/2013 | Harter ............... C07D 413/14 514/210.2 |
| 9,018,380 | B2 | 4/2015 | Jones et al. |
| 9,115,120 | B2 | 8/2015 | Jones et al. |
| 2004/0058964 | A1 | 3/2004 | Devadas et al. |
| 2006/0269942 | A1 | 11/2006 | Kolb et al. |
| 2007/0105900 | A1 | 5/2007 | Berdini et al. |
| 2010/0063104 | A1 | 3/2010 | Nakai et al. |

(Continued)

FOREIGN PATENT DOCUMENTS

| EP | 2768826 A1 | 8/2014 |
|---|---|---|
| WO | WO9703973 A1 | 2/1997 |

(Continued)

OTHER PUBLICATIONS

U.S. Appl. No. 14/800,307, filed Jul. 15, 2015, Jones, Philip et al.

(Continued)

*Primary Examiner* — Noble Jarrell
*Assistant Examiner* — Daniel Carcanague
(74) *Attorney, Agent, or Firm* — Dennis A. Bennett; Cynthia Hathaway

(57) ABSTRACT

The present disclosure relates to salts of heterocyclic compounds and methods that inhibit HIF pathway activity. The compounds are designed to treat or prevent cancer and other hypoxia-mediated diseases.

30 Claims, 16 Drawing Sheets

(56) References Cited

U.S. PATENT DOCUMENTS

| | | | | |
|---|---|---|---|---|
| 2010/0249085 | A1* | 9/2010 | Boyer | C07D 403/04 |
| | | | | 514/210.2 |
| 2011/0301122 | A1 | 12/2011 | Häerter et al. | |
| 2011/0312930 | A1 | 12/2011 | Häerter et al. | |
| 2012/0028950 | A1 | 2/2012 | Häerter et al. | |
| 2013/0196964 | A1* | 8/2013 | Harter | C07D 413/04 |
| | | | | 514/210.18 |
| 2014/0057914 | A1* | 2/2014 | Jones | C07D 417/14 |
| | | | | 514/236.2 |
| 2014/0066424 | A1* | 3/2014 | Jones | C07D 413/04 |
| | | | | 514/210.18 |
| 2014/0073634 | A1 | 3/2014 | Jones et al. | |
| 2014/0329797 | A1 | 11/2014 | Härter et al. | |
| 2015/0252058 | A1* | 9/2015 | Jones | C07D 413/04 |
| | | | | 514/210.18 |

FOREIGN PATENT DOCUMENTS

| | | |
|---|---|---|
| WO | WO0016760 A2 | 3/2000 |
| WO | WO0027394 A1 | 5/2000 |
| WO | WO03068230 A1 | 8/2003 |
| WO | WO2005002576 A2 | 1/2005 |
| WO | WO2005018557 A2 | 3/2005 |
| WO | WO2006070198 A1 | 7/2006 |
| WO | WO2006116736 A2 | 11/2006 |
| WO | WO2008145243 A2 | 4/2008 |
| WO | WO2008005457 A2 | 10/2008 |
| WO | WO2008141731 A2 | 11/2008 |
| WO | WO2010039248 A1 | 4/2010 |
| WO | WO2010054762 A1 | 5/2010 |
| WO | WO2010054763 A1 | 5/2010 |
| WO | WO2010054764 A1 | 5/2010 |
| WO | WO2011141325 A1 | 11/2011 |
| WO | WO2011141326 A1 | 11/2011 |
| WO | WO2013057101 A1 | 4/2013 |
| WO | WO2014031928 A1 | 2/2014 |
| WO | WO2014031933 A2 | 2/2014 |
| WO | WO2014031936 A2 | 2/2014 |
| WO | WO2014031928 A3 | 4/2014 |
| WO | WO2014031933 A3 | 4/2014 |
| WO | WO2014031936 A3 | 4/2014 |
| WO | WO2015130790 A2 | 9/2015 |
| WO | WO2015130790 A3 | 12/2015 |

OTHER PUBLICATIONS

Jones, Philip et al., Heterocyclic modulators of HIF activity for treatment of disease, Univ. Texas MD Anderson Cancer Center Institute, U.S. Pat. No. 9,018,380, Corrected Notice of Allowance, Mar. 3, 2015.

Jones, Philip et al., Heterocyclic modulators of HIF activity for treatment of disease, Univ. Texas MD Anderson Cancer Center Institute, U.S. Pat. No. 9,018,380, Notice of Allowance, Jan. 9, 2015.

Jones, Philip et al., Heterocyclic modulators of HIF activity for treatment of disease, Univ. Texas MD Anderson Cancer Center Institute, U.S. Pat. No. 9,115,120, Notice of Allowance, Apr. 17, 2015.

Jones, Philip et al., Heterocyclic modulators of HIF activity for treatment of disease, Univ. Texas MD Anderson Cancer Center Institute, WO 2014031936 A2, International Preliminary Report on Patentability, publication date, Feb. 24, 2015.

Jones, Philip et al., Heterocyclic modulators of HIF activity for treatment of disease, Univ. Texas MD Anderson Cancer Center Institute, WO 2014031933A2, International Preliminary Report on Patentability, publication date, Feb. 24, 2015.

Jones, Philip et al., Heterocyclic modulators of HIF activity for treatment of disease, Univ. Texas MD Anderson Cancer Center Institute, WO 2014031928A1, International Preliminary Report on Patentability, publication date, Feb. 24, 2015.

Kalluraya et al., Studies on arylthiophene heterocycles. Part 1. Synthesis and biological activity of some 2-aryl/arylarnino-4-[5-(p-nitrophenyl)-2-thienyl)] thiazoles, Oriental Journal of Chemistry (1996), 12(2), 141-144, CAS Accession No. 748862.

Nakai Hisao et al., Preparation of nitrogen-containing heterocyclic compounds as p38 MAP kinase inhibitors, STN record of W02007040208, Acc No. 2007:410206, DN 146:421971, 2007.

Haerter M et al., "Inhibition of Hypoxia-Induced Gene Transcription by Substituted Pyrazolyl Oxadiazoles: Initial Lead Generation and Structure—Activity Relationships" ChemMedChem 9(1):61-6, 2013-11-27.

Ellinghaus P et al., "BAY 87-2243, a highly potent and selective inhibitor of hypoxia-induced gene activation has antitumor activities by inhibition of mitochondrial complex I," Cancer Medicine 2(5): 611-24, Aug. 20, 2013.

Gatta, A. et al., "Synthesis of imidazo[1,2-c]pyrazolo[4,3-e]pyrimidines, 1-2pyrazolo[4,3-e]1,2,4- triazolo[1,5-c]pyrimidines and 1,2,4-triazolo[5,1-i]purines as adenosine A2 receptor antagonists," Eur. J. Med Chern, 1993, vol. 28, pp. 569-576.

Coqueron PY et al., Iterative oxazole assembly via alpha-chloroglycinates: total synthesis of (-)-muscoride A., Angew Chem Int Ed Engl. Mar. 28, 2003;42(12):1411-1414.

Jones, Philip et al., Salts of heterocyclic modulators of hif activity for treatment of disease, Univ. Texas MD Anderson Cancer Center Institute, US20140073634A, Final rejection, Mar. 31, 2015.

Jones, Philip et al., Salts of heterocyclic modulators of hif activity for treatment of disease, Univ. Texas MD Anderson Cancer Center Institute, US20140073634A1, Final rejection, Oct. 22, 2015.

* cited by examiner

SALTS OF HETEROCYCLIC MODULATORS OF HIF ACTIVITY FOR TREATMENT OF DISEASE

This application claims the benefit of priority of U.S. Provisional Application No. 61/944,345, filed Feb. 25, 2014, the disclosure of which is hereby incorporated by reference as if written herein in its entirety.

The present disclosure relates to heterocyclic compounds, compositions, and methods to inhibit HIF pathway activity, more specifically to methods for treating diseases mediated by HIF pathway activity.

The heterodimeric HIF transcription factor is composed of a stable HIF1β (aka ARNT) and an oxygen regulatable HIFα subunit (HIF1α or EPAS1 (aka HIF2α) (Semenza, 2012b). Under normal physiological conditions, the capacity of the cell to degrade the HIFα subunits exceeds the amount of HIFα protein that is being synthesized. The HIFα subunit is regulated by hydroxylation at two key proline residues (i.e. $Pro^{402}$ and $Pro^{564}$ in HIF1α) by a family of proline hydroxylases (PHD1, PHD2 and PHD3), that utilize α-ketoglutarate and oxygen as substrates to generate hydroxylated HIFα, succinate and $CO_2$ (Kaelin and Ratcliffe, 2008). Hydroxylation of HIFα makes it a substrate for the VHL ubiquitin ligase complex, which promotes HIFα polyubiquitination, thus targeting HIFα for proteosomal degradation. This process is very rapid at normal oxygen levels, with a <5 minute half-life of HIFα protein, thus enabling rapid regulation of the complex and HIF activity in response to changes in oxygen levels (Maxwell et al., 1999).

Frequently in disease, the HIF pathway is activated by either reduced oxygen levels or genetic alterations that increase the amount of stabilized HIFα subunit (Semenza, 2012a). Increased HIFα levels occur through several mechanisms that include increased in HIFα subunit mRNA expression, HIFα protein translation, or through a decrease in HIFα protein degradation. Increased HIF leads to several biological pathways being activated through HIF mediated transcription of genes that promote stem cell maintenance, metabolic reprogramming, endothelial to mesenchymal transition (EMT), survival, proliferation, migration, pH regulation and angiogenesis.

A substantial body of preclinical experimentation and clinical evidence has implicated HIF as an important therapeutic target that is essential for the maintenance of a subset of tumors and a potential major contributor to therapeutic resistance and residual disease (Kaelin, 2011; Kaelin and Ratcliffe, 2008; Li et al., 2005; Semenza, 2012a; Semenza, 2012b). In numerous clinical studies, tumor hypoxia has been reported to correlate with poor prognosis and incomplete response to current therapeutic agents, including various chemotherapies as well as radiotherapy (Harada et al., 2012; Rohwer and Cramer, 2011; Wilson and Hay, 2011). This is most likely due to HIF regulation of procancerous mechanisms, including increased proliferation, activation of survival pathways such as autophagy, enhanced glycolysis as part of a metabolic reprogramming shift away from oxidative phosphorylation, increased migration/invasion promoting metastasis, maintenance of pluripotent "stem cell" population and stimulation of angiogenesis through the synthesis and secretion of pro-angiogenic growth factors.

The loss of any of several tumor suppressors (i.e. VHL, SDH, FH, TSC and others) and/or dysregulation of several oncogenic pathways (i.e. RAS and Pi3K) activate the HIF pathway and its downstream effector pathways, but do so in the presence of oxygen creating a "pseudohypoxic" state. These subsets of tumors become dependent on the HIF pathway for their continued growth. An example of a genetically driven HIF tumor indication is renal cell carcinoma (RCC), in which the tumor suppressor VHL is inactivated by mutation, deletion or promoter hypermethylation in 70% of tumors (Kim and Kaelin, 2004). VHL inactivation results in HIFα stabilization that is independent of oxygen concentration. In another example, tumors where either fumarate hydratase (FH) or a subunit in the succinate dehydrogenase (SDH) complex is inactivated, HIFα accumulation occurs due to inhibition of PHDs by succinate and fumarate (Bardella et al., 2011; Gill, 2012; Isaacs et al., 2005; Pollard et al., 2005). The lack of HIFα hydroxylation prevents VHL mediated degradation.

In other tumors, the Pi3K pathway is frequently mutated (i.e., PTEN loss, AKT, PIK3CA, TSC1/2, LKB1 and others) ultimately leading to an increase in the activity of mammalian target of rapamycin (mTOR), which results in an increase in HIFα protein translation to the point where it overwhelms the degradation pathway. Therefore, in tumors with active Pi3K pathway, HIF pathway activity is frequently increased (Wouters and Koritzinsky, 2008). Taken together, in tumors where the HIF pathway is driven by specific genetic changes, therapeutic interventions that inactivate the HIF pathway in genetically driven HIF dependent tumors may provide substantial therapeutic benefit as monotherapy or as part of a combination therapy.

In addition to the activation of HIF through genetic alterations, HIF is also activated in hypoxia that results from the tumor outgrowing the vasculature as well as a result of therapeutic intervention. HIF mediated survival of cells in hypoxia is a major contributor to resistance to therapies, lack of durable response and the foundation of residual disease. When tumor cells become hypoxic, several HIF dependent mechanisms prolong the survival of the cells in the harsh nutrient and oxygen deprived environment. These include genomic instability to promote adaptation (Klein and Glazer, 2010; Koi and Boland, 2011), metabolic reprogramming, induction of autophagy to recycle energy (Mazure and Pouyssegur, 2010), secretion of pro-angiogenic factors to promote neovascularization and cessation of pro-growth pathways. Severe hypoxia mediates innate resistance to radiotherapy and chemotherapy, which require oxygen and proliferation, respectively, as part of their mechanisms of action. Alternatively, resistance can be adaptive as in the case of anti-angiogenic therapies, such as anti-VEGF therapies, that create hypoxic niches due to the destruction of the vasculature, which creates more intratumoral hypoxia thus activating HIF and promoting its milieu of procancerous pathways. Multiple reports in mouse models of cancer show that treatment with an anti-VEGF therapy promoted metastasis, most likely through HIF mediated activation of tumor cell migration/invasion (Ebos et al., 2009; Paez-Ribes et al., 2009). Hypoxia has also been proposed to promote genomic alteration by increasing DNA damage, including impairment of mismatch repair, nucleotide excision repair, double strand break repair and homologous recombination repair. The introduction of point mutations, frameshifts, insertions, deletions, amplifications and translocations give rise to tumor heterogeneity and evolution that provide the genetic alterations that enable adaptive resistance of tumors.

In most tumor types, inhibition of the HIF pathway activity will sensitize tumors to standard of care therapies such as anti-angiogenic therapies, radiotherapies, chemotherapies and targeted therapies by either improving the perfusion of drug and oxygen throughout the tumor via normalization of vascular function (Carmeliet and Jain, 2011; Chauhan et al., 2012) and by directly targeting the resistant HIF activated tumor cells to inhibit HIF mediated survival pathways.

In addition to cancer, inactivation of HIF pathway would be beneficial for conditions where activation of HIF promotes the disease state through aberrant survival or through promotion of neovascularization. These include traumatic shock, pulmonary arterial hypertension, obstructive sleep apnea, cardiovascular diseases such as cardiac arrhythmia and heart failure, diseases that involve neoangiogenesis such as ocular macular degeneration and rheumatoid arthritis, sepsis and inflammation and diseases of the lung and kidney where fibrosis occurs due HIF mediated EMT (Arjamaa et al., 2009; Semenza, 2012a; Westra et al., 2010).

To date, numerous small molecules have been reported that down regulate the HIF pathway via several direct and indirect mechanisms which target various HIF intervention points (Jones and Harris, 2012; Poon et al., 2009; Semenza, 2012b). These include reducing HIFα mRNA, reducing HIFα protein translation, reducing reactive oxygen species (ROS), increasing HIFα degradation, disrupting HIFα/HIF1β dimerization or the HIFα interaction with p300, a co-factor for HIF translation. Genetic and pharmacological inhibition of the HIF pathway utilizing RNAi, genetic ablation or via small molecule inhibitors have been reported to reduce the growth of tumors in preclinical models clearly establishing that the HIF pathway performs a critical function in tumor growth and maintenance (Onnis et al., 2009). Hence, promoting HIFα degradation as part of a therapeutic intervention regime would be highly beneficial to patients.

Thus, there remains a need for compounds and methods for inhibiting HIF pathway activity.

Accordingly, the inventors herein disclose a series of heterocyclic compounds that inhibit HIF pathway activity and promote VHL and PHD mediated degradation of HIF. These compounds provide improved oral bioavailability Provided is a compound of structural Formula I $$(R_1)_n\text{-}A\text{-}Y_1\text{—}B\text{-}D\text{-}E\text{-}(R_3)_p \cdot (M)_a \cdot (H_2O)_b \quad (I)$$

wherein: M is selected from the group consisting of an inorganic acid, an organic acid, an amino acid; with the proviso that M is not trifluoroacetic acid; a is a fractional or whole number between about 0.5 and about 3.5 inclusive; b is a fractional or whole number between about 0 and about 10 inclusive; n is 0, 1, or 2; p is 0, 1, or 2; q is 0, 1, 2, 3, or 4; u is 0, 1, or 2; A is aryl or heteroaryl; B is

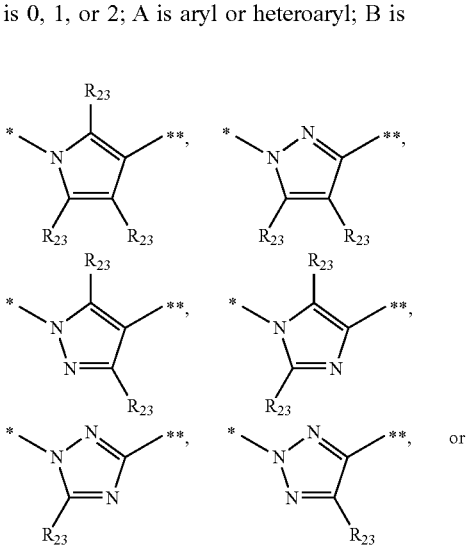

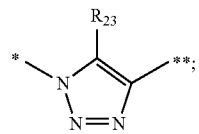

D is alkyl, heteroalkyl, alkoxy, alkylthio, carbonyl, alkylcarbonyl, carboxyl, oxy, thio, sulfinyl, sulfonyl, sulfonamido, amino, amido, alkylamino, or heteroaryl, any of which can be optionally substituted with one or more substituents hydrogen, deuterium, halogen, alkyl, haloalkyl, perhaloalkyl, heteroalkyl, hydroxyalkyl, acyl, cyano, hydroxy, alkoxy, haloalkoxy, perhaloalkoxy, cycloalkyl, aryl, heterocycloalkyl, heteroaryl, or oxo, any of which may be optionally substituted; E is aryl or heteroaryl; G is saturated 3- to 7-membered cycloalkyl or saturated 3- to 7-membered heterocycloalkyl; $R_1$ is —$Y_2$-alkyl-N($R_4$)$R_5$, hydrogen, deuterium, halogen, alkyl, alkenyl, alkynyl, haloalkyl, perhaloalkyl, heteroalkyl, hydroxyalkyl, aminoalkyl, acyl, carboxylalkyl, carbonyl, carboxyl, cyano, hydroxy, alkoxy, haloalkoxy, perhaloalkoxy, oxo, alkylthio, thiolalkyl, mercaptyl, thiol, sulfonate, sulfonamido, alkylsulfonyl, amino, amido, alkylamino, dialkylamino, carbamate, nitro, cycloalkyl, aryl, heterocycloalkyl, heteroaryl, cycloalkyloxy, aryloxy, heterocycloalkyloxy, heteroaryloxy,

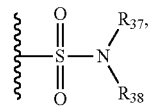

cycloalkylcarbonyl, arylcarbonyl, heterocycloalkylcarbonyl, heteroarylcarbonyl, cycloalkylalkyl, arylalkyl, heterocycloalkylalkyl, heterocycloalkylcarbonylalkyl, or heteroarylalkyl, any of which can be optionally substituted with one or more substituents hydrogen, deuterium, halogen, alkyl, alkenyl, alkynyl, haloalkyl, perhaloalkyl, heteroalkyl, hydroxyalkyl, amidoalkyl, acyl, carbonyl, carboxyl, carboxylalkyl, alkylcarbonyl, heteroalkylcarbonyl, hydroxyalkylcarbonyl, aminoalkylcarbonyl, alkylaminoalkylcarbonyl, alkenylcarbonyl, alkynylcarbonyl, alkoxyalkyl, carboxyl, cyano, hydroxy, alkoxy, haloalkoxy, perhaloalkoxy, oxo, alkylthio, thiol, acylthio, sulfonamido, alkylsulfonyl, amino, amido, carbamate, alkylamino, dialkylamino, alkylaminoalkyl, dialkylaminoalkyl, nitro, trisubstituted silyl, trisubstituted siloxy, cycloalkyl, aryl, heterocycloalkyl, heteroaryl, alkylheterocycloalkyl, any of which may be optionally substituted; $R_3$ is hydrogen, deuterium, halogen, alkyl, haloalkyl, perhaloalkyl, heteroalkyl, hydroxyalkyl, alkoxyalkyl, aminoalkyl, acyl, carbonyl, carboxyl, cyano, cyanoalkyl, hydroxy, alkoxy, haloalkoxy, perhaloalkoxy, alkoxyalkoxy, hydroxyalkoxy, oxo, alkylthio, mercaptyl, thiol, haloalkylthio, perhaloalkylthio, cyanoalkylthio, haloalkylsulfonyl, alkylsulfonyl, alkoxyalkylsulfonyl, cyanoalkylsulfonyl, sulfonate, sulfonamido, amino, amido, alkylamino, dialkylamino, carbamate, nitro, cycloalkyl, aryl, heterocycloalkyl, heteroaryl, cycloalkyloxy, aryloxy, heterocycloalkyloxy, heteroaryloxy, cycloalkylalkyl, arylalkyl, heterocycloalkylalkyl, or heteroarylalkyl, trisubstituted silyl, —SF$_5$, —C($R_{31}$)($R_{32}$))$_q$—O-alkyl, —(C($R_{31}$)($R_{32}$))$_q$—O-cycloalkyl, —S(O)$_u$-alkyl, —S(O)$_u$-cycloalkyl, cycloalkylthio, —CF$_3$, —OCF$_3$, —(C($R_{31}$)($R_{32}$))$_q$—OCF$_3$, saturated heterocycloalkyloxy, —(C($R_{31}$)($R_{32}$))$_q$—O-saturated heterocycloalkyl, —(C($R_{31}$)($R_{32}$))$_u$— saturated heterocycloalkyl, saturated heterocycloalkylthio, —S(O)$_u$-saturated heterocycloalkyl, —(C(R$_{31}$)(R$_{32}$))$_q$—OCF$_3$,

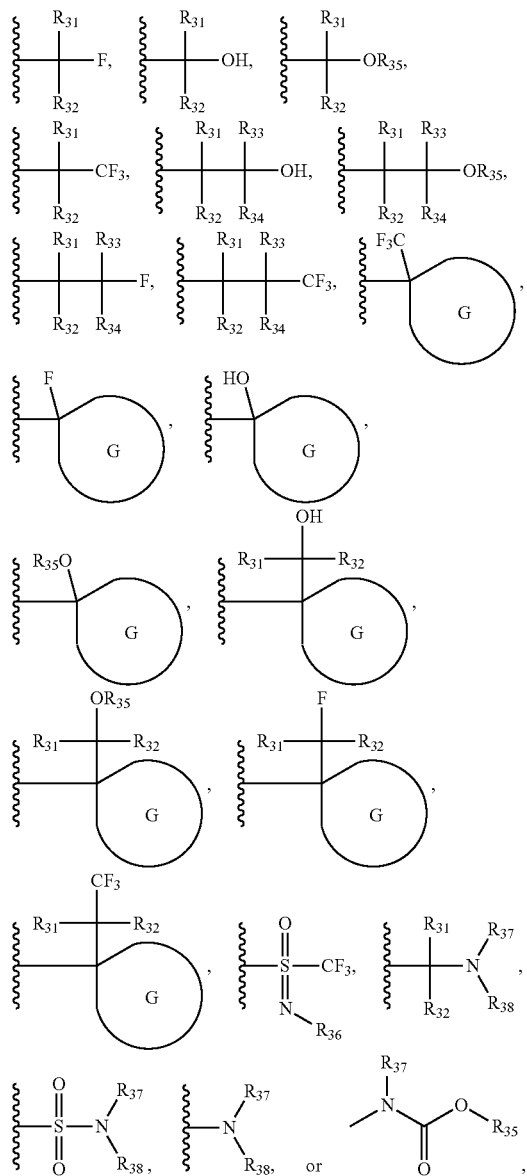

any of which may be optionally substituted; R$_4$ and R$_5$ are independently hydrogen, deuterium, alkyl, alkenyl, alkynyl, haloalkyl, perhaloalkyl, heteroalkyl, hydroxyalkyl, acyl, carbonyl, carboxyl, alkoxy, haloalkoxy, perhaloalkoxy, alkylsulfonyl, sulfonamido, amido, cycloalkyl, aryl, heterocycloalkyl, heteroaryl, cycloalkylalkyl, arylalkyl, heterocycloalkylalkyl, or heteroarylalkyl, or R$_4$ and R$_5$, taken together, form a heterocyloalkyl or heteroaryl, any of which can be optionally substituted with one or more substituents hydrogen, deuterium, halogen, alkyl, alkenyl, alkynyl, haloalkyl, perhaloalkyl, heteroalkyl, hydroxyalkyl, acyl, carbonyl, carboxyl, cyano, hydroxy, alkoxy, haloalkoxy, perhaloalkoxy, oxo, alkylthio, mercaptyl, thiol, sulfonate, sulfonamido, amino, amido, alkylamino, dialkylamino, carbamate, nitro, cycloalkyl, aryl, heterocycloalkyl, heteroaryl, cycloalkyloxy, aryloxy, heterocycloalkyloxy, heteroaryloxy, cycloalkylalkyl, arylalkyl, heterocycloalkyl-alkyl, or heteroarylalkyl, any of which may be optionally substituted; each R$_{23}$ is independently hydrogen, deuterium, halogen, alkyl, haloalkyl, perhaloalkyl, heteroalkyl, hydroxyalkyl, aminoalkyl, acyl, carbonyl, carboxyl, cyano, hydroxy, alkoxy, haloalkoxy, perhaloalkoxy, oxo, alkylthio, amino, alkylamino, dialkylamino, nitro, cycloalkyl, aryl, or heteroaryl, any of which may be optionally substituted; R$_{31}$, R$_{32}$, R$_{33}$, R$_{34}$, or R$_{36}$ are independently hydrogen, deuterium, alkyl, or perfluoroalkyl, any of which can be optionally substituted; R$_{35}$ is hydrogen, deuterium, alkyl, perfluoroalkyl, cycloalkyl, or saturated heterocycloalkyl, any of which can be optionally substituted; R$_{37}$ or R$_{38}$ are independently alkyl or perfluoroalkyl, or R$_{37}$ and R$_{38}$, taken together, form a heterocyloalkyl, any of which can be optionally substituted; Y$_1$ is alkyl, alkenyl, alkynyl, heteroalkyl, alkoxy, alkylthio, carbonyl, alkylcarbonyl, carboxyl, oxy, thio, sulfinyl, sulfonyl, sulfonamido, amino, amido, alkylamino, or carbamate, any of which can be optionally substituted with one or more substituents hydrogen, deuterium, halogen, alkyl, haloalkyl, perhaloalkyl, heteroalkyl, hydroxyalkyl, aminoalkyl, acyl, carbonyl, carboxyl, cyano, hydroxy, alkoxy, haloalkoxy, perhaloalkoxy, oxo, alkylthio, amino, alkylamino, dialkylamino, or cycloalkyl, any of which may be optionally substituted; Y$_2$ is a bond, carbonyl, alkylcarbonyl, carboxyl, oxy, thio, sulfinyl, sulfonyl, sulfonamido, amino, amido, alkylamino, or carbamate, any of which can be optionally substituted with one or more substituents hydrogen, deuterium, halogen, alkyl, alkenyl, alkynyl, haloalkyl, perhaloalkyl, heteroalkyl, hydroxyalkyl, acyl, carbonyl, carboxyl, cyano, hydroxy, alkoxy, haloalkoxy, perhaloalkoxy, oxo, alkylthio, mercaptyl, thiol, sulfonate, sulfonamido, amino, amido, alkylamino, dialkylamino, carbamate, cycloalkyl, aryl, heterocycloalkyl, heteroaryl, cycloalkyloxy, aryloxy, heterocycloalkyloxy, heteroaryloxy, cycloalkylalkyl, arylalkyl, heterocycloalkylalkyl, or heteroarylalkyl, any of which may be optionally substituted; if A is phenyl, B is not

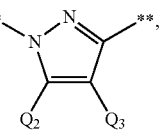

wherein Q$_2$ or Q$_3$ are freely substituted; if A is phenyl or pyridyl, Y$_1$ is CH$_2$, B is

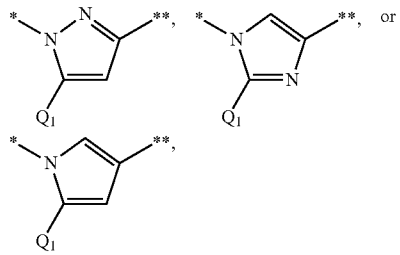

and Q$_1$ is methyl, ethyl, or trifluoromethyl, then D is not

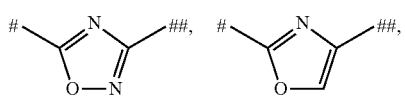

-continued

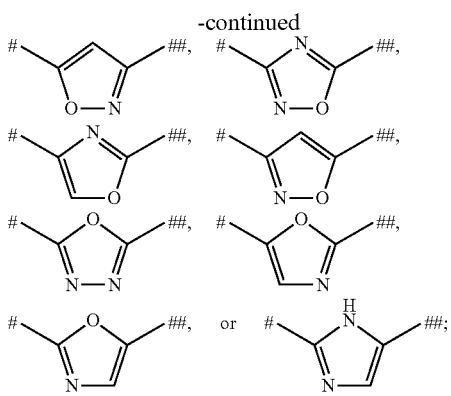

and wherein * represents the point of attachment to $Y_1$ and ** represents the point of attachment to D, and # represents the point of attachment to B and ## represents the point of attachment to E.

Provided is a compound selected from the group consisting of: 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole hydrochloride; 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole 2,2,2-trifluoroacetate; 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole methanesulfonate; or 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole benzenesulfonate.

Provided is a method of treatment of a HIF pathway-mediated disease comprising the administration of a therapeutically effective amount of a compound as disclosed herein to a patient in need thereof.

DEFINITIONS

Figure 1:
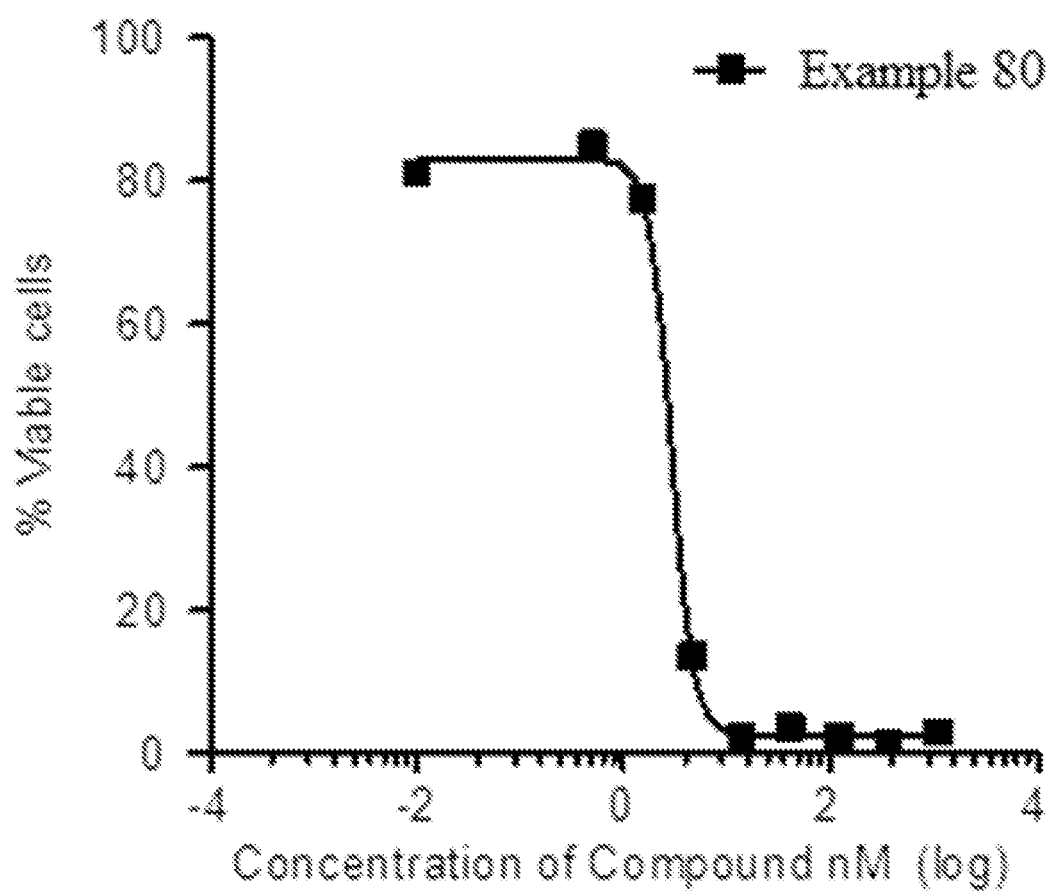
FIG. 1—Compounds of this disclosure inhibit the growth of diffuse large B-cell lymphoma TMD8 cells as shown by reduced number of viable cells following treatment with Example 80.

To facilitate understanding of the disclosure, a number of terms and abbreviations as used herein are defined below as follows:

Unless otherwise defined, all technical and scientific terms used herein have the same meaning as commonly understood by one of ordinary skill in the art to which this disclosure belongs. When a conflict occurs, the meaning ascribed herein controls.

When ranges of values are disclosed, and the notation "from n1 . . . to n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH₃ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')—group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)$NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, or heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group, with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type, including spiro-ring fused systems. The bicyclic and tricyclic types of isomer are exemplified in general by, bicyclo[1,1,1]pentane, camphor, adamantane, bicyclo[3,2,1] octane, and [4,4,1]-bicyclononane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from O, N, or S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from O, S, or N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from nitrogen, oxygen, or sulfur. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, cyclic sulfonamides, sulfoxides, N-oxides of tertiary nitrogen ring members, and carbocyclic fused, benzo fused, and spiro-ring fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, isothiazolidine, and the like. The heterocycle groups may be optionally substituted unless specifically prohibited.

The term "hydrogen," as used herein, refers to both protium ($^1$H) and deuterium ($^2$H). This definition extends to hydrogen atoms which appear in chemical structural drawings disclosed herein, including at sites where hydrogen atoms are not explicitly shown. For example, a chemical structure disclosed herein may include an ethyl group represented as

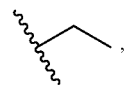 [SMILES: *CC]

which includes five hydrogen atoms which are not explicitly drawn, any of which can be protium ($^1$H) or deuterium ($^2$H). This definition also extends to hydrogen atoms which form a part of a named chemical substituent disclosed herein. For example, a generic chemical structure disclosed herein may recite an aryl group, which encompasses specific embodiments such as a phenyl group, which comprises five hydrogen atoms, any of which can be protium ($^1$H) or deuterium ($^2$H).

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

In certain embodiments, compounds disclosed herein are enriched with deuterium. Carbon-hydrogen bond strength is directly proportional to the absolute value of the ground-state vibrational energy of the bond. This vibrational energy depends on the mass of the atoms that form the bond, and increases as the mass of one or both of the atoms making the bond increases. Since deuterium (D) has twice the mass of protium ($^1$H), a C-D bond is stronger than the corresponding C—$^1$H bond. If a C—$^1$H bond is broken during a rate-determining step in a chemical reaction (i.e. the step with the highest transition state energy), then substituting a deuterium for that protium will cause a decrease in the reaction rate, including cases where a C—H bond is broken during metabolism of a compound disclosed herein. This phenomenon is known as the Deuterium Kinetic Isotope Effect (DKIE). The magnitude of the DKIE can be expressed as the ratio between the rates of a given reaction in which a C—$^1$H bond is broken, and the same reaction where deuterium is substituted for protium. The DKIE can range from about 1 (no isotope effect) to very large numbers, such as 50 or more. The deuteration approach has the potential to slow the metabolism of the compounds disclosed herein. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. Deuterium can be introduced into a compound as disclosed herein by synthetic techniques that employ deuterated reagents, whereby incorporation rates are predetermined; and/or by exchange techniques, wherein incorporation rates are determined by equilibrium conditions, and may be highly variable depending on the reaction conditions. Synthetic techniques where deuterium is directly and specifically inserted by a deuterated reagent of known isotopic content, can yield high deuterium abundance, but can be limited by the chemistry required. Exchange techniques, on the other hand, may yield lower deuterium incorporation, often with the isotope being distributed over many sites on the molecule.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms selected from O, S, or N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer to the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any chemical definition herein may be used in combination with any other chemical definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

A "salt" as used herein means an ionic compound with a net neutral charge formed by combination of one type of a cation with one type of an anion in an integer or non-integer ratio, and optionally with one type of associated solvent molecule in an integer or non-integer ratio. The term "compound as disclosed herein" or "compound of this disclosure" includes salts.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position. When a group in a chemical formula is designated to be "a bond," the group reduces to a linkage between the groups to which it is linked in the formula. By way of example, in Formula I, when $Y_2$ is a bond, it becomes a direct link between A and -alkyl-$N(R_4)R_5$, forming $R_5(R_4)$N-alkyl-A-$Y_1$—(B—$(R_2)_m$)—D-E-$(R_3)_p$.

As used herein, the term "modulate" means to increase or decrease the activity of a target or the amount of a substance.

As used herein, the term "increase" or the related terms "increased," "enhance" or "enhanced" refers to a statistically significant increase, and the terms "decreased," "suppressed," or "inhibited" to a statistically significant decrease. For the avoidance of doubt, an increase generally refers to at least a 10% increase in a given parameter, and can encompass at least a 20% increase, 30% increase, 40% increase, 50% increase, 60% increase, 70% increase, 80% increase, 90% increase, 95% increase, 97% increase, 99% or even a 100% increase over the control, baseline, or prior-in-time value. Inhibition generally refers to at least a 10% decrease in a given parameter, and can encompass at least a 20% decrease, 30% decrease, 40% decrease, 50% decrease, 60% decrease, 70% decrease, 80% decrease, 90% decrease, 95% decrease, 97% decrease, 99% or even a 100% decrease over the control value.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single formulation (e.g., a capsule or injection) having a fixed ratio of active ingredients or in multiple, separate dosage forms for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, polymorphs, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis.

In the present disclosure, the term "radiation" means ionizing radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art. The amount of ionizing radiation needed in a given cell generally depends on the nature of that cell. Means for determining an effective amount of radiation are well known in the art. Used herein, the term "an effective dose" of ionizing radiation means a dose of ionizing radiation that produces an increase in cell damage or death.

The term "radiation therapy" refers to the use of electromagnetic or particulate radiation in the treatment of neoplasia and includes the use of ionizing and non-ionizing radiation.

As used herein, the term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound and N-oxides of amines or heterocyclic groups such as pyridine.

The term "metabolite" refers to a compound produced through biological transformation of a compound following administration to a subject. In order to eliminate foreign substances such as therapeutic agents, the animal body expresses various enzymes, such as the cytochrome P450 enzymes (CYPs), esterases, proteases, reductases, dehydrogenases, and monoamine oxidases, to react with and convert these foreign substances to more polar intermediates or metabolites for renal excretion. Such metabolic reactions frequently involve the oxidation of a carbon-hydrogen (C—H) bond to either a carbon-oxygen (C—O) or a carbon-carbon (C—C)-bond, N-oxidation, or covalent bonding of a polar molecule or functional group (such as sulfate, glucuronic acid, glutathione, or glycine, to the therapeutic agent. The resultant metabolites may be stable or unstable under physiological conditions, and can have substantially different pharmacokinetic, pharmacodynamic, and acute and long-term toxicity profiles relative to the parent compounds. Certain compounds disclosed herein may, after administration to a subject result in formation of metabolites, which in some cases have biological activity as HIF pathway modulators or activity against other biological systems. In certain embodiments, metabolites of the compounds disclosed herein include N-oxides, particularly N-oxides of heterocyclic groups such as pyridine. In further embodiments, metabolites of compounds disclosed herein may themselves have substantial activity as HIF pathway inhibitors.

The compounds disclosed herein can exist as therapeutically acceptable salts. Suitable acid addition salts include those formed with both organic and inorganic acids, and will normally be pharmaceutically acceptable. However, salts of non-pharmaceutically acceptable salts may be of utility in the preparation and purification of the compound in question. Basic addition salts may also be formed and be pharmaceutically acceptable. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. For a more complete discussion of the preparation and selection of salts, refer to Pharmaceutical Salts: Properties, Selection, and Use (Stahl, P. Heinrich. Wiley-VCHA, Zurich, Switzerland, Second, Revised Edition, 2011.2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion.

Basic addition salts can be prepared during the final isolation and purification of the compounds, often by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium (e.g., NaOH), potassium (e.g., KOH), calcium (including $Ca(OH)_2$), magnesium (including $Mg(OH)_2$ and magnesium acetate), zinc, (including $Zn(OH)_2$ and zinc acetate) and aluminum, as well as non-toxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N, N'-dibenzylethylenediamine, N, N'-diethylethanolamine, N, N'-dimethylethanolamine, triethanolamine, and tromethamine. Basic amino acids such as 1-glycine and 1-arginine, and amino acids which may be zwitterionic at neutral pH, such as betaine (N,N,N-trimethylglycine) are also contemplated.

Salts disclosed herein may combine in 1:1 molar ratios, and in fact this is often how they are initially synthesized. However, it will be recognized by one of skill in the art that the stoichiometry of one ion in a salt to the other may be otherwise. Salts shown herein may be, for the sake of convenience in notation, shown in a 1:1 ratio; all possible stoichiometric arrangements are encompassed by the scope of the present disclosure.

The terms, "polymorphs" and "polymorphic forms" and related terms herein refer to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between polymorphs).

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

The term, "solvate," as used herein, refers to a crystal form of a substance which contains solvent. The term "hydrate" refers to a solvate wherein the solvent is water.

Techniques for characterizing polymorphs include, but are not limited to, differential scanning calorimetry (DSC), X-ray powder diffractometry (XRPD), thermal gravimetric analysis (TGA), dynamic vapor sorption/desorption (DVS), single crystal X-ray diffractometry, vibrational spectroscopy, e.g. IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

As used herein, "solid" when referring to a salt form means relatively solid, at room temperature, and/or containing a substantial amount of solids. A solid may be amorphous in form and/or be a solvated solid with some quantity of residual or coordinated of solvent molecules. A crystalline salt is an example of a solid. By way of example, a wax could be considered a solid, whereas an oil would not be.

A "solid composition" as used herein includes a salt of a compound, or a polymorph or amorphous solid form thereof.

While it may be possible for the compounds and prodrugs disclosed herein to be administered as the raw chemical, it is also possible to present them as a pharmaceutical formulation. Accordingly, provided herein are pharmaceutical formulations which comprise one or more of certain compounds and prodrugs disclosed herein, or one or more pharmaceutically acceptable salts, esters, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, intranasal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds and prodrugs disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds and prodrugs may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds and prodrugs may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds and prodrugs which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds and prodrugs to allow for the preparation of highly concentrated solutions.

In addition to the formulations described previously, a compound or prodrug as disclosed herein may also be formulated as a depot preparation. Such long acting formulations may be administered by implantation (for example subcutaneously or intramuscularly) or by intramuscular injection. Thus, for example, the compounds and prodrugs may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and *acacia* or tragacanth.

The compounds and prodrugs may also be formulated in rectal compositions such as suppositories or retention enemas, e.g., containing conventional suppository bases such as cocoa butter, polyethylene glycol, or other glycerides.

Certain compounds and prodrugs disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds and prodrugs may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds and prodrugs disclosed herein may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Intranasal delivery, in particular, may be useful for delivering compounds to the CNS. It had been shown that intranasal drug administration is a noninvasive method of bypassing the blood-brain barrier (BBB) to deliver neurotrophins and other therapeutic agents to the brain and spinal cord. Delivery from the nose to the CNS occurs within minutes along both the olfactory and trigeminal neural pathways. Intranasal delivery occurs by an extracellular route and does not require that drugs bind to any receptor or undergo axonal transport. Intranasal delivery also targets the nasal associated lymphatic tissues (NALT) and deep cervical lymph nodes. In addition, intranasally administered therapeutics are observed at high levels in the blood vessel walls and perivascular spaces of the cerebrovasculature. Using this intranasal method in animal models, researchers have successfully reduced stroke damage, reversed Alzheimer's neurodegeneration, reduced anxiety, improved memory, stimulated cerebral neurogenesis, and treated brain tumors. In humans, intranasal insulin has been shown to improve memory in normal adults and patients with Alzheimer's disease. Hanson L R and Frey W H, 2nd, J Neuroimmune Pharmacol. 2007 March; 2(1):81-6. Epub 2006 Sep. 15.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds and prodrugs may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compound or prodrug which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds and prodrugs can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds and prodrugs described herein (or a pharmaceutically acceptable salt or ester thereof) in combination with another therapeutic agent. By way of example only, if one of the side effects experienced by a patient upon receiving one of the compounds herein for the treatment of cancer is nausea, then it may be appropriate to administer an antiemetic agent in combination. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for cancer involving administration of one of the compounds described herein, increased therapeutic benefit may result by also providing the patient with another therapeutic agent for cancer. In any case, regardless of the disease, disorder or condition being treated, the overall benefit experienced by the patient may simply be additive of the two therapeutic agents or the patient may experience a synergistic benefit.

The compounds disclosed herein, including compounds of Formula I, are also useful as chemo- and radio-sensitizers for cancer treatment. They are useful for the treatment of mammals which have previously undergone or are presently undergoing or will be undergoing treatment for cancer. Such other treatments include chemotherapy, radiation therapy, surgery or immunotherapy, such as cancer vaccines.

The instant compounds are particularly useful in combination with therapeutic, anti-cancer and/or radiotherapeutic agents. Thus, the present disclosure provides a combination of the presently compounds of Formula I with therapeutic, anti-cancer and/or radiotherapeutic agents for simultaneous, separate or sequential administration. The compounds of this disclosure and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

The therapeutic agent, anti-cancer agent and/or radiation therapy can be administered according to therapeutic protocols well known in the art. It will be apparent to those skilled in the art that the administration of the therapeutic agent, anti-cancer agent and/or radiation therapy can be varied depending on the disease being treated and the known effects of the anti-cancer agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., anti-neoplastic agent or radiation) on the patient, and in view of the observed responses of the disease to the administered therapeutic agents, and observed adverse affects.

Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Any suitable means for delivering radiation to a tissue may be employed in the present disclosure. Common means of delivering radiation to a tissue is by an ionizing radiation source external to the body being treated. Alternative methods for delivering radiation to a tissue include, for example, first delivering in vivo a radiolabeled antibody that immunoreacts with an antigen of the tumor, followed by delivering in vivo an effective amount of the radio labeled antibody to the tumor. In addition, radioisotopes may be used to deliver ionizing radiation to a tissue or cell. Additionally, the radiation may be delivered by means of a radiomimetic agent. As used herein a "radiomimetic agent" is a chemotherapeutic agent, for example melphalan, that causes the same type of cellular damage as radiation therapy, but without the application of radiation.

In one embodiment, the compounds of formula I can be administered in combination with one or more agent selected from aromatase inhibitors, anti-estrogens, anti-progesterons, anti-androgens, or gonadorelin agonists, anti-inflammatory agents, antihistamines, anti-cancer agent, inhibitors of angiogenesis, topoisomerase 1 and 2 inhibitors, microtubule active agents, alkylating agents, antineoplastic, antimetabolite, dacarbazine (DTIC), platinum containing compound, lipid or protein kinase targeting agents, protein or lipid phosphatase targeting agents, anti-angiogenic agents, agents that induce cell differentiation, bradykinin 1 receptor and angiotensin II antagonists, cyclooxygenase inhibitors, heparanase inhibitors, lymphokines or cytokine inhibitors, bisphosphonates, rapamycin derivatives, anti-apoptotic pathway inhibitors, apoptotic pathway agonists, PPAR agonists, HSP90 inhibitor, smoothened antagonist, inhibitors of Ras isoforms, telomerase inhibitors, protease inhibitors, metalloproteinase inhibitors, aminopeptidase inhibitors, imununomodulators, therapeutic antibody and a protein kinase inhibitor, e.g., a tyrosine kinase or serine/threonine kinase inhibitor.

In another embodiment is provided a combination of a compound of formula I and an anti-cancer agent for simultaneous, separate or sequential administration.

Examples of cancer agents or chemotherapeutic agents for use in combination with the compounds as disclosed herein can be found in *Cancer Principles and Practice of Oncology* by V. T. Devita and S. Hellman (editors), 6th edition (Feb. 15, 2001), Lippincott Williams & Wilkins Publishers, and WO 2006/061638. A person of ordinary skill in the art would be able to discern which combinations of agents would be useful based on the particular characteristics of the drugs and the cancer involved. Classes of such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs), agents that interfere with cell cycle checkpoints, PARP inhibitors, HDAC inhibitors, Smo antagonists (HH inhibitors), HSP90 inhibitors, CYP17 inhibitors, 3rd generation AR antagonists, JAK inhibitors e.g. Ruxolitinib (trade name Jakafi, and BTK kinase inhibitors.

Anticancer agents suitable for use in the combination therapy with compounds as disclosed herein include, but are not limited to: 1) alkaloids and natural product drugs, including, microtubule inhibitors (e.g., Vincristine, Vinblastine, and Vindesine, and vinorelbine etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-161, and Teniposide [VM-261, etc.), and agents that target topoisomerase I (e.g., Camptothecin, topotecan (Hycamtin) and Irinotecan [CPT-11], rubitecan (Orathecin)etc.); 2) covalent DNA-binding agents [alkylating agents], including, nitrogen mustards (e.g., Mechlorethamine, chlormethine, Chlorambucil, Cyclophosphamide, estramustine (Emcyt, Estracit), ifosfamide, Ifosphamide, melphalan (Alkeran) etc.); alkyl sulfonates like Busulfan [Myleran], nitrosoureas (e.g., Carmustine or BCNU (bis-chloroethylnitrosourea), fotemustine Lomustine, and Semustine, streptozocin etc.), and other alkylating agents (e.g., Dacarbazine, procarbazine ethylenimine/methylmelamine, thriethylenemelamine (TEM), triethylene thiophosphoramide (thiotepa), hexamethylmelamine (HMM, altretamine), and Mitocycin, uramustine etc.) including Temozolomide (brand names Temodar and Temodal and Temcad), altretamine (also hexalen) and mitomycin; 3) noncovalent DNA-binding agents [antitumor antibiotics], including nucleic acid inhibitors (e.g., Dactinomycin [Actinomycin D1, etc.), anthracyclines (e.g., Daunorubicin [Daunomycin, and Cerubidine], Doxorubicin [Adrianycin], epirubicin (Ellence), and Idarubicin [Idamycin], valrubicin (Valstar) etc.), anthracenediones (e.g., anthracycline analogues, such as, [Mitoxantrone], etc.), bleomycins (Blenoxane), etc., amsacrine and plicamycin (Mithramycin), dactinomycin, mitomycin C: 4) antimetabolites, including, antifolates (e.g., Methotrexate, Folex, aminopterin, pemetrexed, raltitrexed and Mexate, trimetrexate etc.), purine antimetabolites (e.g., 6-Mercaptopurine[6-MP, Purinethol], cladribine, 6-Thioguanine[6-TG], clofarabine (Clolar, Evoltra), Azathioprine, Acyclovir, Fludarabine or fludarabine phosphate (Fludara) Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)], capecitabine Carmofur or HCFU (1-hexylcarbamoyl-5-fluorouracil), tegafur etc.), gemcitabine (Gemzar), and cytosine arabinosides (e.g., Cytarabine, or cytosine arabinoside, Cytosar [ara-C] and Fludarabine, 5-azacytidine, 2,2'-difluorodeoxycytidine etc.) and hydroxyurea (Hydrea and Droxia, hydroxycarbamide), plus lonidamine; 5) enzymes, including, L-asparaginase and derivatives such as pegaspargase (Oncaspar), and RNAse A; 7) hormones and antagonists, Examples of hormones and hormonal analogues believed to be useful in the treatment of neoplasms include, but are not limited to antiestrogens and selective estrogen receptor modulators (SERMs), such as tamoxifen, toremifene, raloxifene, iodoxyfene, droloxifene, 4-hydroxytamoxifen, trioxifene, keoxifene, onapristone; anti-androgens; such as enzalutamide (Xtandi®), flutamide, nilutamide, bicalutamide, leuprolide, and goserelin, and cyproterone acetate; adrenocorticosteroids such as prednisone and prednisolone; aminoglutethimide, finasteride and other aromatase inhibitors such as anastrozole, letrazole, vorazole, exemestane, formestanie, and fadrozole; Estrogen Receptor Downregulators (EROs) including Faslodex or fulvestrant, progestrins such as megestrol acetate; Sa-reductase inhibitors such as finasteride and dutasteride; and gonadotropin-releasing hormones (GnRH) and analogues thereof, such as Leutinizing Hormone-releasing Hormone (LHRH) agonists and antagonists such as goserelin luprolide, leuprorelin and buserelin; 8) platinum compounds (e.g., Cisplatin and Carboplatin, oxaliplatin, Triplatin tetranitrate (rINN; also known as BBR3464), eptaplatin, lobaplatin, nedaplatin, or satraplatin etc.); 9) retinoids such as bexarotene (Targretin); 10) proteasome inhibitors such as bortezomib and carfilzomib (Kyprolis®); 11) anti-mitotics in addition to diterpenoids and vinca alkaloids include pololike kinase (PLK) inhibitors, mitotic kinesin spindle protein (KSP) inhibitors including SB-743921 and MK-833 and CenpE inhibitors; 12) monoclonal antibodies, including cancer immunotherapy monoclonal antibodies and humanized monoclonal antibodies. For example: 12-a) cancer immunotherapy monoclonal antibodies include agents selected from the group consisting of Trastuzumab (Herceptin®), an example of an anti-erbB2 antibody inhibitor of growth factor function; cetuximab (Erbitux™ C225), an example of an anti-erbB1 antibody inhibitor of growth factor function; bevacizumab (Avastin®), an example of a monoclonal antibody directed against VEGFR; rituximab, alemtuzumab, gemtuzumab, panitumumab, tositumomab, pertuzumab; 12-b) humanized monoclonal antibodies with therapeutic potential as chemotherapeutic agents in combination include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab (Perjeta®), pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab; 13) monoclonal antibodies conjugated with anticancer drugs, toxins, and/or radionuclides, etc. gemtuzumab ozogamicin (MYLOTARG), trastuzumab emtansine (T-DM1)/ado-trastuzumab emtansine (Kadcyla®); 14) biological response modifiers (e.g., interferons [e.g., IFN-.alpha., etc.] and interleukins [e.g., IL-2, etc.], denileukin diftitox (Ontak), G-CSF, GM-CSF: etc.); 15) adoptive immunotherapy; Immunotherapeutic regimens include ex-vivo and in-vivo approaches to increasing immunogenicity of patient tumor cells such as transfection with cytokines (eg. IL-2 or aldesleukin, IL-4, GMCFS), as well as IL-1, IL-3, IL-4, IL-5, IL-6, IL-7, IL-8, IL-9, IL-10, IL-11, IL-12, and active biological variants approaches to increase T-cell activity, approaches with transfected immune cells and approaches with antiidiotypic antibodies; 16) immunosuppressant selected from the group consisting of fingolimod, cyclosporine A, Azathioprine, dexamethasone, tacrolimus, sirolimus, pimecrolimus, mycophenolate salts, everolimus, basiliximab, daclizumab, anti-thymocyte globulin, anti-lymphocyte globulin, and tofacitinib. Agents capable of enhancing antitumor immune responses, such as CTLA4 (cytotoxic lymphocyte antigen 4) antibodies such as Ipilimumab (MDX-010 or MDX-101, Yervoy) and tremelimumab, and other agents capable of blocking CTLA4; 17) immune modulators, for use in conjunction with the compound as disclosed herein include staurosprine and macrocyclic analogs thereof, including UCN-01, CEP-701 and midostaurin; squalamine; DA-9601; alemtuzumab; interferons (e.g. IFN-α, IFN-b etc.); altretamine (Hexalen®); SU 101 or leflunomide; imidazoquinolines such as resiquimod, imiquimod, anti-PD-1 human monoclonal antibodies MDX-1106 (also known as BMS-936558), MK3475, CT-011, and AMP-224, anti-PD-L1 monoclonal antibodies such as MDX-1105, anti-OX40 monoclonal antibodies, and LAG3 fusion proteins such as IMP321g, anti-B7-H3 monoclonal antibodies such as MGA271, anti-B7-H4 monoclonal antibodies, and anti-TIM3 monoclonal antibodies; 18) hematopoietic growth factors; 19) agents that induce tumor cell differentiation (e.g., tretinoin (all trans retinoic acid) (brand names Aberela, Airol, Renova, Atralin, Retin-A, Avita, Retacnyl, Refissa, or Stieva-A)); 20) gene therapy techniques; such as gene therapy vaccines, for example, ALLOVECTIN®, LEUVECTIN®, and V AXID®; 21) antisense therapy techniques; 22) tumor vaccines; include Avicine®; oregovomab (OvaRex®); Theratope® (STn-KLH); Melanoma Vaccines; GI-4000 series (GI-4014, GI-4015, and GI-4016), which are directed to five mutations in the Ras protein; GlioVax-1; MelaVax; Advexin® or INGN-201; Sig/E7/LAMP-1, encoding HPV-16 E7; MAGE-3 Vaccine or M3TK; HER-2VAX; ACTIVE, which stimulates T-cells specific for tumors; GM-CSF cancer vaccine; and *Listeria* onocytogenes-based vaccines; 23) therapies directed against tumor metastases (e.g., Batimistat, etc.); 24) inhibitors of angiogenesis. Receptor kinase angiogenesis inhibitors may also find use in the present disclosure. Inhibitors of angiogenesis related to VEGFR and TIE-2. Other inhibitors may be used in combination with the compounds of the disclosure. For example, anti-VEGF antibodies, which do not recognize VEGFR (the receptor tyrosine kinase), but bind to the ligand; small molecule inhibitors of integrin (alphav beta3) that inhibit angiogenesis; endostatin and angiostatin (non-RT) may also prove useful in combination with the compounds of the disclosure. One example of a VEGFR antibody is bevacizumab (Avastin®). Other anti-angiogenic compounds include acitretin, fenretinide, thalidomide, zoledronic acid, angiostatin, aplidine, cilengtide, combretastatin A-4, endostatin, halofuginone, rebimastat, removab, Lenalidomid (Revlimid), squalamine, Vitaxin, and pomalidomide (Pomalyst®); 25) signal transduction pathway inhibitors. Signal transduction pathway inhibitors are those inhibitors which block or inhibit a chemical process which evokes an intracellular change. As used herein these changes include, but are not limited to, cell proliferation or differentiation or survival. Signal transduction pathway inhibitors useful in the present disclosure include, but are not limited to, inhibitors of receptor tyrosine kinases, non-receptor tyrosine kinases, SH2/SH3 domain blockers, serine/threonine kinases, phosphatidyl inositoi-3-0H kinases, myoinositol signaling, and Ras oncogenes. Signal transduction pathway inhibitors may be employed in combination with the compounds of the disclosure; 26) kinase inhibitors, including tyrosine kinases, serine/threonine kinases, kinases involved in the IGF-1 R signaling axis, PI3k/AKT/mTOR pathway inhibitors, and SH2/SH3 domain blockers. Examples of relevant kinases include: 26-a) tyrosine kinases. Several protein tyrosine kinases catalyze the phosphorylation of specific tyrosine residues in various proteins involved in the regulation of cell growth. Such protein tyrosine kinases can be broadly classified as receptor or non-receptor kinases. Receptor tyrosine kinase inhibitors which may be combined with the compounds of the disclosure include those involved in the regulation of cell growth, which receptor tyrosine kinases are sometimes referred to as "growth factor receptors." Examples of growth factor receptor inhibitors, include but are not limited to inhibitors of: insulin growth factor receptors (IGF-1 R, IR and IRR); epidermal growth factor family receptors (EGFR, ErbB2, and ErbB4); platelet derived growth factor receptors (PDGFRs), vascular endothelial growth factor receptors (VEGFRs), tyrosine kinase with immunoglobulin-like and epidermal growth factor homology domains (TIE-2), macrophage colony stimulating factor (c-FMS), c-KIT, cMET, fibroblast growth factor receptors (FGFRs), hepatocyte growth factor receptors (HGFRs), Trk receptors (TrkA, TrkB, and TrkC), ephrin (Eph) receptors, the RET protooncogene, and Human Epidermal Growth Factor Receptor 2 (HER-2). Examples of small molecule inhibitors of epidermal growth factor receptors include but are not limited to gefitinib, lapatinib (Tykerb®), erlotinib (Tarceva®), afatinib (Gilotrif®, Tomtovok®, and Tovok®), and. lmatinib (Gleevec®) is one example of a PDGFR inhibitor. Examples of VEGFR inhibitors include pazopanib (Votrient™) Vandetanib (ZD6474), AZD2171, vatalanib (PTK-787), Axitinib (AG013736; Inlyta®), dovitinib (CHIR-258), cabozantinib (Cometriq®), sunitinib, and sorafenib. Protein Kinase C (PKC) inhibitors, such as ruboxistaurin, AEB071 (Sotrastaurin) LY-317615 and perifosine. Examples of small molecule inhibitors of multiple tyrosine kinases include but are not limited to bosutinib (Bosulif®) and. Other kinase inhibitors include but are not limited to BIBF-1120, dasatinib (sprycel), pelitinib, nilotinib, and lestaurtinib (CEP-701). Tyrosine kinases that are not transmembrane growth factor receptor kinases are termed non-receptor, or intracellular tyrosine kinases. Inhibitors of non-receptor tyrosine kinases are sometimes referred to as "anti-metastatic agents" and are useful in the present disclosure. Targets or potential targets of anti-metastatic agents, include, but are not limited to, c-Src, Lck, Fyn, Yes, Jak, Abl kinase (c-Abl and Bcr-Abl), FAK (focal adhesion kinase) and Bruton's tyrosine kinase (BTK). Examples of small molecule inhibitors of Bcr-Abl include but are not limited to ponatinib (Iclusig®). Non-receptor kinases and agents, which inhibit non-receptor tyrosine kinase function, are described in Sinha, S. and Corey, S. J., *J. Hematother. Stem Cell Res.* (1999) 8 465-80; and Bolen, J. B. and Brugge, J. S., *Annu. Rev. of Immunol.* (1997) 15 371-404; 26-b) serine/threonine kinases. Inhibitors of serine/threonine kinases may also be used in combination with the compounds of the disclosure in any of the compositions and methods described above. Examples of serine/threonine kinase inhibitors that may also be used in combination with a compound of the present disclosure include, but are not limited to, polo-like kinase inhibitors (Pik family e.g., Plk1, Plk2, and Plk3), which play critical roles in regulating processes in the cell cycle including the entry into and the exit from mitosis; MAP kinase cascade blockers, which include other Ras/Raf kinase inhibitors, mitogen or extracellular regulated kinases (MEKs), and extracellular regulated kinases (ERKs); Aurora kinase inhibitors (including inhibitors of Aurora A and Aurora B); protein kinase C (PKC) family member blockers, including inhibitors of PKC subtypes (alpha, beta, gamma, epsilon, mu, lambda, iota, zeta); inhibitors of kappa-B (lkB) kinase family (IKK-alpha, IKK-beta); PKB/Akt kinase family inhibitors; and inhibitors of TGF-beta receptor kinases. Examples of Plk inhibitors are described in PCT Publication No. WO04/014899 and WO07/03036; 26-c) kinases involved in the IGF-1 R signaling axis. Inhibitors of kinases involved in the IGF-1 R signaling axis may also be useful in combination with the compounds of the present disclosure. Such inhibitors include but are not limited to inhibitors of JNK1/2/3, PI3K, AKT and MEK, and 14.3.3 signaling inhibitors; 26-d) PI3k/AKT/mTOR pathway inhibitors, including GDC-0941, XL-147, GSK690693 and temsirolimus, SF-1126 (PI3K inhibitor,), BEZ-235 (PI3K inhibitor); 26-e) SH2/SH3 domain blockers. SH2/SH3 domain blockers are agents that disrupt SH2 or SH3 domain binding in a variety of enzymes or adaptor proteins including, but not limited to, PI3-K p85 subunit, Src family kinases, adaptor molecules (She, Crk, Nck, Grb2) and Ras-GAP. Examples of Src inhibitors include, but are not limited to, dasatinib and BMS-354825 (*J. Med. Chern.* (2004) 4 7 6658-6661); 27) inhibitors of Ras oncogenes. Inhibitors of Ras oncogene may also be useful in combination with the compounds of the present disclosure. Such inhibitors include, but are not limited to, inhibitors of farnesyltransferase, geranyl-geranyl transferase, and CAAX proteases as well as anti-sense oligonucleotides, ribozymes and immunotherapy. Such inhibitors have been shown to block Ras activation in cells containing mutant Ras, thereby acting as antiproliferative agents; 28) Raf/MEK/ERK pathway modulators. The Raf/MEK/ERK pathway is critical for cell survival, growth, proliferation and tumorigenesis. Li, Nanxin, et al. "B-Raf kinase inhibitors for cancer treatment." Current Opinion in Investigational Drugs. Vol. 8, No. 6 (2007): 452-456. Raf kinases exist as three isoforms, A-Raf, B-Raf and C-Raf. Among the three isoforms, studies have shown that B-Raf functions as the primary MEK activator. B-Raf is one of the most frequently mutated genes in human cancers. B-Raf kinase represents an excellent target for anticancer therapy based on preclinical target validation, epidemiology and drugability. Small molecule inhibitors of B-Raf are being developed for anticancer therapy. Examples of small molecule inhibitors of B-Raf include but are not limited to dabrafenib (Tafinlar®). Nexavar® (sorafenib tosylate) is a multikinase inhibitor, which includes inhibition of B-Raf, and is approved for the treatment of patients with advanced renal cell carcinoma and unresectable hepatocellular carcinoma. Other Raf inhibitors have also been disclosed or have entered clinical trials, for example GSK-2118436, RAF-265, vemurafenib (Zelboraf, PLX-4032), PLX3603 and XL-281. Examples of small molecule inhibitors of MEK include but are not limited to trametinib (Mekinist®), Other MEK inhibitors include ARRY-886 (AZD6244); 29) Cell cycle signaling inhibitors, including inhibitors of cyclin dependent kinases (CDKs) are also useful in combination with the compounds of the disclosure in the compositions and methods described above. Examples of cyclin dependent kinases, including CDK2, CDK4, and CDK6 and inhibitors for the same are described in, for instance, Rosania G. R. et al., *Exp. Opin. Ther. Patents* (2000) 10 215-230; 30) Inhibitors of phosphatidyl inositoi-3-0H kinase family members including blockers of PI3-kinase, ATM, DNA-PK, and Ku may also be useful in combination with the present disclosure; 31) Antagonists of smoothened receptor (SMO) may also be useful in combination with the present disclosure. Examples of antagonists of smoothened receptor include but are not limited to vismodegib (Erivedge®); 32) Inhibitors of protein translation may also be useful in combination with the present disclosure. Examples of inhibitors of protein translation include but are not limited to omacetaxine mepesuccinate (Synribo®); and 33) anti-cancer agents with other mechanisms of action including miltefosine (Impavido and Miltex), masoprocol, mitoguazone, alitretinoin, mitotane, arsenic trioxide, celecoxib, and anagrelide.

Compounds disclosed herein may also be employed in conjunction with anti-emetic agents to treat nausea or emesis, including acute, delayed, late-phase, and anticipatory emesis, which may result from the use of a compound as disclosed herein, alone or with radiation therapy. For the prevention or treatment of emesis, a compound as disclosed herein may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

A compound as disclosed herein may also be administered with an agent useful in the treatment of anemia. Such an anemia treatment agent is, for example, a continuous erythropoiesis receptor activator (such as epoetin alfa).

A compound as disclosed herein may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound as disclosed herein may also be useful for treating or preventing cancer in combination with siRNA therapeutics.

A compound as disclosed herein may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); Axitinib (Inlyta®); azacitidine (Vidaza®); bevacuzimab (Avastin®); bexarotene capsules (Targretin®); bexarotene gel (Targretin®); bicalutamide (Casodex®), bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); flutamide (Eulexin®), fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); ipilimumab (Yervoy®), irinotecan (Camptosar®); lapatinib (TYKERB®), lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); panitumumab (VECTIBIX®), pamidronate (Aredia®); Pazopanib (Votrient®), pegademase (Adagen (Pegademase Bovine)®); pegaspargase (Oncaspar®); Pegfilgrastim (Neulasta®); pemetrexed disodium (Alimta®); pentostatin (Nipent®); pertuzumab (OMNITARG®, 2C4), pipobroman (Vercyte®); plicamycin, mithramycin (Mithracin®); porfimer sodium (Photofrin®); procarbazine (Matulane®); quinacrine (Atabrine®); Rapamycin (Sirolimus, RAPAMUNE®,), Rasburicase (Elitek®); Rituximab (Rituxan®); rubitecan (Orathecin), ruxolitinib (Jakafi®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vandetanib (ZACTIMA®), vemurafenib (Zelboraf®), vinblastine (Velban®); vincristine (Oncovin®); vinorelbine (Navelbine®); vorinostat (Zolinza®); zoledronate (Zometa®), nilotinib (Tasigna®); and dasatinib (Sprycel®). ARRY-886 (Mek inhibitor, AZD6244), SF-1126 (PI3K inhibitor,), BEZ-235 (PI3K inhibitor), XL-147 (PI3K inhibitor), PTK787/ZK 222584, crizotinib (Xalkori®), and vemurafenib (Zelboraf®).

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating disorders and symptoms relating cancer in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of disorders and symptoms relating to cancer.

The compounds, compositions, and methods disclosed herein are useful for the treatment of disease. In certain embodiments, the diseases is one of dysregulated cellular proliferation, including cancer. The cancer may be hormone-dependent or hormone-resistant, such as in the case of breast cancers. In certain embodiments, the cancer is a solid tumor. In other embodiments, the cancer is a lymphoma or leukemia. In certain embodiments, the cancer is and a drug resistant phenotype of a cancer disclosed herein or known in the art. Tumor invasion, tumor growth, tumor metastasis, and angiogenesis may also be treated using the compositions and methods disclosed herein. Precancerous neoplasias are also treated using the compositions and methods disclosed herein.

Cancers to be treated by the methods disclosed herein include colon cancer, breast cancer, ovarian cancer, lung cancer and prostate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; and thyroid and other endocrine glands. The term "cancer" also encompasses cancers that do not necessarily form solid tumors, including Hodgkin's disease, non-Hodgkin's lymphomas, multiple myeloma and hematopoietic malignancies including leukemias (Chronic Lymphocytic Leukemia (CLL), Acute Lymphocytic Leukemia (ALL)) and lymphomas including lymphocytic, granulocytic and monocytic. Additional types of cancers which may be treated using the compounds and methods of the disclosure include, but are not limited to, adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor.

In certain embodiments, the compositions and methods disclosed herein are useful for preventing or reducing tumor invasion and tumor metastasis.

In certain embodiments, the compositions and methods disclosed herein are useful for preventing or reducing angiogenesis and disorders related to angiogenesis.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Abbreviations $CHCl_3$=chloroform; i-PrOH=isopropanol; $H_2O$=water; DCM=dichloromethane; $Na_2SO_4$=sodium sulfate; $MgSO_4$=magnesium sulfate; EtOAc=ethyl acetate; EtOH=ethanol; $Et_2O$=diethyl ether; THF=tetrahydrofuran; NMP=N-Methyl-2-pyrrolidone; NaOH=sodium hydroxide; MeOH=methanol; $CDCl_3$=deuterated chloroform; HCl=hydrochloric acid; MeCN=acetonitrile; $Cs_2CO_3$=cesium carbonate; DMF=N,N-dimethylformamide; $CD_3OD$=deuterated methanol; DMSO-$d_6$=deuterated dimethyl sulfoxide; DMSO=dimethyl sulfoxide; TFA=trifluoroacetic acid; AcOH=acetic acid; HBr=hydrobromic acid; HCOOH=formic acid; $K_2CO_3$=potassium carbonate; DBU=1,8-diazabicyclo[5.4.0]undec-7-ene; $NaHCO_3$=sodium hydrogen carbonate; KCN=potassium cyanide; TEA=$Et_3N$=triethylamine; DMAP=4-dimethylaminopyridine; $NH_2OH.HCl$=hydroxylammonium chloride; DIEA=N,N-diisopropylethylamine; LiOH=lithium hydroxide;

NH$_4$HCO$_3$=ammonium hydrogen carbonate; NH$_4$OH=ammonium hydroxide; K$_3$PO$_4$=potassium phosphate tribasic; NaOtBu=sodium t-butoxide; CuBr$_2$=copper (II) bromide; CuCl$_2$=copper (II) chloride; CuCN (LiCl)$_2$=Copper(I) cyanide di(lithium chloride) complex; EDC.HCl=1-Ethyl-3-(3-dimethylaminopropyl)carbodiimide hydrochloride; HOBT=1-hydroxybenzotriazole; PyBop=(Benzotriazol-1-yloxy)tripyrrolidinophosphonium hexafluorophosphate; LiCl=lithium chloride; NaI=sodium iodide; NaBr=sodium bromide; N$_2$=nitrogen; Ar=argon; MnO$_2$=manganese dioxide; HATU=2-(1H-7-Azabenzotriazol-1-yl)-1,1,3,3-tetramethyl uronium hexafluorophosphate methanaminium; BH$_3$-THF=borane tetrahydrofuran complex solution; POCl$_3$=phosphorus oxychloride; Ac$_2$O=acetic anhydride; NH$_2$NH$_2$.H$_2$O=hydrazine hydrate; NaBH$_4$=sodium borohydride; NaBH$_3$CN=sodium cyanoborohydride; n-BuLi=n-butyllithium; CH$_3$I=methyl iodide; CS$_2$=carbon disulfide; AIBN=azobisisobutyronitrile; KF=potassium fluoride; Bu$_3$SnH=tributyltin hydride; RuPhos=2-Dicyclohexylphosphino-2',6'-diisopropoxybiphenyl; XPhos=2-Dicyclohexylphosphino-2',4',6'-triisopropylbiphenyl; and Pd$_2$(dba)$_3$=tris(dibenzylideneacetone)dipalladium(0); Pd(Ph$_3$)$_4$=tetrakis(triphenylphosphine)palladium(0); NCS=N-chlorosuccinimide; DEAD=diethyl azodicarboxylate; O$_5$O$_4$=osmium tetraoxide; DIBAL-H=di-iso-butyl aluminum hydride; t-BuOH=tert-butanol; Py=pyridine; NaOMe=sodium methoxide; prep-HPLC=preparative high-performance liquid chromatography.

Compounds

The present disclosure provides a compound of structural Formula I $$(R_1)_n\text{-A-Y}_1\text{—B-D-E-}(R_3)_p\cdot(M)_a\cdot(H_2O)_b \quad (I)$$

wherein: M is selected from an inorganic acid, an organic acid, a basic amino acid, or an acidic amino acid with the proviso that M is not trifluoroacetic acid; a is a fractional or whole number between about 0.5 and about 3.5 inclusive; b is a fractional or whole number between about 0 and about 5 inclusive; n is 0, 1, or 2; p is 0, 1, or 2; q is 0, 1, 2, 3, or 4; u is 0, 1, or 2; A is selected from aryl or heteroaryl; B is selected from

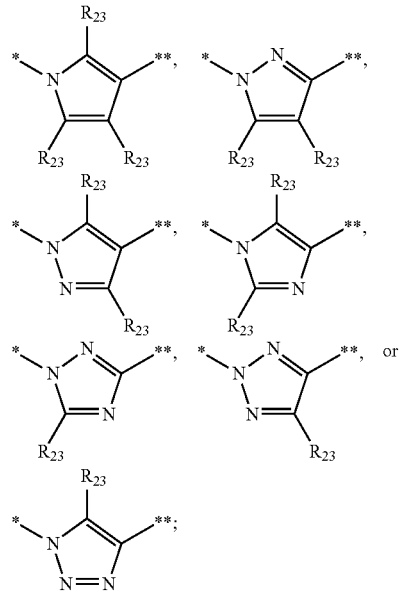

D is selected from alkyl, heteroalkyl, alkoxy, alkylthio, carbonyl, alkylcarbonyl, carboxyl, oxy, thio, sulfinyl, sulfonyl, sulfonamido, amino, amido, alkylamino, or heteroaryl, any of which can be optionally substituted with one or more substituents selected from hydrogen, deuterium, halogen, alkyl, haloalkyl, perhaloalkyl, heteroalkyl, hydroxyalkyl, acyl, cyano, hydroxy, alkoxy, haloalkoxy, perhaloalkoxy, cycloalkyl, aryl, heterocycloalkyl, heteroaryl, or oxo, any of which may be optionally substituted; E is selected from aryl or heteroaryl; G is selected from saturated 3- to 7-membered cycloalkyl or saturated 3- to 7-membered heterocycloalkyl; R$_1$ is selected from —Y$_2$-alkyl-N(R$_4$)R$_5$, hydrogen, deuterium, halogen, alkyl, alkenyl, alkynyl, haloalkyl, perhaloalkyl, heteroalkyl, hydroxyalkyl, aminoalkyl, acyl, carboxylalkyl, carbonyl, carboxyl, cyano, hydroxy, alkoxy, haloalkoxy, perhaloalkoxy, oxo, alkylthio, thiolalkyl, mercaptyl, thiol, sulfonate, sulfonamido, alkylsulfonyl, amino, amido, alkylamino, dialkylamino, carbamate, nitro, cycloalkyl, aryl, heterocycloalkyl, heteroaryl, cycloalkyloxy, aryloxy, heterocycloalkyloxy, heteroaryloxy,

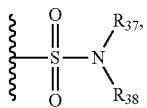

cycloalkylcarbonyl, arylcarbonyl, heterocycloalkylcarbonyl, heteroarylcarbonyl, cycloalkylalkyl, arylalkyl, heterocycloalkylalkyl, heterocycloalkylcarbonylalkyl, or heteroarylalkyl, any of which can be optionally substituted with one or more substituents selected from hydrogen, deuterium, halogen, alkyl, alkenyl, alkynyl, haloalkyl, perhaloalkyl, heteroalkyl, hydroxyalkyl, amidoalkyl, acyl, carbonyl, carboxyl, carboxylalkyl, alkylcarbonyl, heteroalkylcarbonyl, hydroxyalkylcarbonyl, aminoalkylcarbonyl, alkylaminoalkylcarbonyl, alkenylcarbonyl, alkynylcarbonyl, alkoxyalkyl, carboxyl, cyano, hydroxy, alkoxy, haloalkoxy, perhaloalkoxy, oxo, alkylthio, thiol, acylthio, sulfonamido, alkylsulfonyl, amino, amido, carbamate, alkylamino, dialkylamino, alkylaminoalkyl, dialkylaminoalkyl, nitro, trisubstituted silyl, trisubstituted siloxy, cycloalkyl, aryl, heterocycloalkyl, heteroaryl, alkylheterocycloalkyl, any of which may be optionally substituted; R$_3$ is selected from hydrogen, deuterium, halogen, alkyl, haloalkyl, perhaloalkyl, heteroalkyl, hydroxyalkyl, alkoxyalkyl, aminoalkyl, acyl, carbonyl, carboxyl, cyano, cyanoalkyl, hydroxy, alkoxy, haloalkoxy, perhaloalkoxy, alkoxyalkoxy, hydroxyalkoxy, oxo, alkylthio, mercaptyl, thiol, haloalkylthio, perhaloalkylthio, cyanoalkylthio, haloalkylsulfonyl, alkylsulfonyl, alkoxyalkylsulfonyl, cyanoalkylsulfonyl, sulfonate, sulfonamido, amino, amido, alkylamino, dialkylamino, carbamate, nitro, cycloalkyl, aryl, heterocycloalkyl, heteroaryl, cycloalkyloxy, aryloxy, heterocycloalkyloxy, heteroaryloxy, cycloalkylalkyl, arylalkyl, heterocycloalkylalkyl, or heteroarylalkyl, trisubstituted silyl, —SF$_5$, —(C(R$_{31}$)(R$_{32}$))$_u$—O-alkyl, —(C(R$_{31}$)(R$_{32}$))$_u$—O-cycloalkyl, —S(O)$_u$-alkyl, —S(O)$_u$-cycloalkyl, cycloalkylthio, —CF$_3$, —OCF$_3$, —(C(R$_{31}$)(R$_{32}$))$_u$—OCF$_3$, saturated heterocycloalkyloxy, —(C(R$_{31}$)(R$_{32}$))$_u$—O-saturated heterocycloalkyl, —(C(R$_{31}$)(R$_{32}$))$_u$— saturated heterocycloalkyl, saturated heterocycloalkylthio, —S(O)$_u$-saturated heterocycloalkyl, —(C(R$_{31}$)(R$_{32}$))$_u$—OCF$_3$,

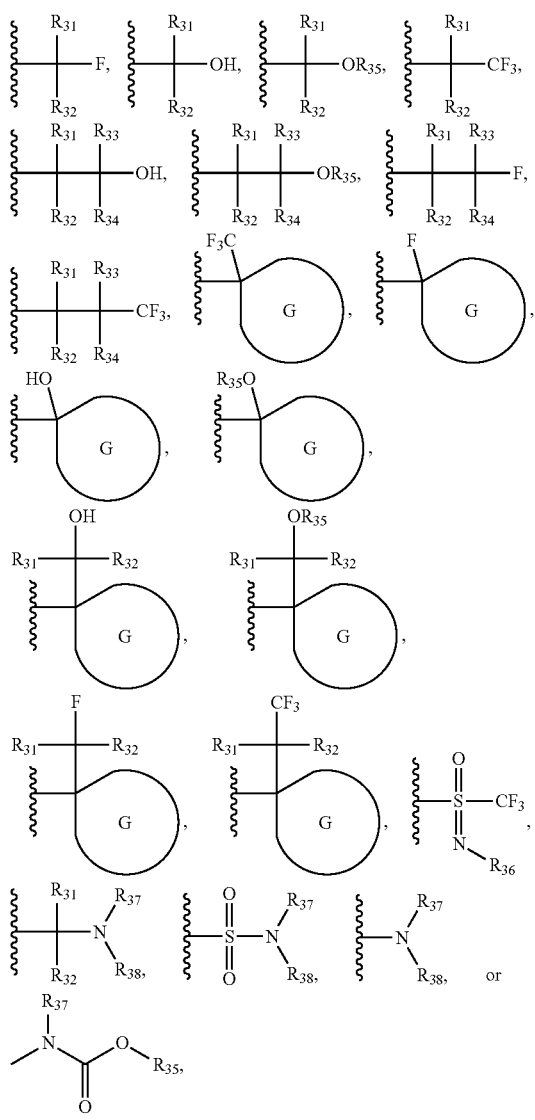

any of which may be optionally substituted; $R_4$ and $R_5$ are independently selected from hydrogen, deuterium, alkyl, alkenyl, alkynyl, haloalkyl, perhaloalkyl, heteroalkyl, hydroxyalkyl, acyl, carbonyl, carboxyl, alkoxy, haloalkoxy, perhaloalkoxy, alkylsulfonyl, sulfonamido, amido, cycloalkyl, aryl, heterocycloalkyl, heteroaryl, cycloalkylalkyl, arylalkyl, heterocycloalkylalkyl, or heteroarylalkyl, or $R_4$ and $R_5$, taken together, form a heterocyloalkyl or heteroaryl, any of which can be optionally substituted with one or more substituents selected from hydrogen, deuterium, halogen, alkyl, alkenyl, alkynyl, haloalkyl, perhaloalkyl, heteroalkyl, hydroxyalkyl, acyl, carbonyl, carboxyl, cyano, hydroxy, alkoxy, haloalkoxy, perhaloalkoxy, oxo, alkylthio, mercaptyl, thiol, sulfonate, sulfonamido, amino, amido, alkylamino, dialkylamino, carbamate, nitro, cycloalkyl, aryl, heterocycloalkyl, heteroaryl, cycloalkyloxy, aryloxy, heterocycloalkyloxy, heteroaryloxy, cycloalkylalkyl, arylalkyl, heterocycloalkylalkyl, or heteroarylalkyl, any of which may be optionally substituted; each $R_{23}$ is independently selected from hydrogen, deuterium, halogen, alkyl, haloalkyl, perhaloalkyl, heteroalkyl, hydroxyalkyl, aminoalkyl, acyl, carbonyl, carboxyl, cyano, hydroxy, alkoxy, haloalkoxy, perhaloalkoxy, oxo, alkylthio, amino, alkylamino, dialkylamino, nitro, cycloalkyl, aryl, or heteroaryl, any of which may be optionally substituted; $R_{31}$, $R_{32}$, $R_{33}$, $R_{34}$, and $R_{36}$ are independently selected from hydrogen, deuterium, alkyl, or perfluoroalkyl, any of which can be optionally substituted; $R_{35}$ is selected from hydrogen, deuterium, alkyl, perfluoroalkyl, cycloalkyl, or saturated heterocycloalkyl, any of which can be optionally substituted; $R_{37}$ and $R_{38}$ are independently selected from alkyl or perfluoroalkyl, or $R_{37}$ and $R_{38}$, taken together, form a heterocyloalkyl, any of which can be optionally substituted; $Y_1$ is selected from alkyl, alkenyl, alkynyl, heteroalkyl, alkoxy, alkylthio, carbonyl, alkylcarbonyl, carboxyl, oxy, thio, sulfinyl, sulfonyl, sulfonamido, amino, amido, alkylamino, or carbamate, any of which can be optionally substituted with one or more substituents selected from hydrogen, deuterium, halogen, alkyl, haloalkyl, perhaloalkyl, heteroalkyl, hydroxyalkyl, aminoalkyl, acyl, carbonyl, carboxyl, cyano, hydroxy, alkoxy, haloalkoxy, perhaloalkoxy, oxo, alkylthio, amino, alkylamino, dialkylamino, or cycloalkyl, any of which may be optionally substituted; $Y_2$ is selected from a bond, carbonyl, alkylcarbonyl, carboxyl, oxy, thio, sulfinyl, sulfonyl, sulfonamido, amino, amido, alkylamino, or carbamate, any of which can be optionally substituted with one or more substituents selected from hydrogen, deuterium, halogen, alkyl, alkenyl, alkynyl, haloalkyl, perhaloalkyl, heteroalkyl, hydroxyalkyl, acyl, carbonyl, carboxyl, cyano, hydroxy, alkoxy, haloalkoxy, perhaloalkoxy, oxo, alkylthio, mercaptyl, thiol, sulfonate, sulfonamido, amino, amido, alkylamino, dialkylamino, carbamate, cycloalkyl, aryl, heterocycloalkyl, heteroaryl, cycloalkyloxy, aryloxy, heterocycloalkyloxy, heteroaryloxy, cycloalkylalkyl, arylalkyl, heterocycloalkylalkyl, or heteroarylalkyl, any of which may be optionally substituted; if A is phenyl, B is not

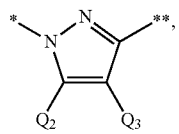

wherein $Q_2$ or $Q_3$ are freely substituted; if A is phenyl or pyridyl, $Y_1$ is $CH_2$, B is

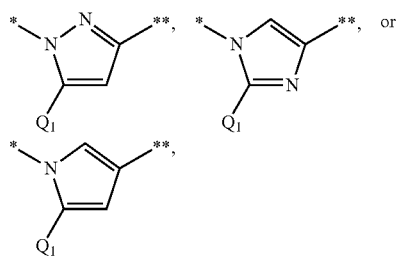

and $Q_1$ is methyl, ethyl, or trifluoromethyl, then D is not

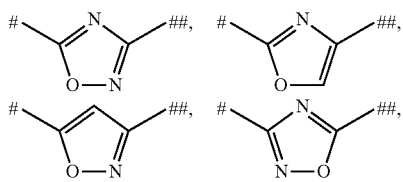

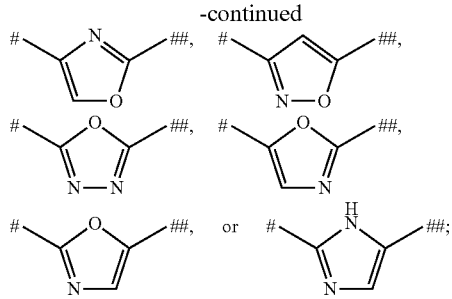

and wherein * represents the point of attachment to $Y_1$ and ** represents the point of attachment to D, and # represents the point of attachment to B and ## represents the point of attachment to E.

In some embodiments, A is selected from aryl or mono- or bicyclic heteroaryl; B is selected from

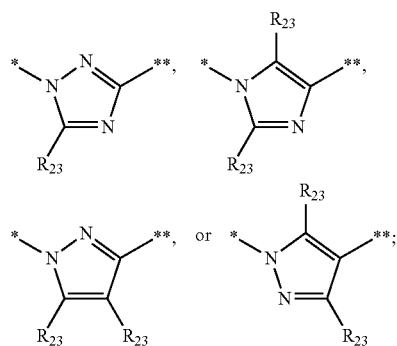

D is selected from amido, 5-membered heteroaryl, or 6-membered heteroaryl, any of which can be optionally substituted with one or more substituents selected from hydrogen, deuterium, halogen, alkyl, haloalkyl, perhaloalkyl, heteroalkyl, hydroxyalkyl, acyl, cyano, hydroxy, alkoxy, haloalkoxy, perhaloalkoxy, cycloalkyl, aryl, heterocycloalkyl, heteroaryl, or oxo, any of which may be optionally substituted; E is selected from phenyl, 5-membered heteroaryl, 6-membered heteroaryl, or 9-membered bicyclic heteroaryl; $R_4$ and $R_5$ are independently selected from hydrogen, deuterium, alkyl, alkenyl, alkynyl, haloalkyl, perhaloalkyl, heteroalkyl, hydroxyalkyl, acyl, carbonyl, carboxyl, alkoxy, haloalkoxy, perhaloalkoxy, alkylsulfonyl, sulfonamido, amido, cycloalkyl, aryl, heterocycloalkyl, heteroaryl, cycloalkylalkyl, arylalkyl, heterocycloalkylalkyl, or heteroarylalkyl, or $R_4$ and $R_5$, taken together, form a heterocyloalkyl or heteroaryl, any of which can be optionally substituted with one or more substituents selected from hydrogen, deuterium, halogen, alkyl, haloalkyl, perhaloalkyl, heteroalkyl, hydroxyalkyl, acyl, carbonyl, carboxyl, cyano, hydroxy, alkoxy, haloalkoxy, perhaloalkoxy, oxo, alkylthio, mercaptyl, thiol, sulfonamido, amino, amido, alkylamino, dialkylamino, carbamate, or cycloalkyl, any of which may be optionally substituted; $R_{23}$ is selected from hydrogen, deuterium, halogen, alkyl, haloalkyl, perhaloalkyl, heteroalkyl, hydroxyalkyl, cyano, hydroxy, alkoxy, haloalkoxy, perhaloalkoxy, alkylthio, amino, alkylamino, dialkylamino, cycloalkyl, aryl, or heteroaryl; $Y_1$ is alkyl, which can be optionally substituted with one or more substituents selected from hydrogen, deuterium, alkyl, cycloalkyl, or halogen; and $Y_2$ is selected from a bond, carbonyl, alkylcarbonyl, carboxyl, oxy, thio, sulfinyl, sulfonyl, sulfonamido, amino, amido, alkylamino, or carbamate, any of which can be optionally substituted with one or more substituents selected from hydrogen, deuterium, halogen, alkyl, haloalkyl, perhaloalkyl, heteroalkyl, hydroxyalkyl, acyl, carbonyl, carboxyl, cyano, hydroxy, alkoxy, haloalkoxy, perhaloalkoxy, oxo, alkylthio, mercaptyl, thiol, sulfonamido, amino, amido, alkylamino, dialkylamino, carbamate, or cycloalkyl, any of which may be optionally substituted.

In particular embodiments, B is

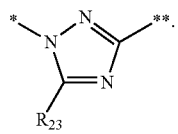

In some embodiments, D is selected from —C(=O)NR$_{11}$—, 5-membered heteroaryl, or 6-membered heteroaryl; E is selected from phenyl, pyrimidine, 1,3-benzodioxol, indole, or 1-benzofuran; $R_1$ is selected from —Y$_2$-alkyl-N(R$_4$)R$_5$, hydrogen, deuterium, halogen, alkyl, alkenyl, haloalkyl, perhaloalkyl, heteroalkyl, hydroxyalkyl, aminoalkyl, acyl, carboxylalkyl, carbonyl, carboxyl, cyano, hydroxy, alkoxy, haloalkoxy, perhaloalkoxy, oxo, alkylthio, thiolalkyl, sulfonamido, alkylsulfonyl, amino, amido, alkylamino, dialkylamino, nitro, cycloalkyl, aryl, heterocycloalkyl, heteroaryl, cycloalkyloxy, aryloxy, heterocycloalkyloxy, heteroaryloxy,

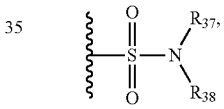

cycloalkylcarbonyl, arylcarbonyl, heterocycloalkylcarbonyl, or heterocycloalkylcarbonylalkyl, any of which can be optionally substituted with one or more substituents selected from hydrogen, deuterium, halogen, alkyl, alkenyl, alkynyl, amidoalkyl, acyl, carboxylalkyl, alkylcarbonyl, heteroalkylcarbonyl, hydroxyalkylcarbonyl, aminoalkylcarbonyl, alkylaminoalkylcarbonyl, alkenylcarbonyl, alkynylcarbonyl, haloalkyl, perhaloalkyl, heteroalkyl, hydroxyalkyl, alkoxyalkyl, carboxyl, cyano, hydroxy, alkoxy, haloalkoxy, perhaloalkoxy, oxo, thiol, acylthio, sulfonamido, alkylsulfonyl, amino, amido, carbamate, alkylamino, dialkylamino, alkylaminoalkyl, dialkylaminoalkyl, trisubstituted silyl, trisubstituted siloxy, cycloalkyl, aryl, heterocycloalkyl, heteroaryl, alkylheterocycloalkyl, any of which may be optionally substituted; $R_3$ is selected from hydrogen, deuterium, halogen, alkyl, haloalkyl, perhaloalkyl, heteroalkyl, hydroxyalkyl, alkoxyalkyl, aminoalkyl, dialkylamino, acyl, carbonyl, carboxyl, cyano, cyanoalkyl, hydroxy, alkoxy, haloalkoxy, perhaloalkoxy, alkoxyalkoxy, hydroxyalkoxy, oxo, alkylthio, haloalkylthio, perhaloalkylthio, cyanoalkylthio, alkylsulfonyl, alkoxyalkylsulfonyl, cyanoalkylsulfonyl, haloalkylsulfonyl, sulfonamido, alkylsulfonamido, amino, alkylamino, dialkylamino, amido, cycloalkyl, aryl, heterocycloalkyl, heteroaryl perhaloalkylcycloalkyl, hydroxyheterocycloalkyl, hydroxycycloalkyl, heterocycloalkylcarbonyl, or heterocycloalkylalkyl, any of which can be optionally substituted; $R_{11}$ is selected from hydrogen, deuterium, alkyl, haloalkyl, perhaloalkyl, heteroalkyl, hydroxyalkyl, cycloalkyl, aryl, heterocycloalkyl, or heteroaryl, any of which may be optionally substituted; $Y_1$ is —$CH_2$—; and $Y_2$ is selected from a bond, carbonyl, amino, or alkylamino.

In some embodiments, A is selected from phenyl, 5-membered heteroaryl, or 6-membered heteroaryl; E is phenyl; $R_1$ is selected from —$Y_2$-alkyl-N($R_4$)$R_5$, hydrogen, deuterium, halogen, alkyl, alkenyl, haloalkyl, perhaloalkyl, heteroalkyl, hydroxyalkyl, acyl, carboxylalkyl, carboxyl, carbonyl, cyano, hydroxy, alkoxy, haloalkoxy, perhaloalkoxy, oxo, thiolalkyl, sulfonyl, sulfonamido, alkylsulfonyl, amino, amido, alkylamino, dialkylamino, nitro, heterocycloalkyl, heterocycloalkyloxy,

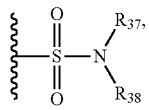

heterocycloalkylcarbonylalkyl, or heterocycloalkylcarbonyl, any of which can be optionally substituted with one or more substituents selected from hydrogen, deuterium, halogen, alkyl, alkenyl, amidoalkyl, acyl, carboxylalkyl, hydroxyalkylcarbonyl, alkynylcarbonyl, heteroalkyl, hydroxyalkyl, alkoxyalkyl, carboxyl, cyano, hydroxy, alkoxy, oxo, sulfonamido, alkylsulfonyl, amino, amido, carbamate, dialkylamino, dialkylaminoalkyl, trisubstituted siloxy, cycloalkyl, heterocycloalkyl, alkylheterocycloalkyl, any of which may be optionally substituted; $R_{11}$ is selected from hydrogen, deuterium, alkyl, or cycloalkyl, any of which may be optionally substituted; and each $R_{23}$ is independently selected from hydrogen, deuterium, hydroxyl, alkyl, haloalkyl, perhaloalkyl, cyano, saturated 3- to 6-membered cycloalkyl, 4- to 6-membered heterocycloalkyl, or 5- to 6-membered heteroaryl.

In particular embodiments, n is 1; p is 1; and $R_{23}$ is selected from alkyl, haloalkyl, perhaloalkyl, hydroxy, or cyclopropyl.

In some embodiments, the compound has structural Formula II

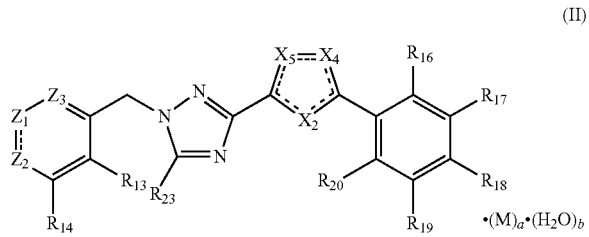

wherein: M is selected from the group consisting of an inorganic acid, an organic acid, a amino acid; with the proviso that M is not trifluoroacetic acid; a is a fractional or whole number between about 0.5 and about 3.5 inclusive; b is a fractional or whole number between about 0 and about 10 inclusive;

$X_2$, $X_4$, and $X_5$ are independently selected from $CR_{21}$, N, O, or S, and wherein $X_2$, $X_4$, and $X_5$, taken together, form a 5-membered heteroaryl; $Z_1$ and $Z_2$ are independently selected from N, $NR_1$, C=O, or $CR_1$; $Z_3$ is selected from N, $NR_{12}$, C=O, or $CR_{12}$; $R_1$ is selected from —$Y_2$-alkyl-N($R_4$)$R_5$, hydrogen, deuterium, halogen, alkyl, alkenyl, haloalkyl, perhaloalkyl, heteroalkyl, hydroxyalkyl, aminoalkyl, acyl, carboxylalkyl, carbonyl, carboxyl, carbonyl, cyano, hydroxy, alkoxy, haloalkoxy, perhaloalkoxy, oxo, alkylthio, thiolalkyl, sulfonyl, sulfonamido, alkylsulfonyl, amino, amido, alkylamino, dialkylamino, nitro, cycloalkyl, aryl, heterocycloalkyl, heteroaryl, cycloalkyloxy, aryloxy, heterocycloalkyloxy, heteroaryloxy,

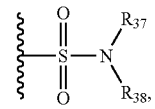

cycloalkylcarbonyl, arylcarbonyl, heterocycloalkylcarbonyl, or heterocycloalkylcarbonylalkyl, any of which can be optionally substituted with one or more substituents selected from hydrogen, deuterium, halogen, alkyl, alkenyl, alkynyl, amidoalkyl, acyl, carboxylalkyl, alkylcarbonyl, heteroalkylcarbonyl, hydroxyalkylcarbonyl, aminoalkylcarbonyl, alkylaminoalkylcarbonyl, alkenylcarbonyl, alkynylcarbonyl, haloalkyl, perhaloalkyl, heteroalkyl, hydroxyalkyl, alkoxyalkyl, carboxyl, cyano, hydroxy, alkoxy, haloalkoxy, perhaloalkoxy, oxo, thiol, acylthio, sulfonamido, alkylsulfonyl, amino, amido, carbamate, alkylamino, dialkylamino, alkylaminoalkyl, dialkylaminoalkyl, trisubstituted silyl, trisubstituted siloxy, cycloalkyl, aryl, heterocycloalkyl, heteroaryl, alkylheterocycloalkyl, any of which may be optionally substituted; $R_{12}$, $R_{13}$, or $R_{14}$ are independently selected from hydrogen, deuterium, halogen, alkyl, haloalkyl, perhaloalkyl, cyano, hydroxy, alkoxy, haloalkoxy, perhaloalkoxy, alkylthio, amino, or saturated 3- to 7-membered cycloalkyl, any of which may be optionally substituted; $R_{16}$, $R_{19}$, or $R_{20}$ are independently selected from hydrogen, deuterium, halogen, alkyl, haloalkyl, perhaloalkyl, cyano, hydroxy, alkoxy, haloalkoxy, perhaloalkoxy, alkylthio, amino, or cycloalkyl, any of which may be optionally substituted; $R_{17}$ or $R_{18}$ are independently selected from hydrogen, deuterium, halogen, alkyl, haloalkyl, perhaloalkyl, heteroalkyl, hydroxyalkyl, alkoxyalkyl, aminoalkyl, dialkylamino, acyl, carbonyl, carboxyl, cyano, cyanoalkyl, hydroxy, alkoxy, haloalkoxy, perhaloalkoxy, alkoxyalkoxy, hydroxyalkoxy, oxo, alkylthio, haloalkylthio, perhaloalkylthio, cyanoalkylthio, alkylsulfonyl, alkoxyalkylsulfonyl, cyanoalkylsulfonyl, haloalkylsulfonyl, sulfonamido, alkylsulfonamido, amino, alkylamino, dialkylamino, amido, cycloalkyl, aryl, heterocycloalkyl, heteroaryl perhaloalkylcycloalkyl, hydroxyheterocycloalkyl, hydroxycycloalkyl, heterocycloalkylcarbonyl, or heterocycloalkylalkyl, any of which can be optionally substituted; $R_{21}$ is selected from null, hydrogen, deuterium, halogen, alkyl, haloalkyl, perhaloalkyl, heteroalkyl, hydroxyalkyl, cyano, hydroxy, alkoxy, haloalkoxy, perhaloalkoxy, alkylthio, amino, alkylamino, or dialkylamino; and $R_{23}$ is selected from hydrogen, deuterium, hydroxyl, alkyl, haloalkyl, perhaloalkyl, cyano, saturated 3- to 6-membered cycloalkyl, 4- to 6-membered heterocycloalkyl, or 5- to 6-membered heteroaryl.

In particular embodiments, two of $X_2$, $X_4$, and $X_5$ are N; and one of $X_2$, $X_4$, and $X_5$ is O; or one of $X_2$, $X_4$, and $X_5$ is N; one of $X_2$, $X_4$, and $X_5$ is O; and one of $X_2$, $X_4$, and $X_5$ is CH; and $R_{23}$ is selected from hydrogen, deuterium, hydroxyl, alkyl, haloalkyl, perhaloalkyl, cyano, or saturated 3- to 6-membered cycloalkyl.

In particular embodiments, $R_1$ is selected from hydrogen, deuterium, fluorine, bromine, cyano, methyl, isopropyl,

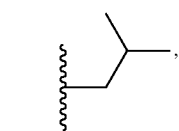
ethylene,
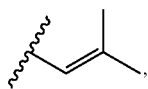
trifluoromethyl, bromomethyl, hydroxymethyl, difluoromethoxy, methoxy, ethoxy, isopropoxy, hydroxy, nitro, acetyl, carboxyl, —CO$_2$CH$_3$,
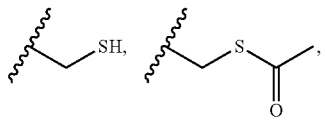
—SO$_2$CH$_3$, —SO$_2$CH$_2$CH$_3$, SO$_2$CH$_2$CH$_2$CH$_3$, —SO$_2$NH$_2$,
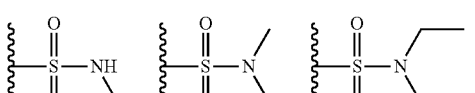
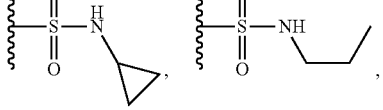
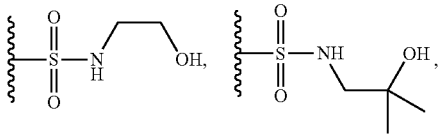
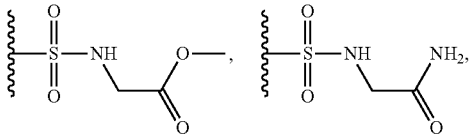
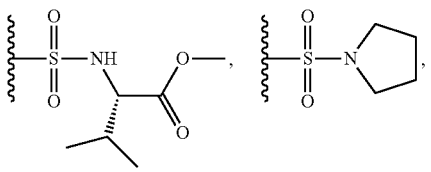
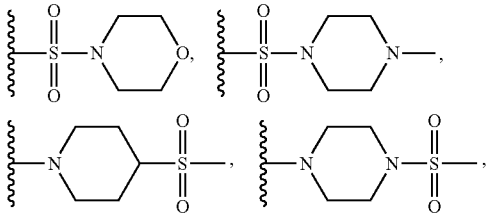
-continued
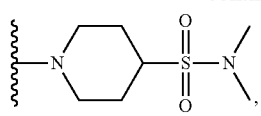
amino, methylamino, dimethylamino,
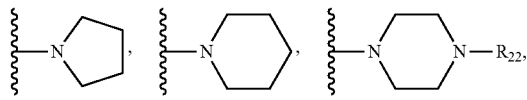
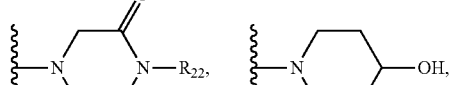
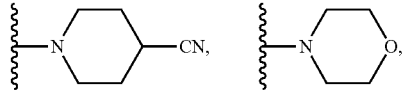
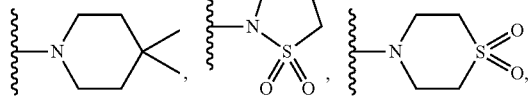
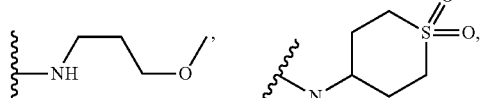
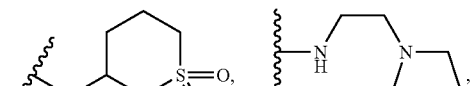
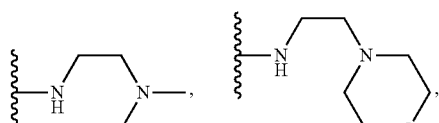
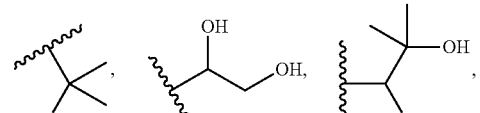
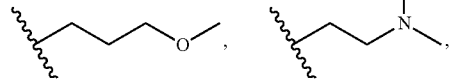
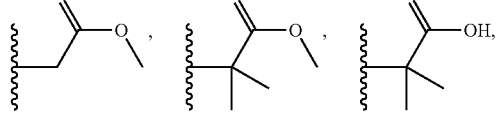
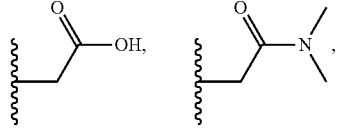

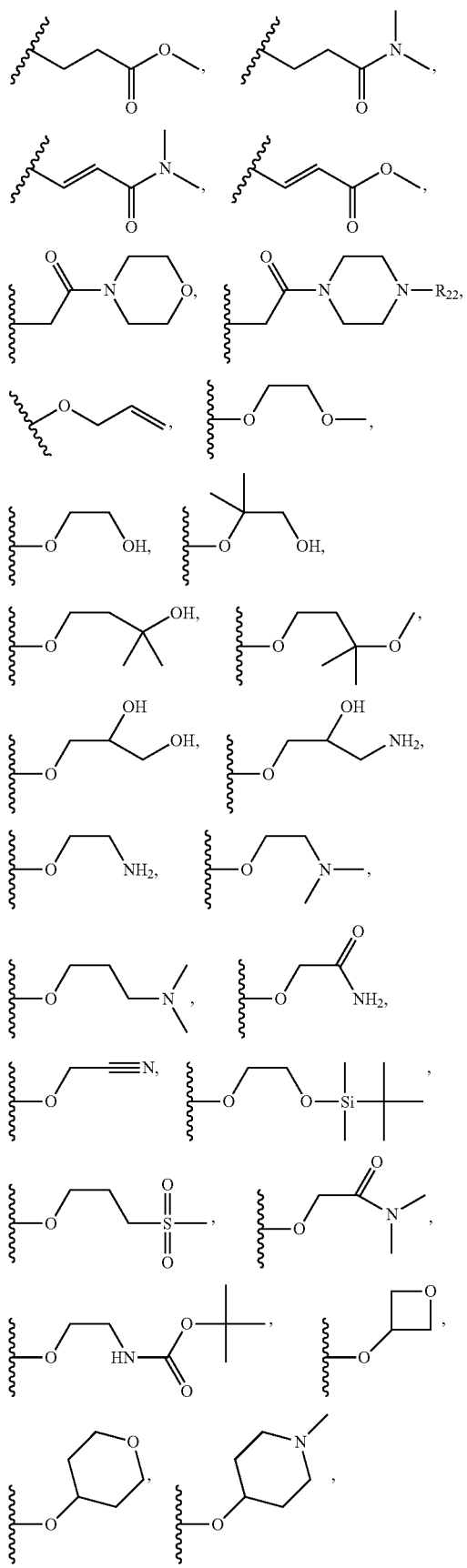
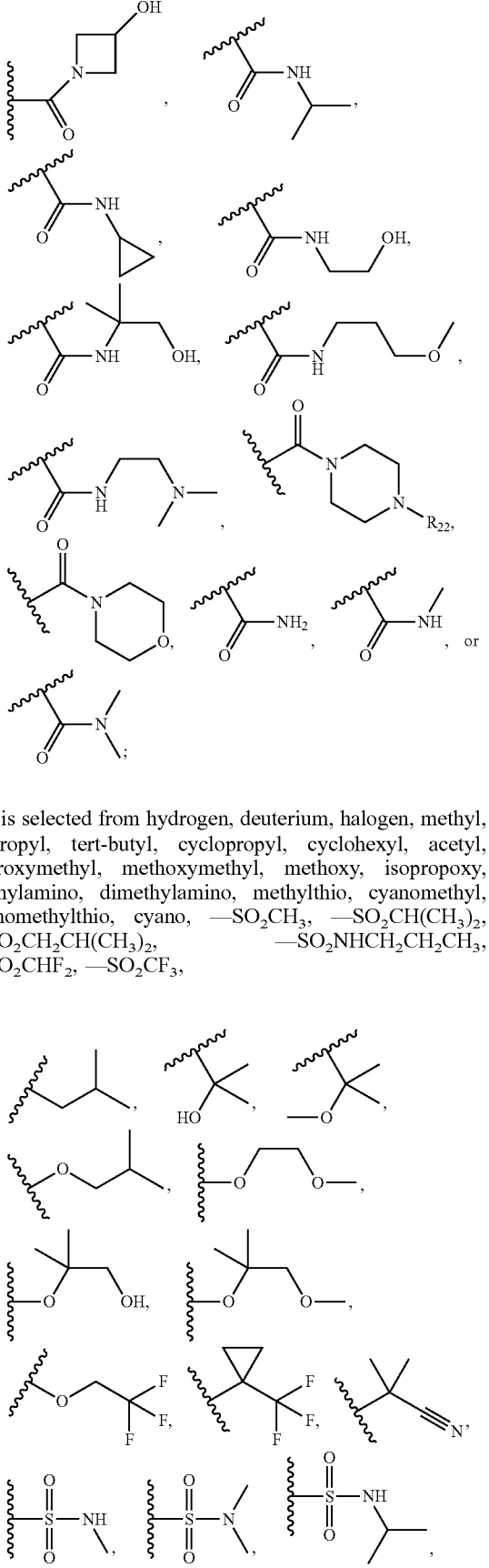
$R_{18}$ is selected from hydrogen, deuterium, halogen, methyl, isopropyl, tert-butyl, cyclopropyl, cyclohexyl, acetyl, hydroxymethyl, methoxymethyl, methoxy, isopropoxy, methylamino, dimethylamino, methylthio, cyanomethyl, cyanomethylthio, cyano, —SO$_2$CH$_3$, —SO$_2$CH(CH$_3$)$_2$, —SO$_2$CH$_2$CH(CH$_3$)$_2$, —SO$_2$NHCH$_2$CH$_2$CH$_3$, —SO$_2$CHF$_2$, —SO$_2$CF$_3$,

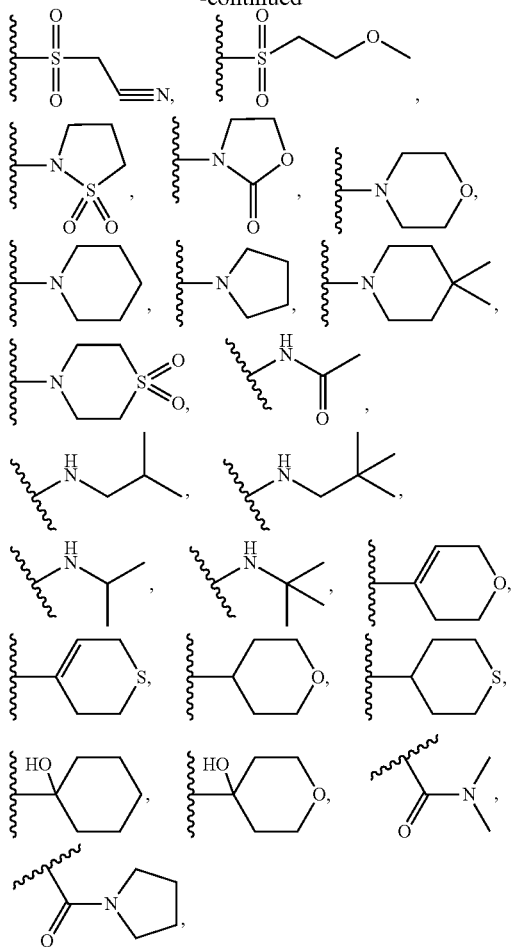

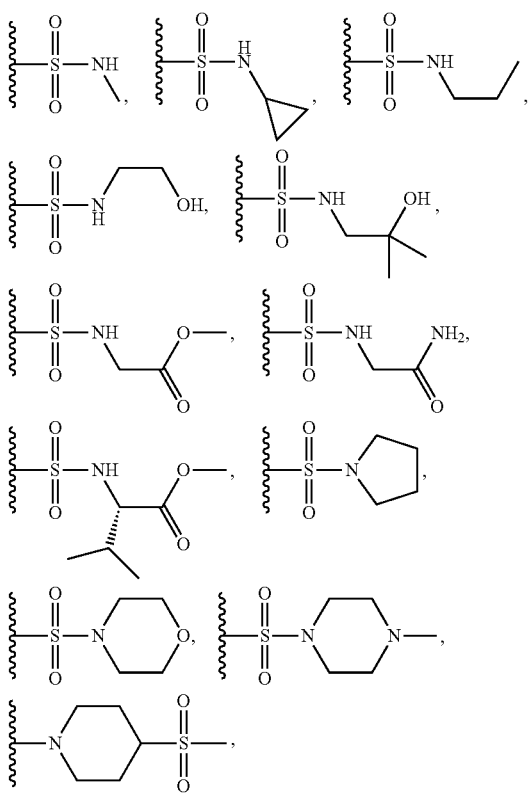

trifluoromethyl, trifluoromethylthio, difluoromethoxy, or trifluoromethoxy; $R_{22}$ is selected from hydrogen, deuterium, methyl, acetyl,

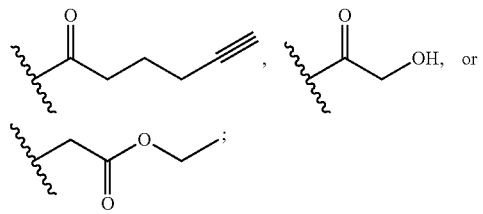

and $R_{23}$ is selected from hydrogen, deuterium, methyl, ethyl, 3-pyridyl, or cyclopropyl In particular embodiments, $R_1$ is selected from hydrogen, halogen, cyano, methyl, isopropyl,

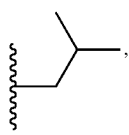

ethylene, trifluoromethyl, difluoromethoxy, methoxy, ethoxy, isopropoxy, hydroxy, carboxyl, —$CO_2CH_3$, —$SO_2CH_3$, —$SO_2NH_2$, amino, methylamino, dimethylamino,

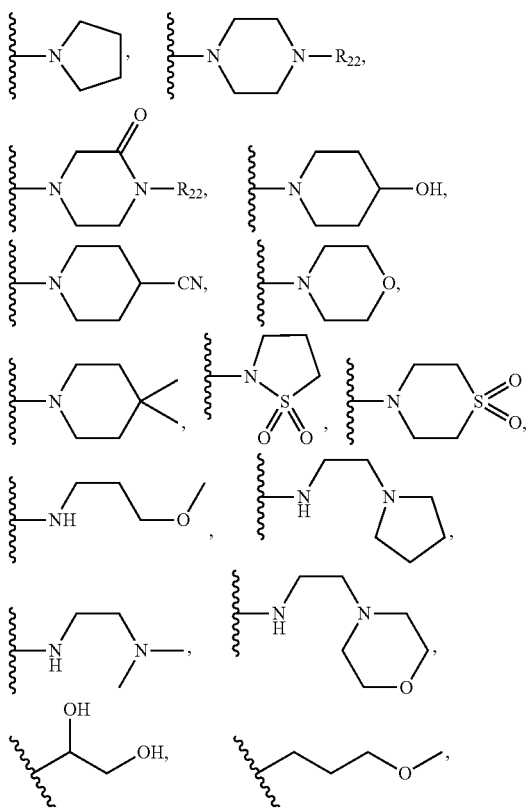

-continued

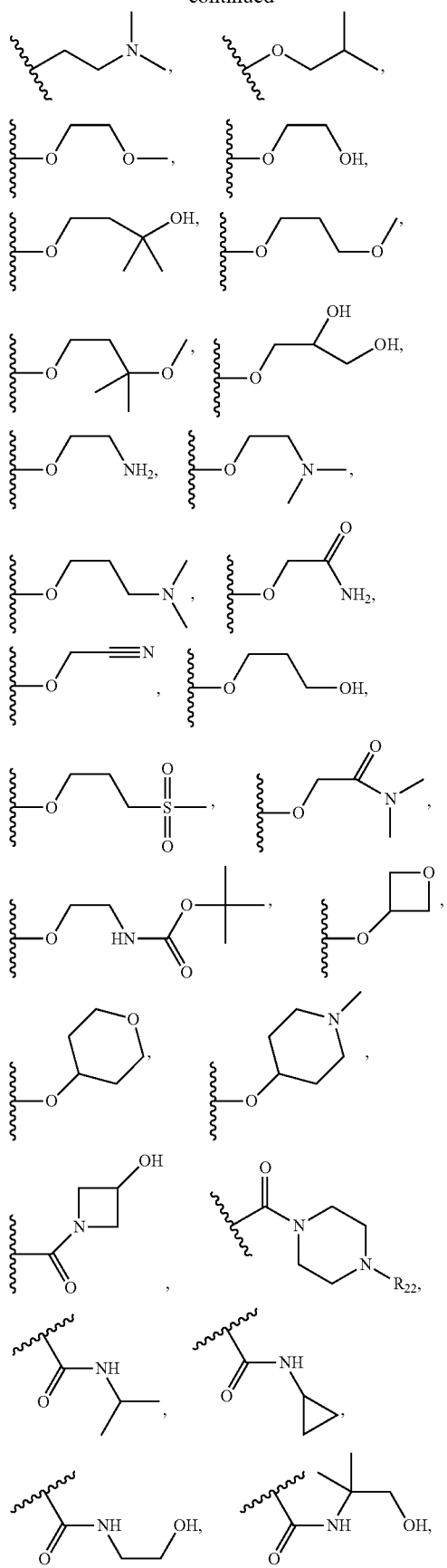
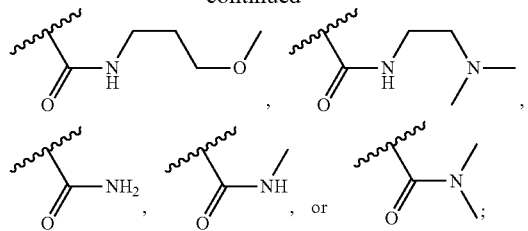

and R$_{23}$ is methyl.

In particular embodiments, two of X$_2$, X$_4$, and X$_5$ are N; and one of X$_2$, X$_4$, and X$_5$ is O.

In particular embodiments, one of X$_2$, X$_4$, and X$_5$ is N; one of X$_2$, X$_4$, and X$_5$ is O; and one of X$_2$, X$_4$, and X$_5$ is CH.

In some embodiments, the compound has structural Formula III:

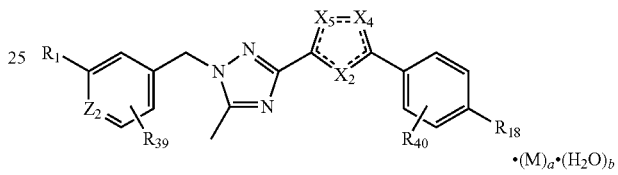

(III)

wherein: M is selected from the group consisting of an inorganic acid, an organic acid, an amino acid; with the proviso that M is not trifluoroacetic acid; a is a fractional or whole number between about 0.5 and about 3.5 inclusive; b is a fractional or whole number between about 0 and about 10 inclusive; X$_2$ and X$_4$ are N and X$_5$ is O; X$_4$ and X$_5$ are N and X$_2$ is O; X$_2$ and X$_5$ are N and X$_4$ is O; X$_2$ is CH, X$_4$ is N, and X$_5$ is O; or X$_2$ is CH, X$_4$ is O, and X$_5$ is N; Z$_2$ is selected from N or CR$_{14}$; R$_1$ is selected from heterocycloalkyl, alkoxyalkoxy, alkylsulfonylalkoxy, heterocycloalkyloxy, heterocycloalkylcarbonyl, alkoxyalkylamido, heterocycloalkylsulfonyl, alkoxyalkylsulfonamido, wherein said heterocycloalkyl, heterocycloalkyloxy, heterocycloalkylcarbonyl, or heterocycloalkylsulfonyl can be optionally substituted with one or more substituents selected from the group consisting hydrogen, alkyl, or oxo; R$_{14}$, R$_{39}$, and R$_{40}$ are independently selected from hydrogen, deuterium, halogen, alkyl, haloalkyl, perhaloalkyl, cyano, hydroxy, alkoxy, haloalkoxy, perhaloalkoxy, alkylthio, amino, or saturated 3- to 7-membered cycloalkyl, any of which may be optionally substituted; or R$_{18}$ is selected from alkyl, haloalkyl, perhaloalkyl, alkoxy, haloalkoxy, perhaloalkoxy, alkylthio, haloalkylthio, or perhaloalkylthio.

In some embodiments, M has a pKa of less than about 2.4.

In certain embodiments, R$_1$ is selected from

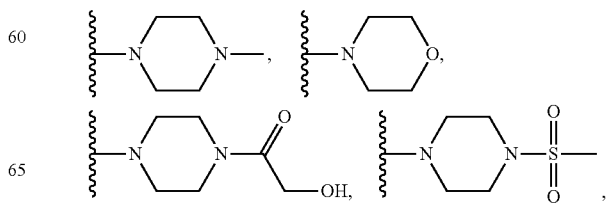

-continued

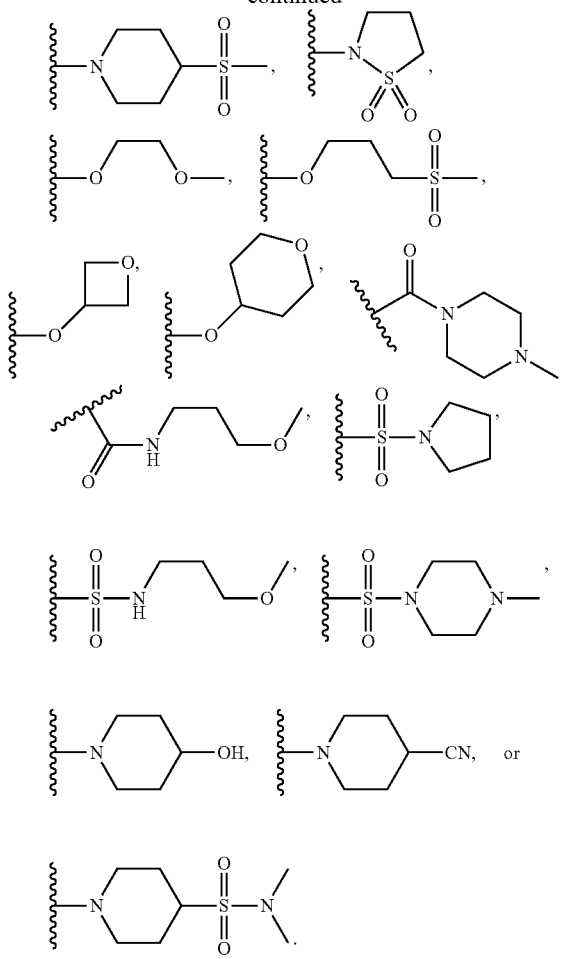

In particular embodiments, $R_{18}$ is selected from isopropyl, tert-butyl, —$CF_3$, —$OCF_3$, —$OCHF_2$, or —$SCF_3$.

In particular embodiments, $R_1$ is selected from

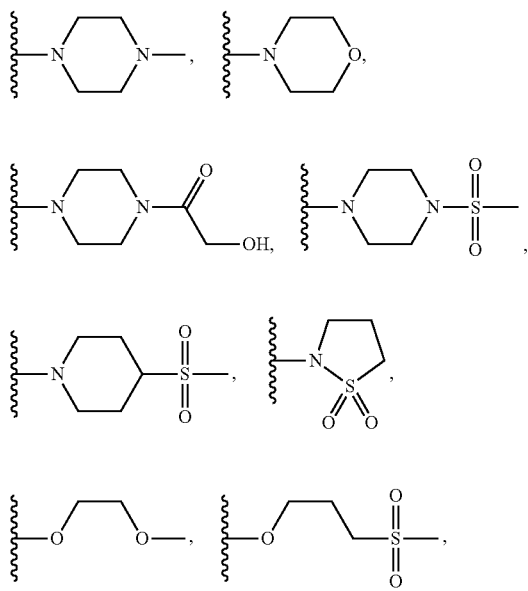

-continued

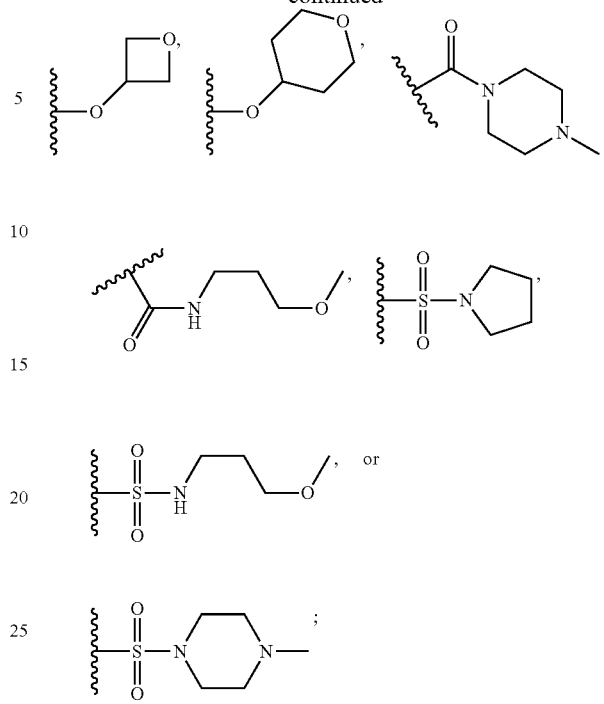

$R_{13}$, $R_{14}$, $R_{16}$, $R_{17}$, and $R_{19}$ are hydrogen; and $R_{18}$ is selected from isopropyl, tert-butyl, —$CF_3$, —$OCF_3$, —$OCHF_2$, or —$SCF_3$.

In certain embodiments, the compound is in a solid form. In particular embodiments, the compound is in a crystalline form.

In some embodiments, M is selected from hydrochloric acid, hydroboric acid, nitric acid, sulfuric acid, phosphoric acid, lactic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, or p-toluenesulfonic acid, glycine, aspartic acid or glutamic acid. In certain embodiments, M is selected from hydrochloric acid, benzenesulfonic acid, or methanesulfonic acid.

In some embodiments, M has a pKa of less than about 2.4.

In some embodiments, a equals 1 and M is hydrochloric acid

In some embodiments, a equals 1 and M is benzenesulfonic acid.

In some embodiments, a equals 1 and M is methanesulfonic acid.

In some embodiments, the compound is 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole hydrochloride; 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole 2,2,2-trifluoroacetate; 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole methanesulfonate; or 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole benzenesulfonate.

In some embodiments, the compound has structural Formula V

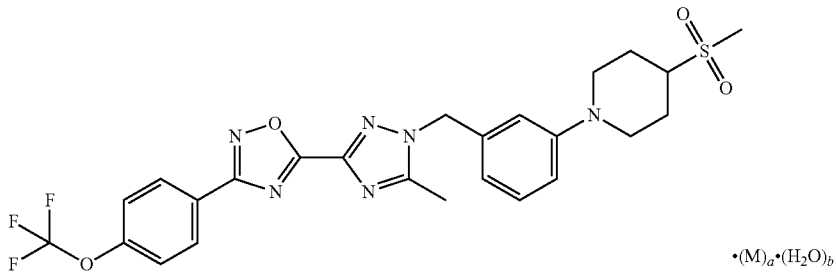

wherein M is selected from (+)-camphor-10-sulfonic acid, 2,2-dichloroacetic acid, 2-hydroxyethanesulfonic acid, acetic acid, aspartic acid, benzenesulfonic acid, citric acid, cyclamic acid, di(tert-butyl) naphthalenesulfonic acid, dodecylsulfonic acid, ethanesulfonic acid, formic acid, fumaric acid, glutamic acid, glycerophosphoric acid, glycine, hydroboric acid, hydrobromic acid, hydrochloric acid, lactic acid, maleic acid, malic acid, methanesulfonic acid, naphthalene-2-sulfonic acid, nitric acid, oxalic acid, phosphoric acid, p-toluenesulfonic acid, pyruvic acid, saccharine, succinic acid, sulfuric acid, tartaric acid, and thiocyanic acid; a is a fractional or whole number between about 0.5 and about 3.5 inclusive; and b is a fractional or whole number between about 0 and about 10 inclusive.

In some embodiments, b is a fractional or whole number between about 0 and about 5 inclusive.

A compound of Formula V

In some embodiments, b is a fractional or whole number between about 0 and about 5 inclusive.

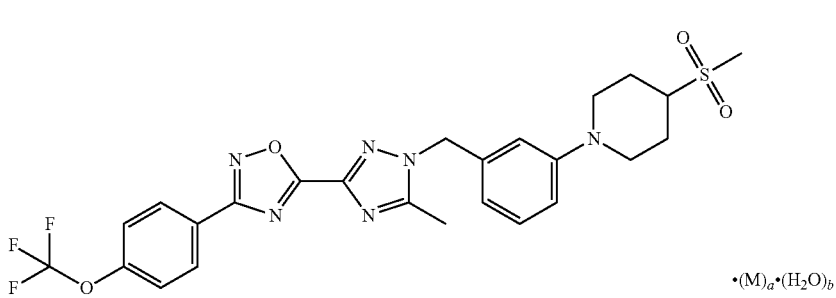 [SMILES: Cc1nc(-c2nc(-c3ccc(OC(F)(F)F)cc3)no2)nn1Cc1cccc(N2CCC(S(C)(=O)=O)CC2)c1]

In some embodiments, M is chosen from hydrochloric acid, sulfuric acid, p-toluenesulfonic acid, nitric acid, methanesulfonic acid, benzenesulfonic acid, oxalic acid, and maleic acid.

In some embodiments, M is chosen from hydrochloric acid, methanesulfonic acid, and benzenesulfonic acid.

In some embodiments, a is a number between 1 and 2 inclusive; and b is a number between 0 and about 2 inclusive.

In particular embodiments, a equals 1 and M is hydrochloric acid.

In particular embodiments, a equals 1 and M is benzenesulfonic acid.

In particular embodiments, a equals 1 and M is methanesulfonic acid.

wherein M is selected from the group consisting of hydrochloric acid, di(tert-butyl) naphthalenesulfonic acid, ethanesulfonic acid, 2-hydroxyethanesulfonic acid, cyclamic acid, p-toluenesulfonic acid, thiocyanic acid, nitric acid, methanesulfonic acid, dodecylsulfonic acid, naphthalene-2-sulfonic acid, benzenesulfonic acid, oxalic acid, saccharine, 2,2-dichloroacetic acid, glycerophosphoric acid, phosphoric acid, (+)-camphor-10-sulfonic acid, sulfuric acid, maleic acid, and pyruvic acid;

a is a fractional or whole number between about 0.5 and about 3.5 inclusive; and b is a fractional or whole number between about 0 and about 10 inclusive.

Also provided are embodiments wherein any embodiment above in paragraphs [0178]-[0212] above may be combined with any one or more of these embodiments, provided the combination is not mutually exclusive. As used herein, two embodiments are "mutually exclusive" when one is defined to be something which cannot overlap with the other. For example, an embodiment wherein M is methanesulfonic acid is mutually exclusive with an embodiment wherein M is hydrochloric acid. However, an embodiment wherein $R^1$ is chosen from a particular group of substituents is not mutually exclusive with an embodiment wherein M is hydrochloric acid.

In some embodiments, the compound has structural Formula VI:

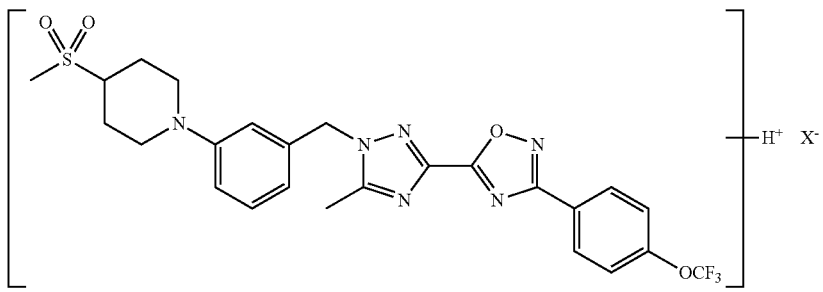

wherein X is chosen from chloride, naphthalene-1,5 disulfonate, di(tert-butyl) naphthalenesulfonate, sulfate, ethane-1,2-disulfonate, ethanesulfonate, 2-hydroxyethanesulfonate, cyclamate, tosylate, thiocyanate, nitrate, mesylate, dodecylsulfonate, naphthalene-2-sulfonate, trifluoroacetate, besylate, oxalate, saccharate, 2,2-dichloroacetate, glycerophosphorate, maleate, phosphorate, (+)-camphoor-10-sulfonate, and pyruvate.

In some embodiments, X is chosen from chloride, sulfate, tosylate, nitrate, mesylate, besylate, and maleate.

In some embodiments, X is chosen from chloride, mesylate, and besylate. In some embodiments, X is chosen from chloride and mesylate. In some embodiments, X is chloride. In some embodiments, X is mesylate.

Also provided are embodiments wherein any embodiment above in paragraphs [0214]-[0216] above may be combined with any one or more of these embodiments, provided the combination is not mutually exclusive.

In some embodiments, the compound is chosen from 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole hydrochloride, 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole 2,2,2-trifluoroacetate, 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole methanesulfonate, and 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole benzenesulfonate. In some embodiments, the compound is 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole hydrochloride. In some embodiments, the compound is 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole 2,2,2-trifluoroacetate. In some embodiments, the compound is 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole methanesulfonate. In some embodiments, the compound is 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole benzenesulfonate.

Pharmaceutical Compositions, Methods of Treatment, and Preparation of Medicaments Also provided herein is a pharmaceutical composition comprising a compound as disclosed herein, together with a pharmaceutically acceptable carrier.

Also provided herein is a method of treatment of a HIF pathway-mediated disease comprising the administration of a therapeutically effective amount of a compound as disclosed herein to a patient in need thereof.

In some embodiments, said disease is cancer.

In some embodiments, said cancer is selected from the group consisting of colon cancer, breast cancer, ovarian cancer, lung cancer, prostate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; cancers of the thyroid and other endocrine glands; Hodgkin's disease, non-Hodgkin's lymphomas, multiple myeloma, hematopoietic malignancies including leukemias (Chronic Lymphocytic Leukemia (CLL), Acute Lymphocytic Leukemia(ALL)) and lymphomas including lymphocytic, granulocytic and monocytic; adrenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme (also called simply "glioblastoma"), head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor. In some embodiments, the cancer is glioblastoma. In some embodiments, the cancer is neuroblastoma. In some embodiments, the cancer is lymphoma. In some embodiments, the cancer is diffuse large B-cell lymphoma.

Also provided herein is a method of treatment of a disease caused by abnormal cell proliferation comprising the administration of a therapeutically effective amount of a compound as disclosed herein to a patient in need thereof.

Also provided herein is a method for achieving an effect in a patient comprising the administration of a therapeutically effective amount of a compound as disclosed herein to a patient, wherein the effect is selected from the group consisting of preventing or reducing resistance to radiotherapy and chemotherapy, preventing or reducing tumor invasion and tumor metastasis, and preventing or reducing angiogenesis.

In the embodiments above in paragraphs [0219]-[0224], compounds disclosed herein include, without limitation, any embodiment above in paragraphs [0178]-[0218].

Also provided herein is the use of a compound as disclosed herein in the treatment of, or in the preparation of a medicament for the of treatment of, a HIF pathway-mediated disease comprising the administration of a therapeutically effective amount.

In some embodiments, said disease is cancer.

In some embodiments, said cancer is selected from the roup consisting of colon cancer, breast cancer, ovarian cancer, lung cancer, prostate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; cancers of the thyroid and other endocrine glands; Hodgkin's disease, non-Hodgkin's lymphomas, multiple myeloma, hematopoietic malignancies including leukemias (Chronic Lymphocytic Leukemia (CLL), Acute Lymphocytic Leukemia(ALL)) and lymphomas including lymphocytic, granulocytic and monocytic; adrenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme (also called simply "glioblastoma"), head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor. In some embodiments, the cancer is glioblastoma. In some embodiments, the cancer is neuroblastoma. In some embodiments, the cancer is lymphoma. In some embodiments, the cancer is diffuse large B-cell lymphoma.

Also provided herein is the use of a compound as disclosed herein in the treatment of, or in the preparation of a medicament for the of treatment of, a disease caused by abnormal cell proliferation.

Also provided herein is the use of a compound as disclosed herein, or in the preparation of a medicament, for achieving an effect in a patient comprising the administration of a therapeutically effective amount of a compound as disclosed herein to a patient, wherein the effect is selected from the group consisting of preventing or reducing resistance to radiotherapy and chemotherapy, preventing or reducing tumor invasion and tumor metastasis, and preventing or reducing angiogenesis.

In the embodiments above in paragraphs [0226]-[0230], compounds disclosed herein include, without limitation, any embodiment above in paragraphs [0178]-[0218].

The disclosure is further illustrated by the following examples, which may be made by methods known in the art and/or as shown below.

Synthesis

Compounds

Compounds according to Formula I may be made from the following Examples, which may be made by methods known in the art, and/or as shown below, and/or as disclosed in U.S. application Ser. No. 13/974,258, filed Aug. 23, 2013, the disclosure of which is hereby incorporated by reference as if written herein in its entirety.

EXAMPLE 80

4-Methanesulfonyl-1-{3-[(5-methyl-3-{3-[4-(trifluoromethoxy)phenyl]-1,2,4-oxadiazol-5-yl}-1H-1,2,4-triazol-1-yl)methyl]phenyl}piperidine

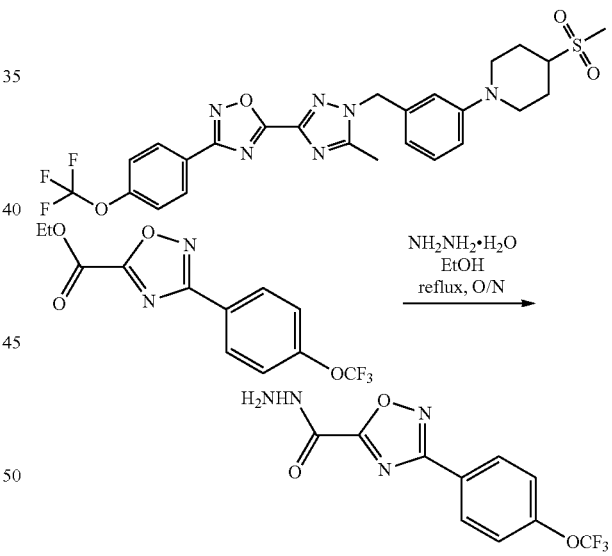

Step 1

3-(4-(Trifluoromethoxy)phenyl)-1,2,4-oxadiazole-5-carbohydrazide

To the solution of ethyl 3-(4-(trifluoromethoxy)phenyl)-1,2,4-oxadiazole-5-carboxylate (13.6 g, 45.0 mmol) in EtOH (200 mL), NH$_2$NH$_2$·H$_2$O (80%, 14 mL, 225 mmol) was added. The reaction mixture was stirred at RT overnight. The desired compound precipitated from the reaction mixture, filtered and washed with EtOH (50 mL) to afford 3-(4-(trifluoromethoxy)phenyl)-1,2,4-oxadiazole-5-carbohydrazide as a light yellow solid (9.7 g, 75%). MS (ES+) C$_{10}$H$_7$F$_3$N$_4$O$_3$ requires: 288. found: 289 [M+H]$^+$.

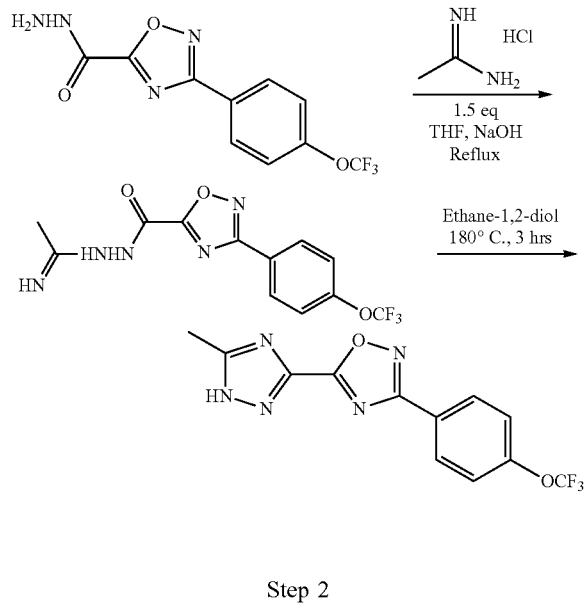

Step 2

5-(5-Methyl-1H-1,2,4-triazol-3-yl)-3-(4-(trifluoromethoxy)phenyl)-1,2,4-oxadiazole To a solution of 3-(4-(trifluoromethoxy)phenyl)-1,2,4-oxadiazole-5-carbohydrazide (9.7 g, 33.7 mmol) and acetimidamide hydrochloride (4.8 g, 50.5 mmol) in dry THF (300 mL), NaOH (2.0 g, 50.5 mmol) was added at RT. The mixture was refluxed overnight. The solution was cooled, concentrated and ethane-1,2-diol (100 mL) was added. The resulting mixture was heated at 180° C. for 3 h, cooled to RT, diluted with H$_2$O (800 mL), and extracted with EtOAc (3×400 mL). The combined organic layers were washed with H$_2$O (300 mL) and brine (100 mL), dried over Na$_2$SO$_4$, filtered, and concentrated under reduced pressure to afford the crude solid product, which was treated with EtOAc (150 mL). The resulting suspension was stirred at RT for 15 min, and then filtered to afford 4.8 g of the pure desired compound. The remaining filtrate was concentrated and purified by silica gel column chromatography (Petroleum ether: EtOAc=1:1) to afford 1.4 g of another batch of 5-(5-methyl-1H-1,2,4-triazol-3-yl)-3-(4-(trifluoromethoxy)phenyl)-1,2,4-oxadiazole as a white solid-overall 6.2 g, yield 59%. MS (ES+) C$_{12}$H$_8$F$_3$N$_5$O$_2$ requires: 311. found: 312 [M+H]$^+$.

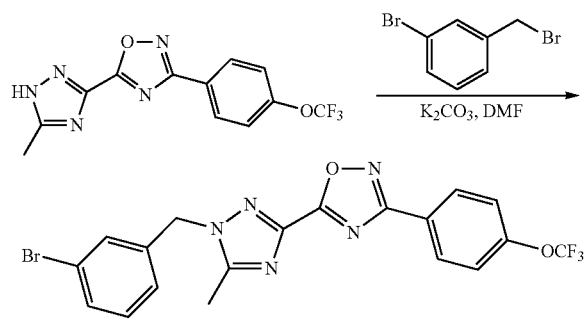

Step 3

5-(1-(3-Bromobenzyl)-5-methyl-1H-1,2,4-triazol-3-yl)-3-(4-(trifluoromethoxy)phenyl)-1,2,4-oxadiazole 5-(5-Methyl-1H-1,2,4-triazol-3-yl)-3-(4-(trifluoromethoxy)phenyl)-1,2,4-oxadiazole (100 mg, 0.321 mmol) was placed in THF (3 mL) and K$_2$CO$_3$ (66 mg, 0.482 mmol) was added. The reaction was stirred for 5 min and 1-bromo-4-(bromomethyl)benzene (84 mg, 0.338 mmol) was added. The reaction was stirred at 50° C. overnight and was then partitioned between H$_2$O (15 mL) and EtOAc (15 mL). The organic layer was separated, washed with H$_2$O (2×10 mL) and brine (10 mL), dried over Na$_2$SO$_4$, filtered, and concentrated to afford the crude product which was purified by silica gel chromatography (EtOAc/Hexane 10%-100% EtOAc) to afford 5-(1-(3-bromobenzyl)-5-methyl-1H-1,2,4-triazol-3-yl)-3-(4-(trifluoromethoxy)phenyl)-1,2,4-oxadiazole as a white solid (82 mg, 53%). MS (ES+) C$_{19}$H$_{13}$BrF$_3$N$_5$O$_2$ requires: 479, 481 found 480 [M+H]$^+$, 482 [M+2+H]$^+$ (1:1); $^1$H NMR (600 MHz, CDCl$_3$) δ 8.28 (d, J=8.8 Hz, 2H), 7.48 (d, J=7.9 Hz, 1H), 7.41 (s, 1H), 7.34 (d, J=8.8 Hz, 2H), 7.26 (d, J=7.6 Hz, 1H), 7.17 (d, J=7.9 Hz, 1H), 5.43 (s, 2H), 2.55 (s, 3H).

Step 4

4-Methanesulfonyl-1-{3-[(5-methyl-3-{3-[4-(trifluoromethoxy)phenyl]-1,2,4-oxadiazol-5-yl}-1H-1,2,4-triazol-1-yl)methyl]phenyl}piperidine A mixture of 5-(1-(3-bromobenzyl)-5-methyl-1H-1,2,4-triazol-3-yl)-3-(4-(trifluoromethoxy)phenyl)-1,2,4-oxadiazole (165 mg, 0.34 mmol), 4-(methylsulfonyl)piperidine (62 mg, 0.38 mmol), and Cs$_2$CO$_3$ (224 mg, 0.69 mmol) in toluene (2 mL) was degassed with argon for 5 min. Pd$_2$(dba)$_3$ (0.15 mg, 0.017 mmol) and dicyclohexyl(2',4',6'-triisopropyl-[1,1'-biphenyl]-2-yl)phosphine (33 mg, 069 mmol) were added and the reaction mixture was degassed a second time with argon for 5 min, then heated to 140° C. for 18 h. The mixture was then cooled to RT, diluted with EtOAc (15 mL), filtered through a pad of Celite, and concentrated under reduced pressure. The crude product was purified by prep-HPLC (Mobile phase: A=0.1% TFA/H$_2$O, B=0.1% TFA/MeCN; Gradient: B=40%-80% in 12 min; Column: C18) to give the title compound as a white solid; MS (ES+) C$_{25}$H$_{25}$F$_3$N$_6$O$_4$S requires: 562. found: 563 [M+H]$^+$; $^1$H NMR (600 MHz, DMSO-d$_6$) δ 8.22 (d, J=8.8 Hz, 2H), 7.61 (d, J=8.2 Hz, 2H), 7.21 (t, J=7.9 Hz, 1H), 6.97 (bs, 1H), 6.94 (dd, J=8.3, 2.4 Hz, 1H), 6.64 (d, J=7.5 Hz, 1H), 5.48 (s, 2H), 3.86 (bd, J=13.4 Hz, 2H), 3.28 (m, 1H), 2.94 (s, 3H), 2.76 (m, 2H), 2.57 (s, 3H), 2.06 (bd, J=13.4 Hz, 2H), 1.68 (ddd, J=16.5, 12.5, 4.1 Hz, 2H); $^{19}$F NMR (282 MHz, DMSO-d$_6$) δ −56.6.

Additional compounds from which salts may be made include:
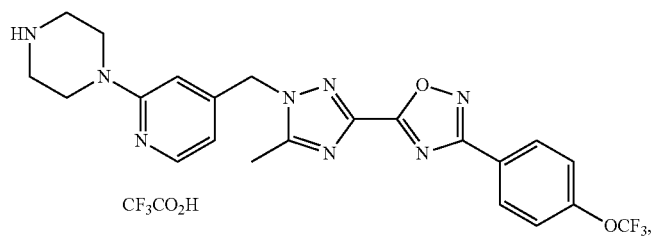
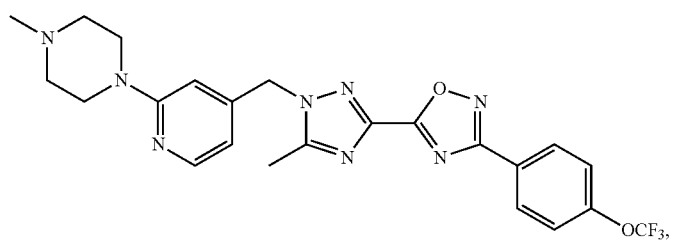
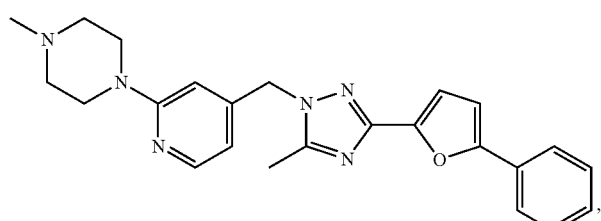
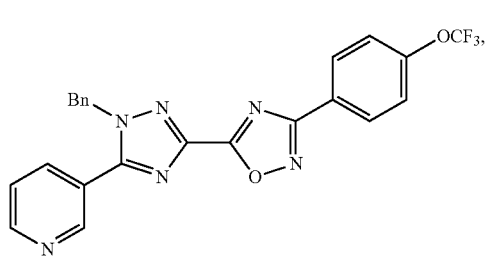
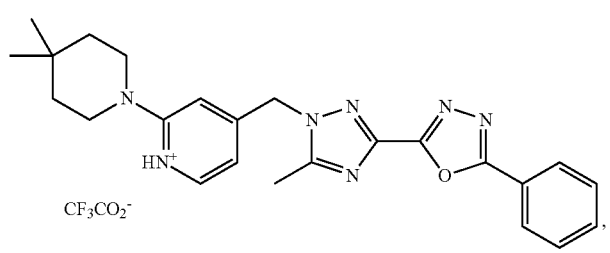
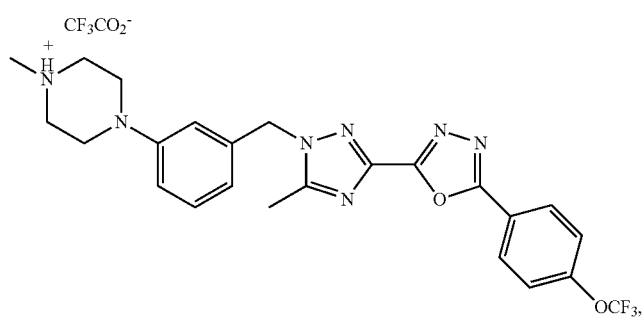

-continued
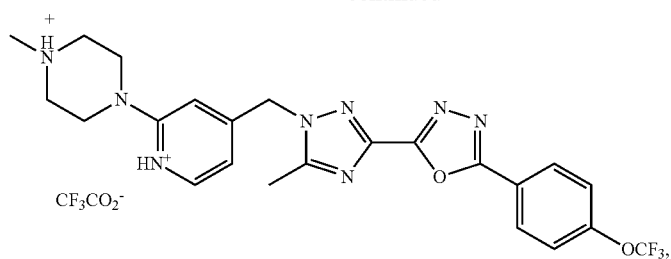
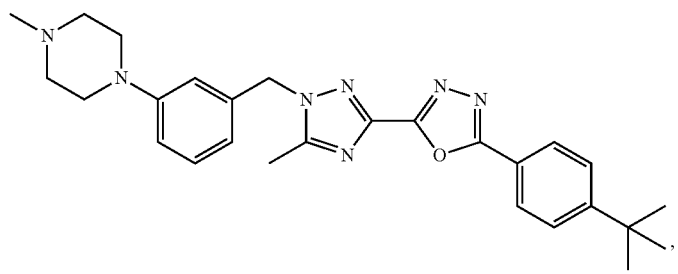
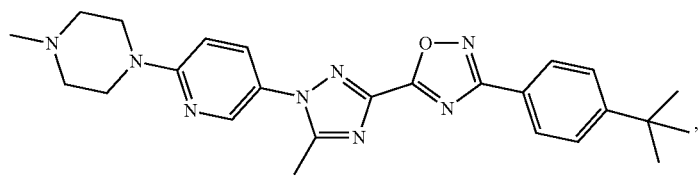
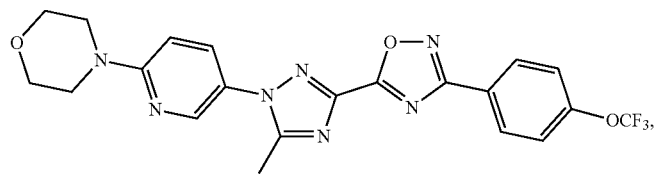
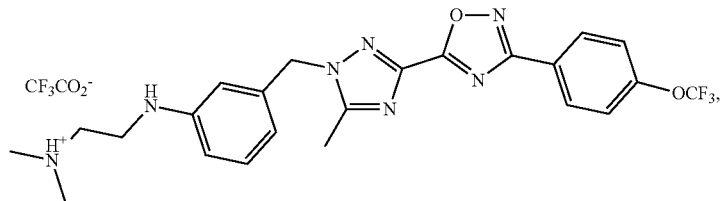
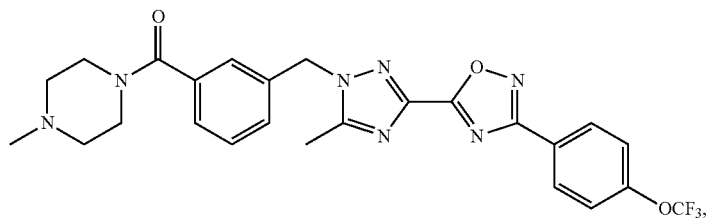
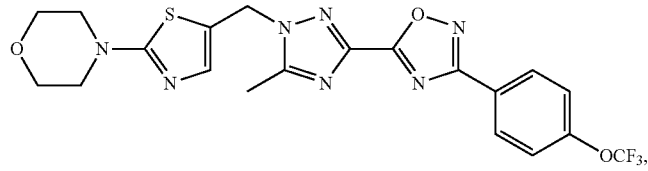
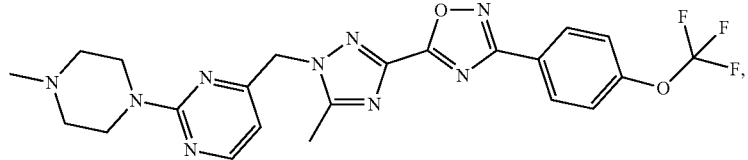

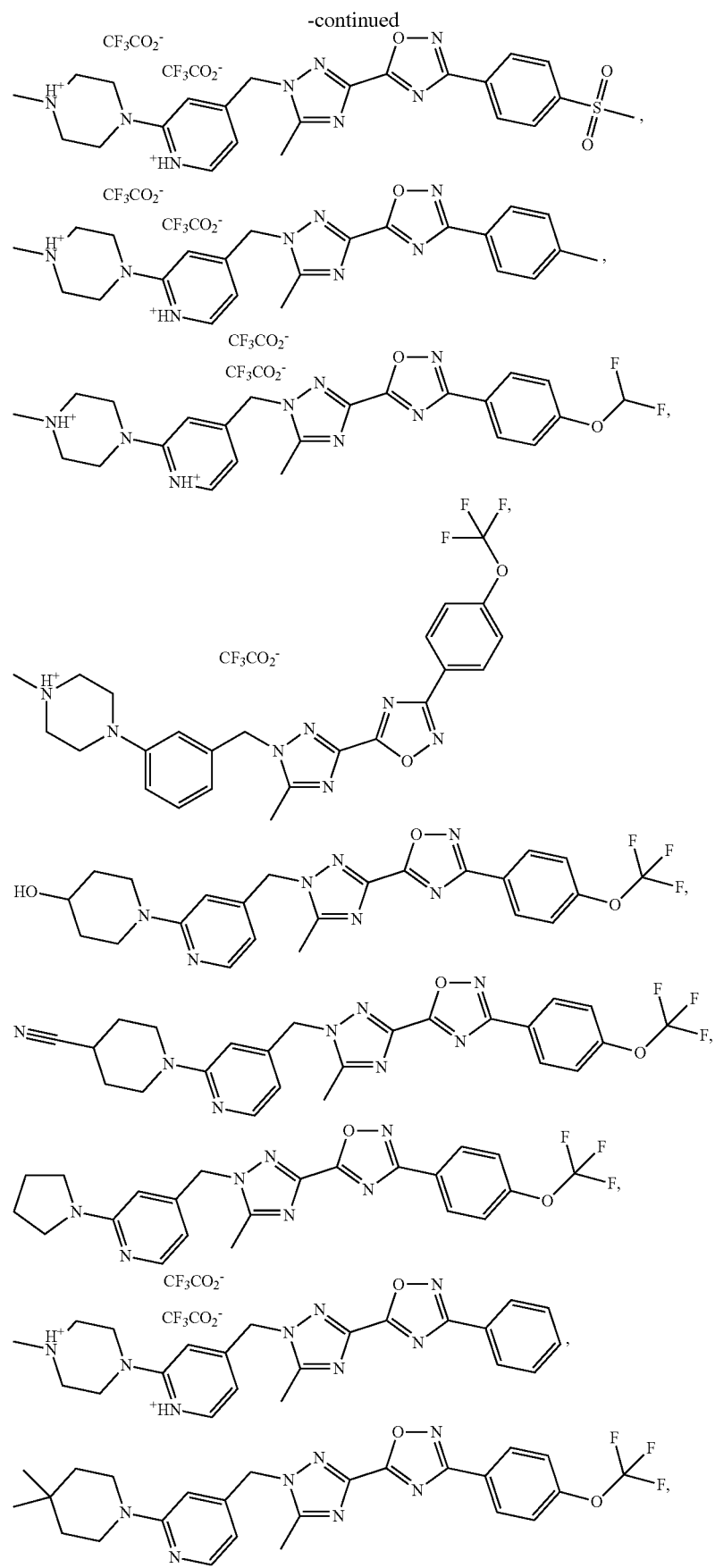

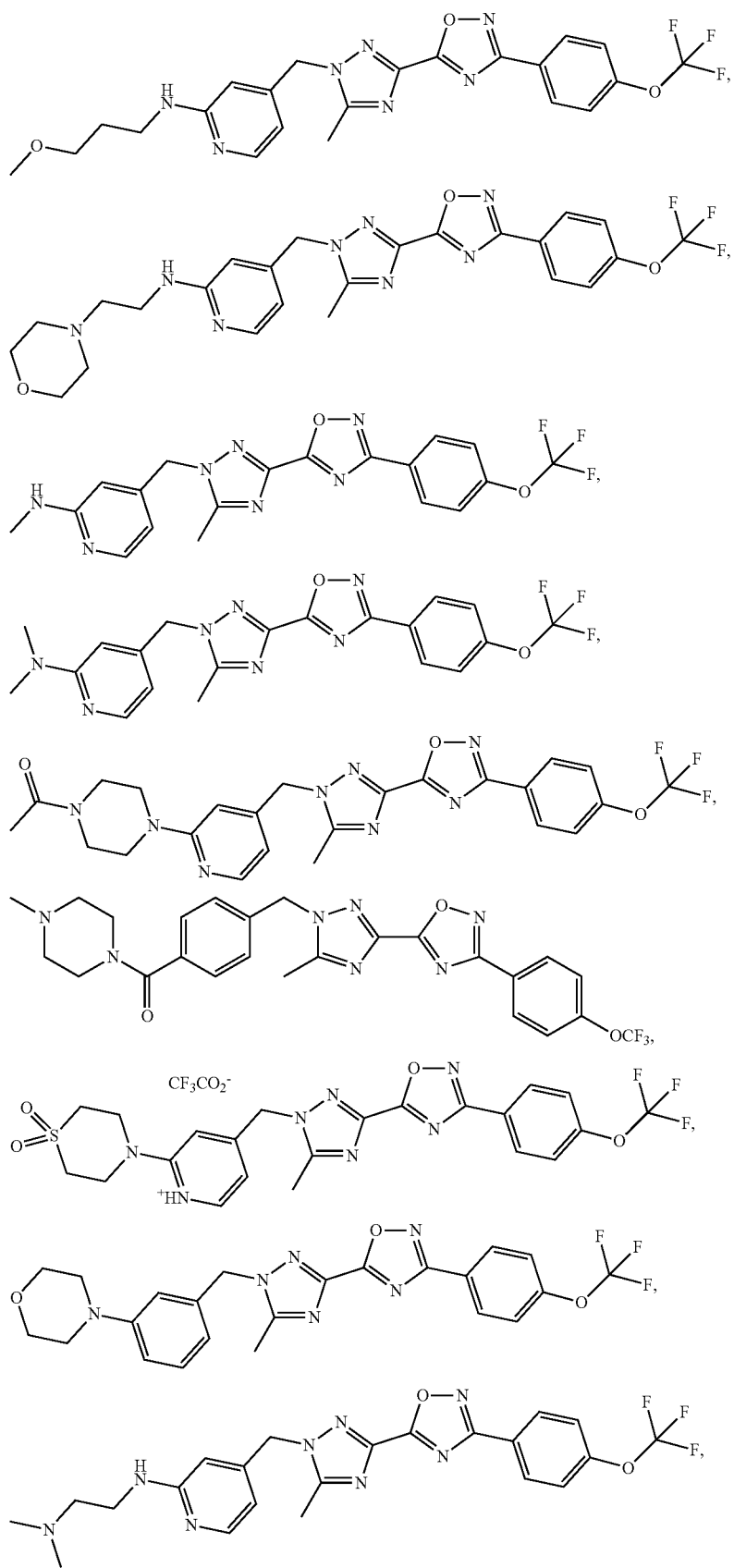

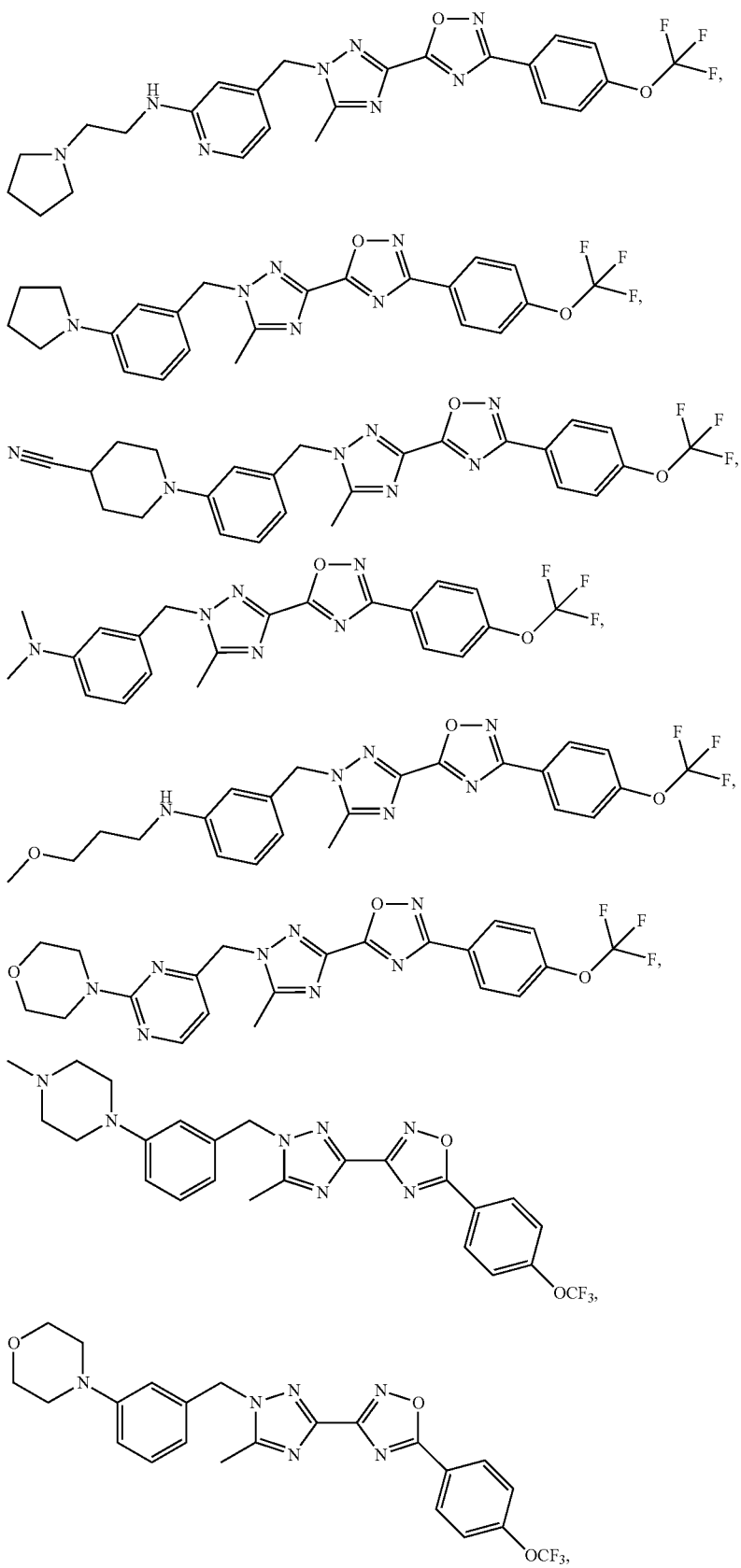

-continued
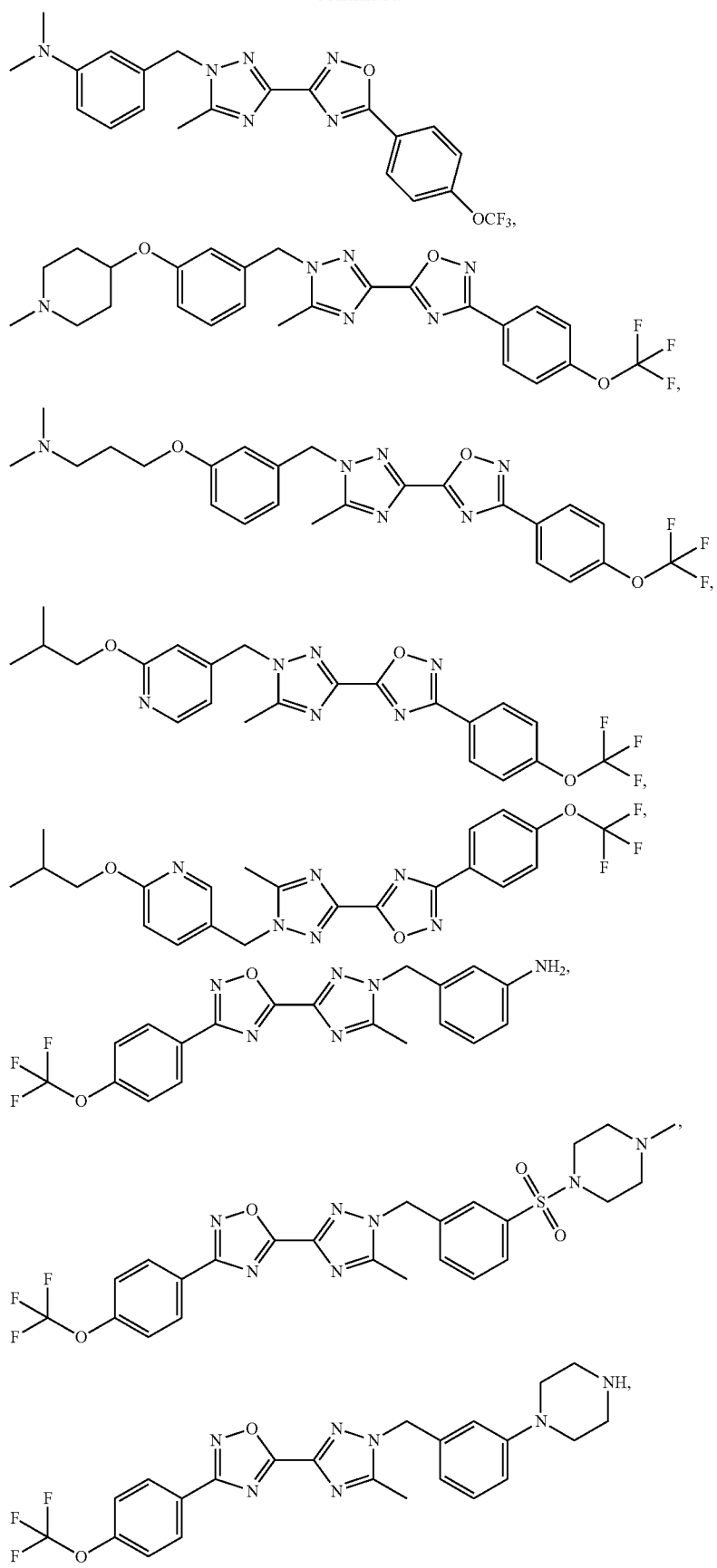

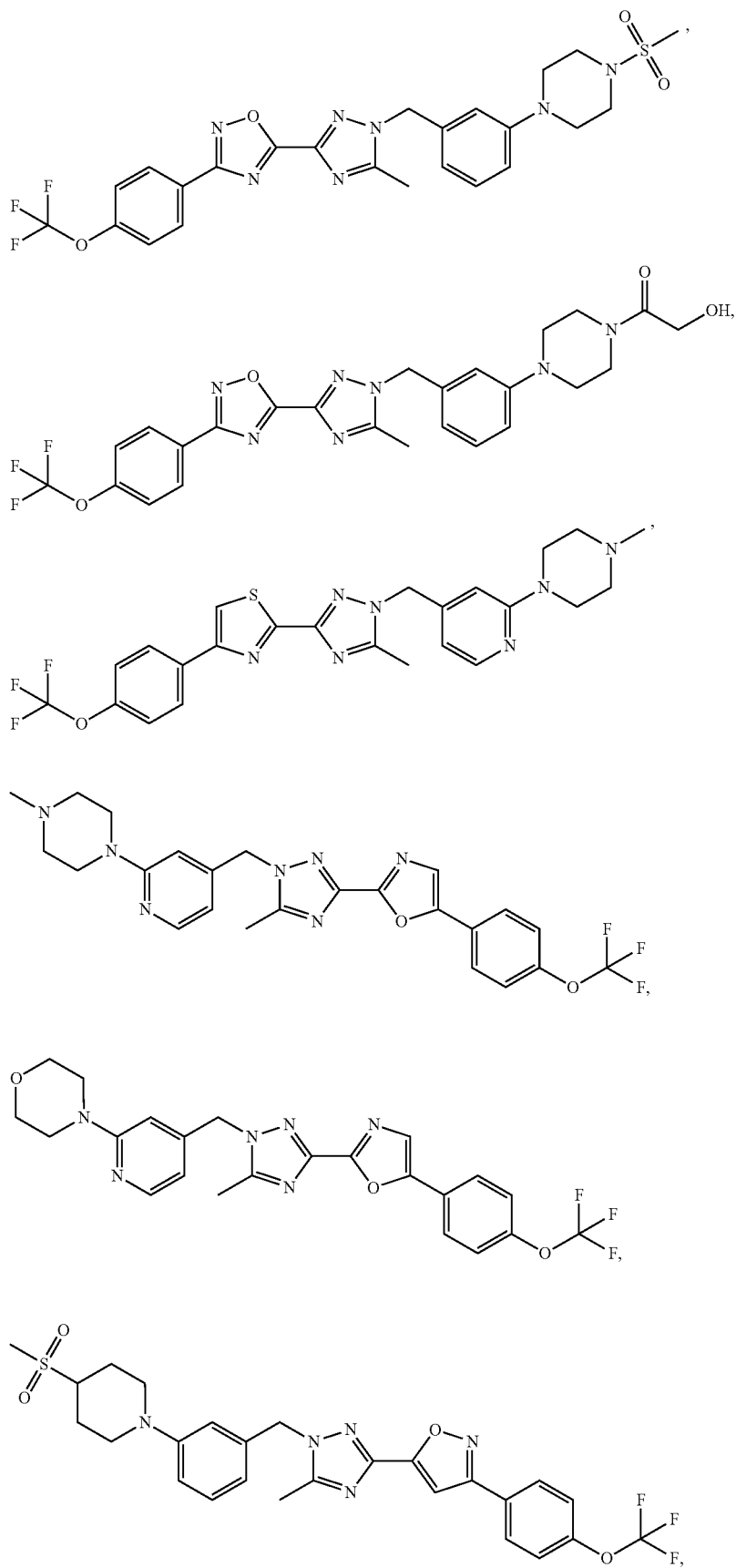

-continued
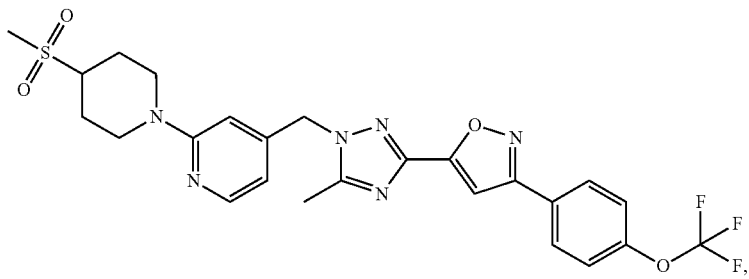
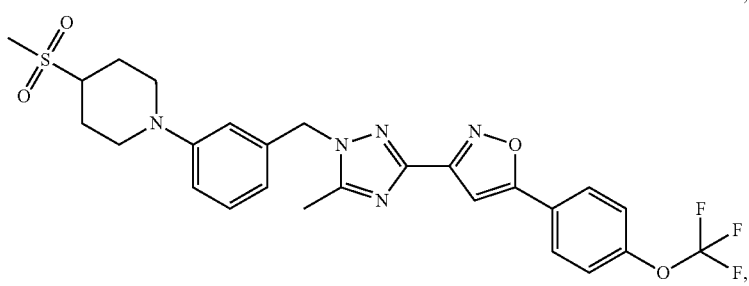
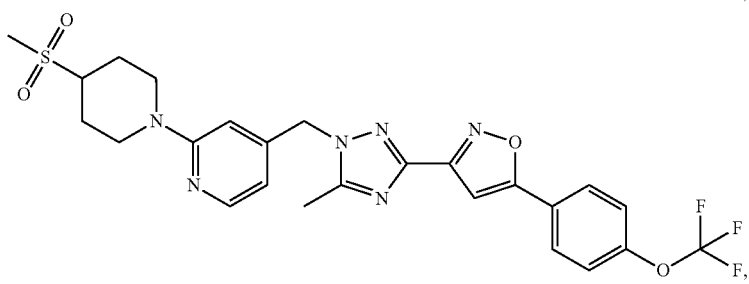
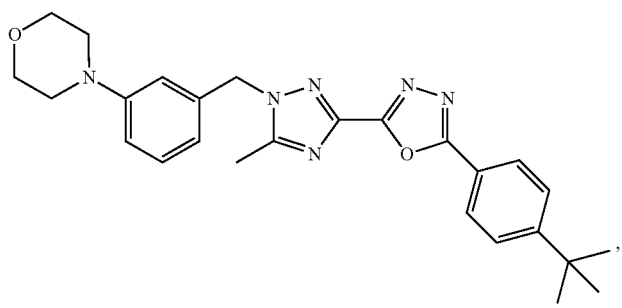
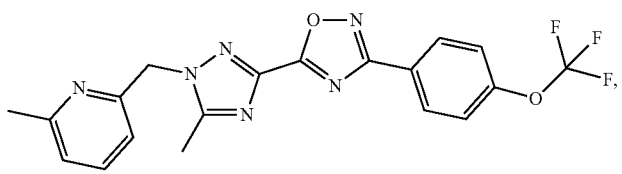
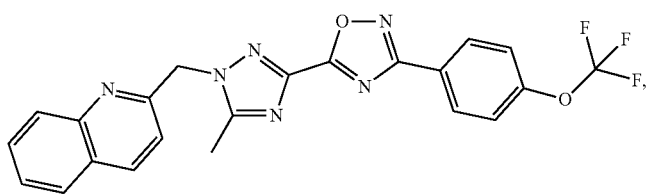

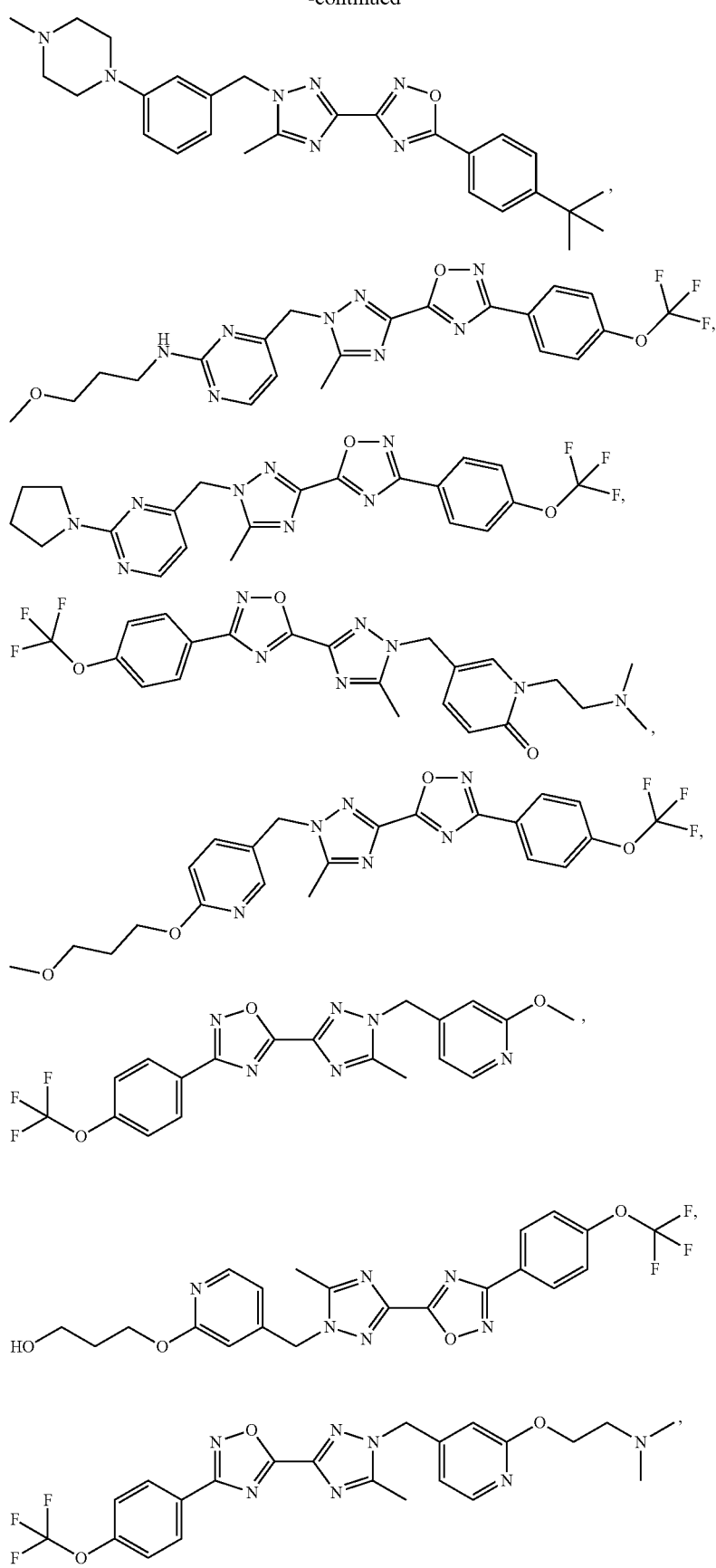

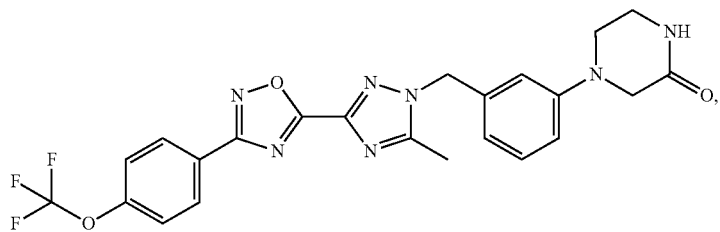
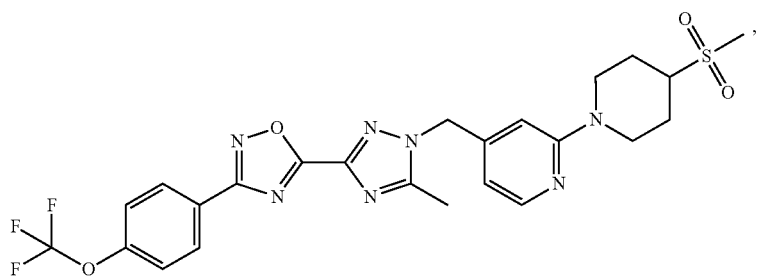
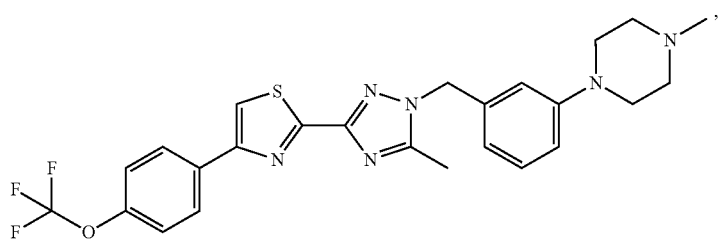
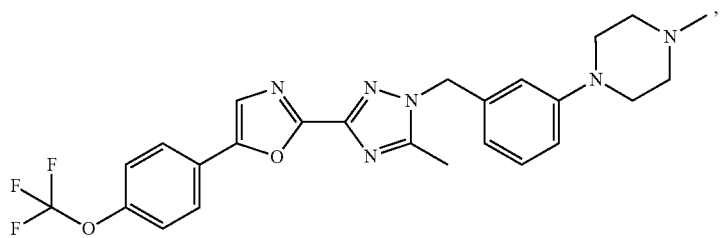
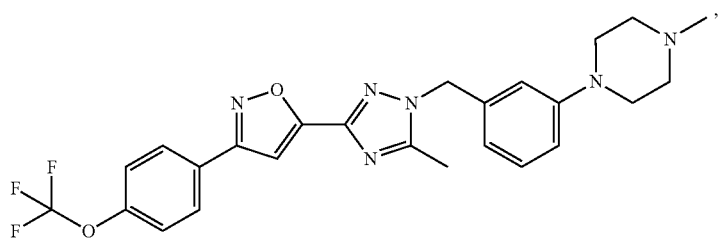
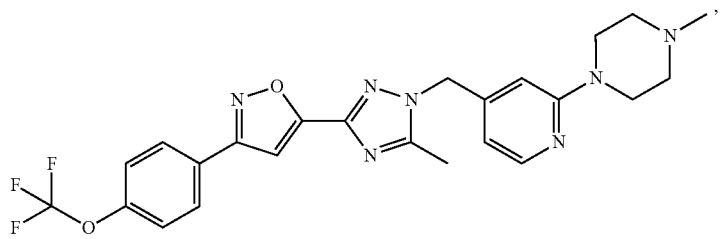
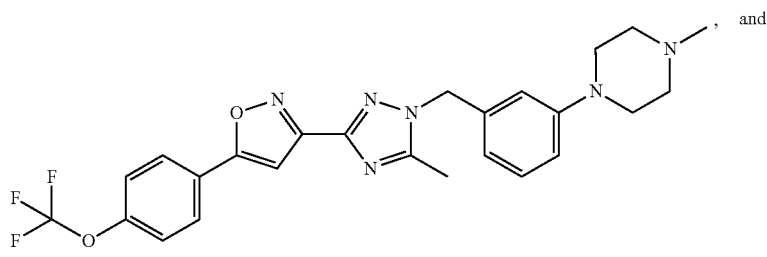

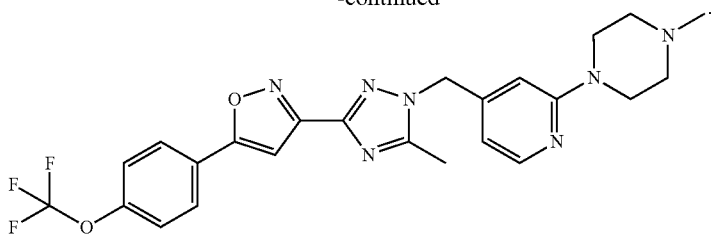

Salts

The method is directed to chemistry involved in the synthesis of salts and/or hydrates of the heterocycles described herein. One of skill in the art would understand that the disclosed salts can be made in a variety of ways that may differ from the exemplary scheme described below. Acid addition salts of the compounds of formula I can be prepared in a standard manner in a suitable solvent from the parent compound and an excess of an acid, such as (+)-camphor-10-sulfonic acid, 2,2-dichloroacetic acid, 2-hydroxyethanesulfonic acid, 4-amino salicylic acid, acetic acid, adipic acid, ascorbic acid, aspartic acid, benzoic acid, benzenesulfonic acid, camsylate, capric acid, caproic acid, caprylic acid, cinnamic acid, citric acid, cyclamic acid, di(tert-butyl) naphthalenesulfonic acid, dodecylsulfonic acid, ethanesulfonic acid, formic acid, fumaric acid, gentisic acid, glutamic acid, glycerophosphoric acid, glutaric acid, glycine, hydroboric acid, hydrobromic acid, hydrochloric acid, isobutyric acid, lactic acid, lauric acid, maleic acid, malic acid, malonic acid, mandelic acid, methanesulfonic acid, naphthalene-2-sulfonic acid, nitric acid, oxalic acid, phosphoric acid, propionic acid, p-toluenesulfonic acid, pyroglutamic acid, pyruvic acid, saccharine, salicylic acid, sebacic acid, stearic acid, succinic acid, sulfuric acid, tartaric acid, and thiocyanic acid. Certain of the compounds form inner salts or zwitterions that may be acceptable.

EXAMPLE 164

Preparation of Salts 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole hydrochloride

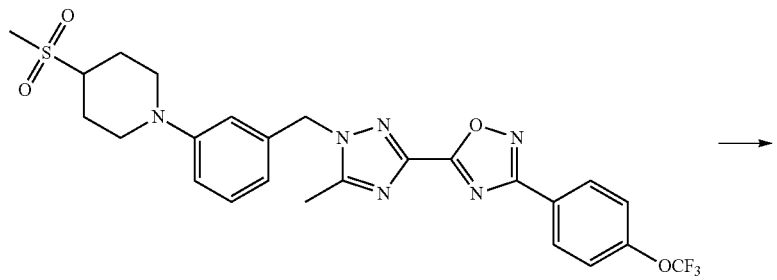

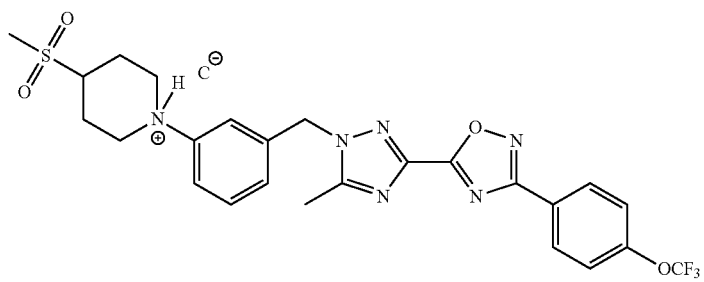

5-(5-methyl-1-(3-(4-(methylsulfonyl)piperidin-1-yl) benzyl)-1H-1,2,4-triazol-3-yl)-3-(4-(trifluoromethoxy)phenyl)-1,2,4-oxadiazole hydrochloride To a solution of 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole (2.67 g, 4.75 mmol) in DCM (50 mL) was added HCl (1 M in $Et_2O$) (4.79 ml, 4.79 mmol) and the resulting mixture was stirred at 50° C. for 1 h. The reaction mixture was allowed to cool to room temperature and the solid was collected by vacuum filtration to give 1-(3-((5-methyl-3-(3-(4-(trifluoromethoxy)phenyl)-1,2,4-oxadiazol-5-yl)-1H-1,2,4-triazol-1-yl)methyl)phenyl)-4-(methylsulfonyl)piperidin-1-ium chloride (2.68 g, 4.47 mmol, 94% yield). $^1$H NMR (600 MHz, $CDCl_3$) δ 8.28 (d, J=8.7 Hz, 2H), 8.01 (brs, 1H), 7.70-7.62 (m, 1H), 7.57-7.50 (m, 1H), 7.37-7.28 (m, 3H), 5.49 (s, 2H), 3.94 (app brs, 2H), 3.42 (app brs, 2H), 3.25 (brs, 1H), 3.02 (s, 3H), 2.96 (app brs, 2H), 2.77 (app brs, 2H), 2.64 (s, 3H).

1-(3-((5-methyl-3-(3-(4-(trifluoromethoxy)phenyl)-1,2,4-oxadiazol-5-yl)-1H-1,2,4-triazol-1-yl)methyl) phenyl)-4-(methylsulfonyl)piperidin-1-ium benzenesulfonate (besylate)

To a solution of 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole (100 mg, 0.178 mmol) in DCM (1778 μl) was added benzenesulfonic acid (29.5 mg, 0.187 mmol) and the resulting mixture was stirred at 50° C. for 1 h. The reaction mixture was allowed to cool to room temperature and the volatiles were removed under reduced pressure. The solid was collected, triturated with ether (3×2 mL), and dried under reduced pressure to give 1-(3-((5-methyl-3-(3-(4-(trifluoromethoxy)phenyl)-1,2,4-oxadiazol-5-yl)-1H-1,2,4-triazol-1-yl)methyl)phenyl)-4-(methylsulfonyl)piperidin-1-ium benzenesulfonate (120 mg, 94%). $^1$H NMR (600 MHz, $CDCl_3$) δ 12.67 (brs, 1H), 8.26 (d, J=8.7 Hz, 2H), 7.96-7.87 (m, 3H), 7.64-7.56 (brs, 1H), 7.53-7.46 (m, 1H), 7.46-7.40 (m, 3H), 7.39-7.31 (m, 3H), 5.41 (s, 2H), 4.07-3.75 (app brs, 2H), 3.73-3.56 (app brs, 2H), 3.51-3.38 (brs, 1H), 3.14-2.85 (app brs, 3H), 2.84-2.64 (app brs, 2H), 2.60-2.39 (app brs, 4H), 2.37-1.87 (brs, 1H).

1-(3-((5-methyl-3-(3-(4-(trifluoromethoxy)phenyl)-1,2,4-oxadiazol-5-yl)-1H-1,2,4-triazol-1-yl)methyl) phenyl)-4-(methylsulfonyl)piperidin-1-ium methanesulfonate (mesylate)

To a solution of 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole (120 mg, 0.213 mmol) in DCM (2 mL) was added methanesulfonic acid (213 μl, 0.213 mmol) and the resulting mixture was stirred at 50° C. for 1 h. The reaction mixture was allowed to cool to room temperature and the volatiles were removed under reduced pressure. The solid was collected, triturated with ether (3×2 mL), and dried under reduced pressure to give 1-(3-((5-methyl-3-(3-(4-(trifluoromethoxy)phenyl)-1,2,4-oxadiazol-5-yl)-1H-1,2,4-triazol-1-yl)methyl)phenyl)-4-(methylsulfonyl)piperidin-1-ium methanesulfonate (135 mg, 95%). $^1$H NMR (600 MHz, $CDCl_3$) δ 8.31 (d, J=8.7 Hz, 2H), 7.91-7.66 (brs, 1H), 7.60-7.47 (app brs, 2H), 7.40-7.30 (m, 3H), 5.52 (s, 2H), 4.01-3.86 (app brs, 2H), 3.52-3.32 (app brs, 2H), 3.31-3.18 (brs, 1H), 3.02 (s, 3H), 2.91 (s, 3H), 2.85-2.41 (m, 7H).

The trifluoroacetic acid salt was prepared in a similar manner to the mesylate salt.

Additional Salt Preparation

Acetonitrile was selected as solvent system to prepare salts of Example 80.

TABLE 1

Counter-ions used to prepare salts of 4-Methanesulfonyl-1-{3-[(5-methyl-3-{3-[4-(trifluoromethoxy)phenyl]-1,2,4-oxadiazol-5-yl}-1H-1,2,4-triazol-1-yl)methyl]phenyl}piperidine (Example 80)

| No. | Acids | MW | pKa | API/Acid (molar ratio) |
|---|---|---|---|---|
| 1 | HCl | 36.46 | −6 | 1:1 |
| 2 | $H_2SO_4$ | 98.08 | −3, 1.92 | 1:1 |
| 3 | $H_2SO_4$ | 98.08 | −3, 1.92 | 2:1 |
| 4 | $CH_3SO_3H$ | 96.10 | −1.2 | 1:1 |
| 5 | p-toluenesulfonic acid | 172.2 | −1.34 | 1:1 |

Samples of Example 80 were dissolved in ACN at ambient laboratory temperature. Appropriate amount of acids dissolved in corresponding solvents were added to the samples according to 1:1 (or 1:2) molar ratio. Additionally, Example 80 and solid acid (p-toluenesulfonic acid) were slurried (and in the case of Example 80, dissolved as well) in ACN individually by stirring for 24 hrs, for use as XRPD controls.

The solids that precipitated out immediately after adding acids were isolated by centrifugation and dried in a fume hood. Samples which yielded no immediate precipitant were stirred at room temperature for 24 hrs. After stirring for 24 hrs, solids precipitated from solution were also isolated by centrifugation and dried in a fume hood. As for samples which had no solids obtained after stifling 24 hrs, they were evaporated by nitrogen to obtain solids.

Solid State Characterization of Solids Obtained in Counter-Ion Screen

Figure 11:
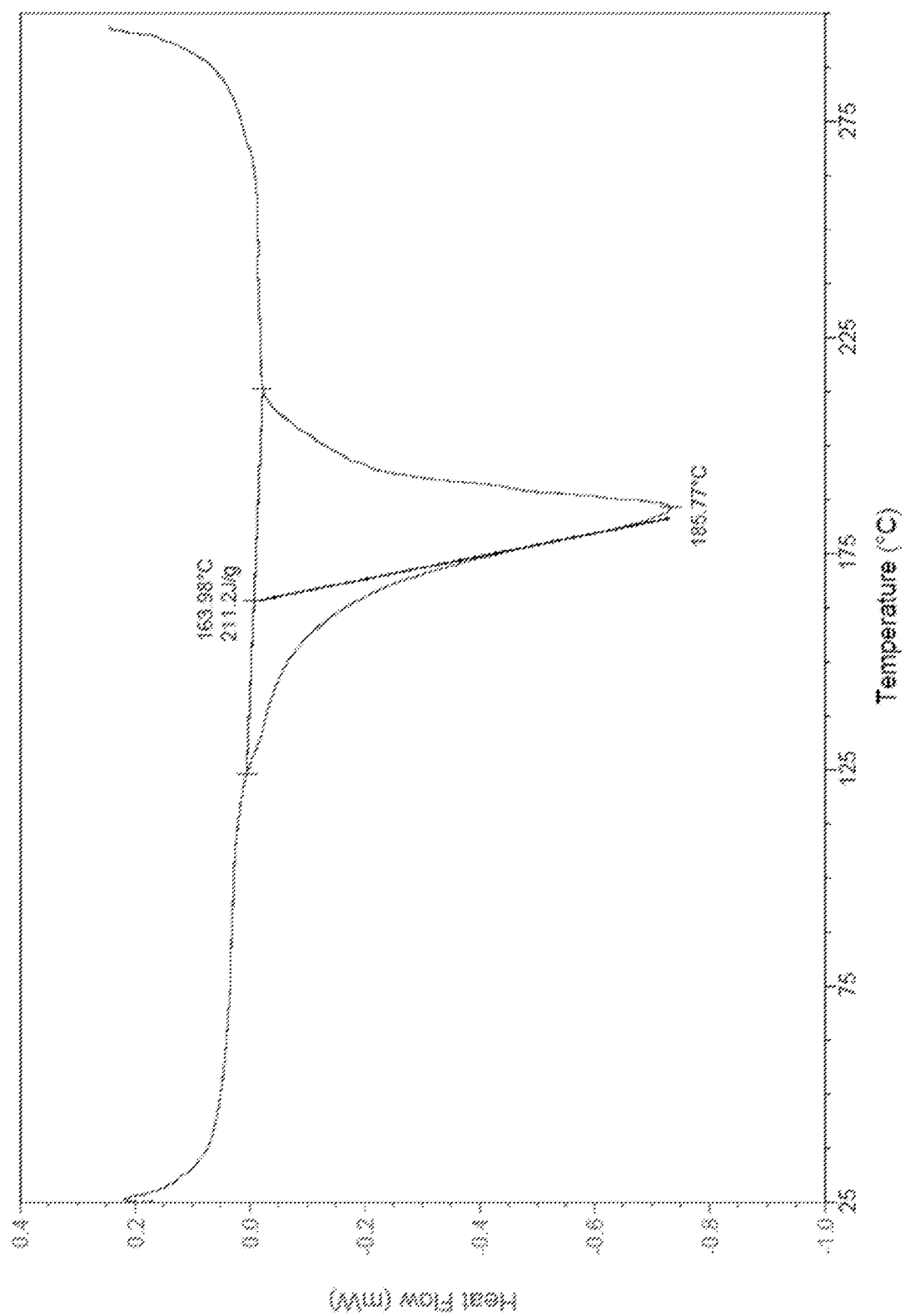
FIG. 11—DSC of the hydrochloride salt of Example 80.

Solids were visualized under a polarized light microscope (PLM) to confirm the presence of crystals. Crystals were dried in fume hood overnight then characterized by XRPD. In order to confirm the formed solids are true salts instead of different polymorphs of the free base, the formed solids were compared with API control (Table 2, FIG. 11).

Based on the PLM and XRPD results (Table 2 and FIG. 11), no form transformation was detected for API control (Example 80 free base). Samples obtained from HCl and $CH_3SO_3H$ showed different XRPD pattern from original free base that indicate they may form the potential crystal salts. The two potential crystal salts were further characterized to understand their physicochemical properties. Samples obtained from $H_2SO_4$ with two ratios (1:1 and 2:1) and p-toluenesulfonic acid showed amorphous form.).

To confirm and obtain physicochemical properties of all the potential crystalline salts, further characterizations (DSC, TGA, NMR/ELSD, etc.) were conducted for the hydrochloride candidate and mesylate candidate (Table 2 and FIGS. 11-14).

Figure 12:
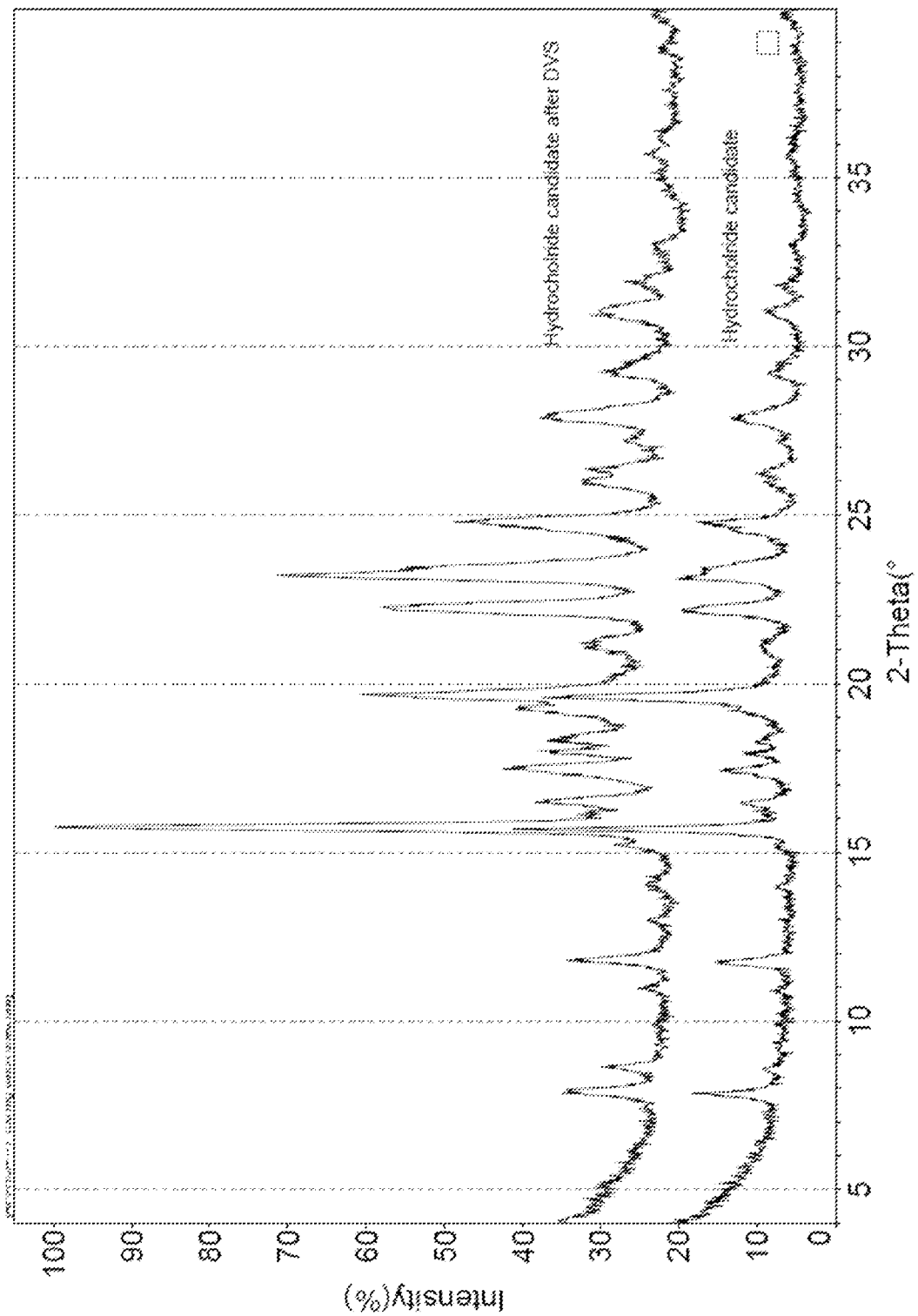
FIG. 12—The hydrochloride salt of Example 80 after DVS.
Figure 13:
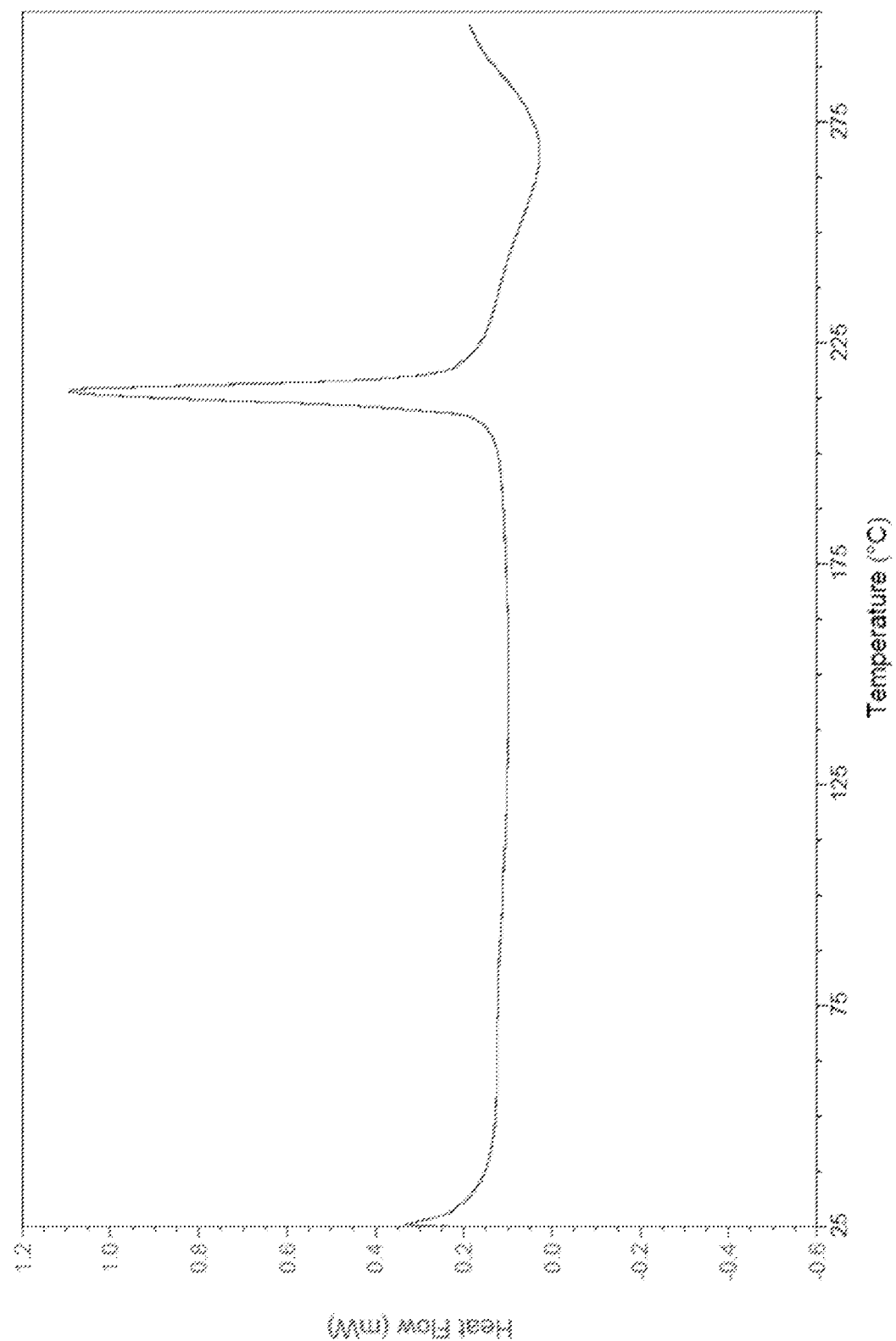
FIG. 13—DSC of the mesylate salt of Example 80.
Figure 14:
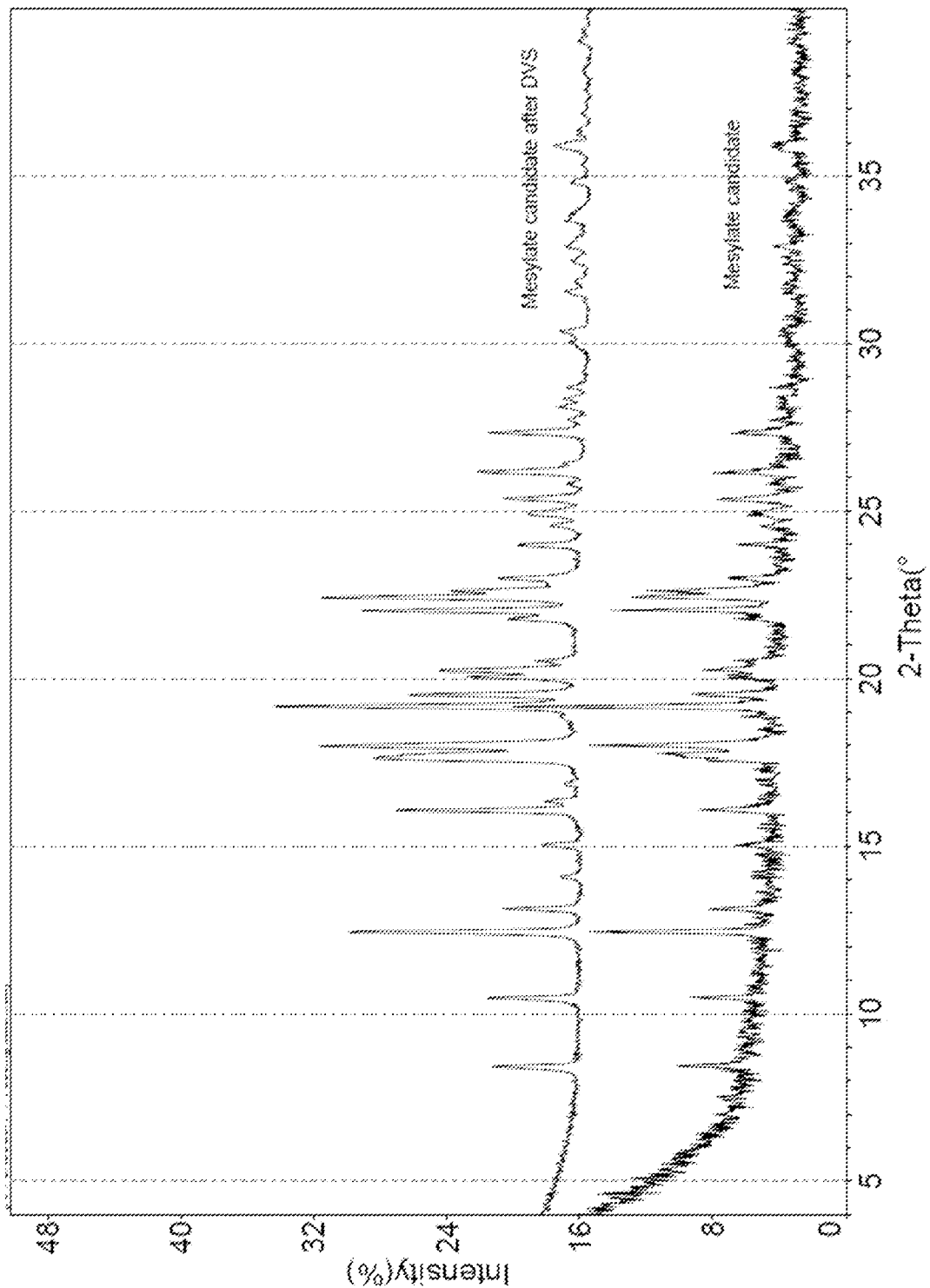
FIG. 14—The mesylate salt of Example 80 after DVS.
Figure 16:
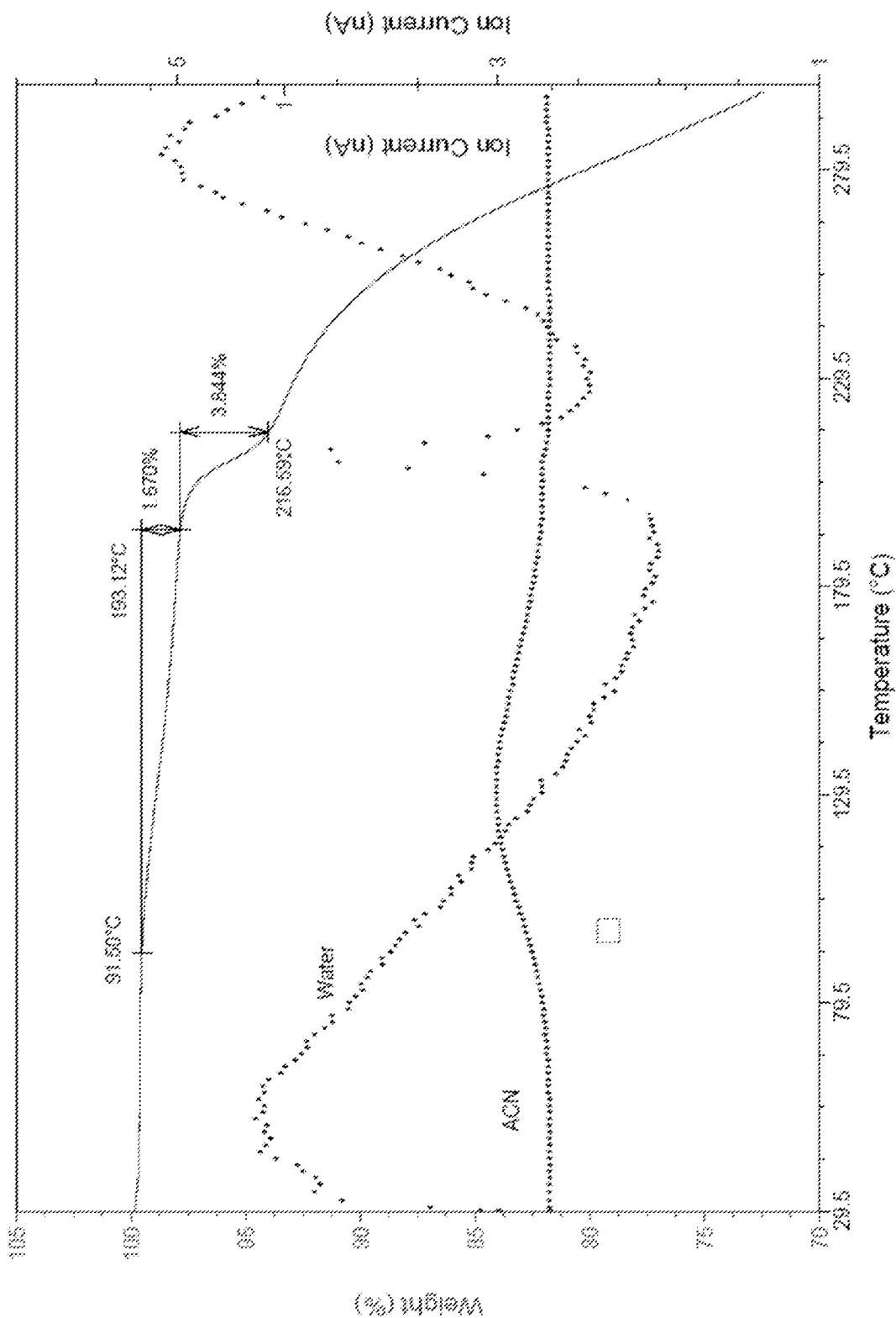
FIG. 16—TGA-MS of mesylate salt of Example 80

For the hydrochloride candidate, DSC of hydrochloride candidate shows one typical endothermic peak at 164.0° C. (FIG. 12). TGA-MS profile showed weight loss of ~6.5% from 118.4° C. to 196.4° C. (FIG. 16), which was probably caused by water. Hydrochloride candidate could be classified as slightly hygroscopic (1.59% weight gain from 0 to 80% RH) according to DVS result (FIG. 17). No form transformation was observed after DVS test (FIG. 13). The molar ratio of chloride ion to free base of the hydrochloride candidate is 0.98:1 based on ELSD results (Table 2).

Figure 15:
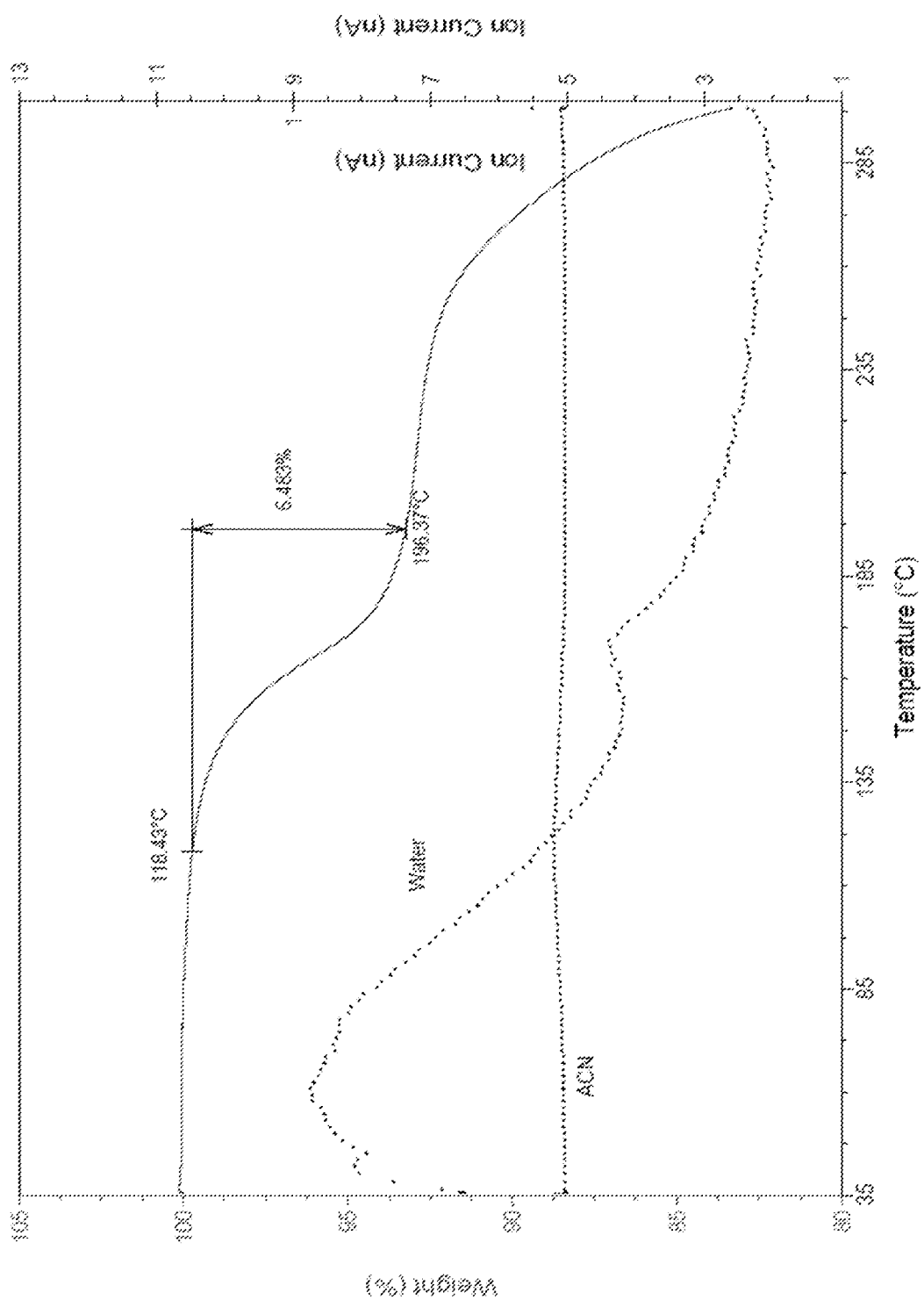
FIG. 15—TGA-MS of hydrochloride salt of Example 80.

For the mesylate candidate the TGA profile showed weight loss of ~1.7% from 91.5° C. to 193.1° C. and 3.8% from 93.1 to 216.6° C. (FIG. 18). The mesylate candidate decomposed at ~190° C., and no obvious melting peak was found by DSC. The mesylate candidate could be classified as hygroscopic (2.47% weight gain from 0 to 80% RH) according to DVS result (FIG. 19). No form transformation was observed after DVS test (FIG. 15).

TABLE 2

Salt Experiment Results of Example 80

| No. | Acids | XRPD Pattern | DSC 1st peak (° C.)/ΔH (J/g) | Solid | TGA (wt. % loss) | DVS Sorption (%) | Molar ratio (ion:free base) |
|---|---|---|---|---|---|---|---|
| 1 | Free Base | I | 178.2/89.36 (mp*[1]) | — | 0.03 (171.5-182.9° C.) | 0.16 | — |
| 2 | CH$_3$SO$_3$H (1:1) | II | No melting peak observed | Light Yellow | 1.67 (91.5-193.1° C.) 3.84 (193.1-216.6° C.) | 2.47 | 1:1 |
| 3 | HCl (1:1) | III | 164.0/211.2 (mp*[1]) | White | 6.48 (118.4-196.4° C.) | 1.59 | 0.98:1 |
| 4 | H$_2$SO$_4$ (1:1) | Amorphous | — | White | — | — | — |
| 5 | H$_2$SO$_4$ (2:1) | Amorphous | — | Yellow | — | — | — |
| 6 | p-toluene sulfonic acid (1:1) | Amorphous | — | Light Yellow | — | — | — |

*[1]mp means the form showed a clear melting point

Instrument Parameters
X-Ray Powder Diffractometer (XRPD)
  Samples were run on XRPD (D8 Advance, Bruker) using the following method: Tube: Cu: K-Alpha (λ=1.54179Å). Generator: Voltage: 40 kV; Current: 40 mA. Scan Scope: 4 to 40 deg; Sample rotation speed: 15 rpm. Scanning rate: 10 deg./min.
Differential Scanning Calorimetry (DSC) Methods
  The DSC (Q2000, TA) method used the following conditions: Heat from 25° C. to 250° C. (300° C.) at 10° C./min
Thermal Gravimetric Analysis (TGA) Methods
  The TGA (Q5000IR, TA) method used the following conditions: Heat from RT to 320° C. at 10° C./min.
Polarized Light Microscope (PLM)
  The polarized light microscope method used the following equipment: Nikon LV100POL equipped with 5 mega-pixel CCD; Physical Lens: 20×/50×.
Dynamic Vapor Sorption (DVS)
  Transfer about 10 mg of sample into a DVS (DVS Advantage-1, SMS) and record the weight change with respect to the atmospheric humidity at 25° C. Use the following parameters: Equilibrium: dm/dt: 0.01%/min. (for min: 10 min and max: 180 min). Drying: 0% RH for 120 min RH (%) measurement step: 10%; RH (%) measurement step scope: 0-90-0%

TABLE 4

Criteria for hygroscopicity evaluation

| Hygroscopicity Classification | Water Sorption Criterion* |
|---|---|
| Deliquescent | Sufficient water is absorbed to form a |
| Very hygroscopic | ΔW % ≥ 15% |
| Hygroscopic | 15% > ΔW % ≥ 2% |
| Slightly hygroscopic | 2% > ΔW % ≥ 0.2% |
| Non-hygroscopic | ΔW % < 0.2% |

*At 25 ± 1° C. and 80 ± 2% RH (European Pharmacopoeia 6.0)

Figure 10:
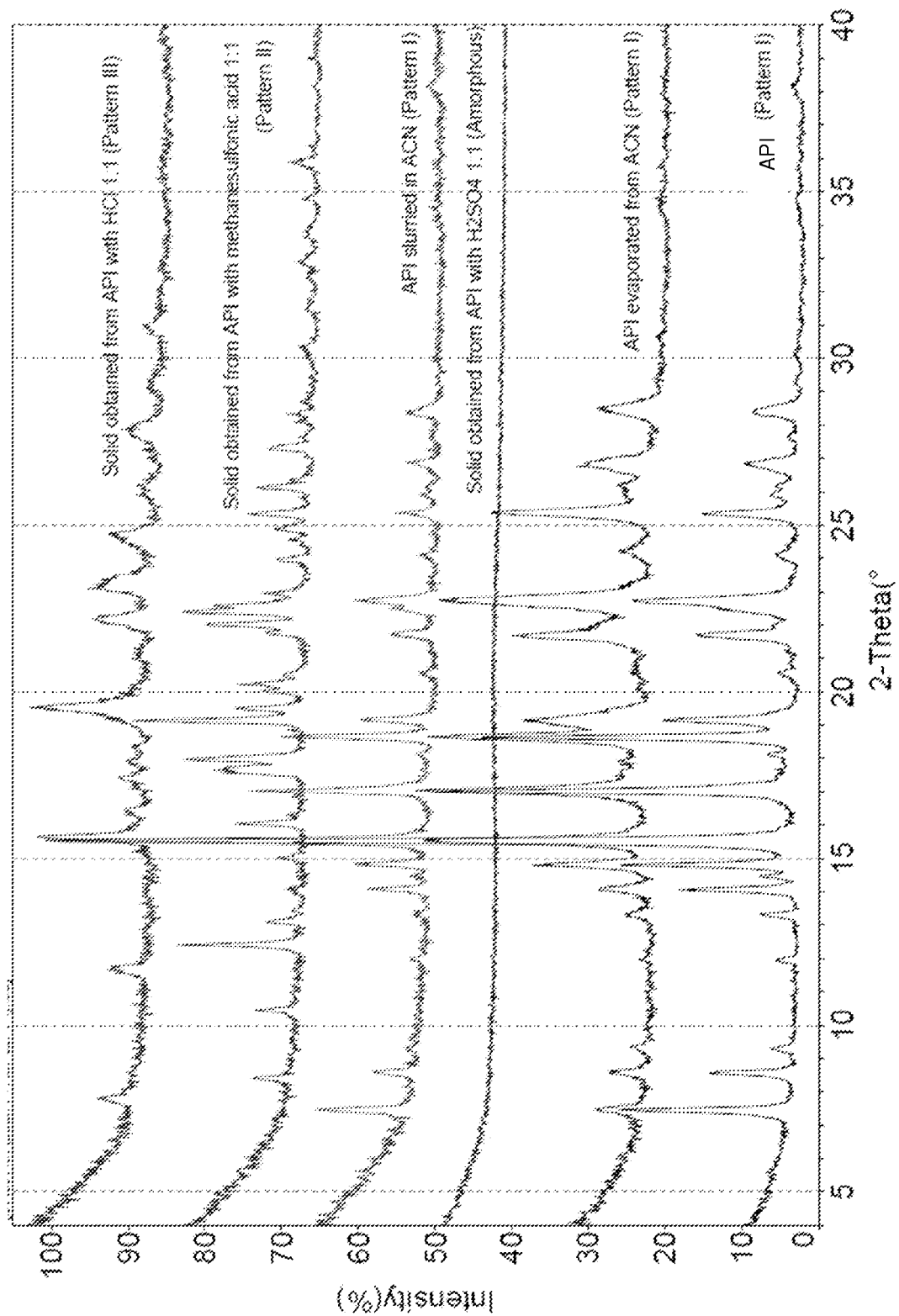
FIG. 10—XRPD overlay of the solids obtained from salt preparations.

Assays
PK Analysis
  Pharmacokinetic studies were performed in female CD-1 nude mice. —Either 10 or 50 mg/kg of each test article was administered PO, QD in 0.5% methylcellulose aqueous solution or suspension. The compound 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole free base was designated Group A; 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole trifluoroacetic acid salt was designated Group B; and 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole mesylate salt was designated Group C. Plasma concentrations were analyzed using a LC/MS method and the pharmacokinetic parameters computed using a noncompartmental method. Results are given below in the following Tables (wherein BQL indicated the value was below the limit of quantitation, SD is the standard deviation, and CV % is the coefficient of variation) and in FIG. 10. In CD-1 mice, plasma concentrations of 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole 2,2,2-trifluoroacetate and 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole methanesulfonate and 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole besylate salt and 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole hydrochloride were significantly higher than that of the free base, 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole. It is expected that other compounds of the Formulas disclosed herein would have advantageous pharmacokinetic properties.

TABLE 5

Plasma Concentration in Female CD-1 Nude Mice

| Formulation Group | Sample ID | Time point (h) | Calc. Conc. (ng/mL) | Calc. Conc. (nM) | Mean (nM) | SD | CV (%) |
|---|---|---|---|---|---|---|---|
| A | 1 | 2 | 160.4 | 285.4 | 561.2 | 179.6 | 32.0 |
| A | 2 | 2 | 369.5 | 657.3 | | | |
| A | 3 | 2 | 428.2 | 761.7 | | | |
| A | 4 | 2 | 332.7 | 591.7 | | | |
| A | 5 | 2 | 286.7 | 510.0 | | | |
| B | 6 | 2 | 636.4 | 1131.9 | 834.8 | 186.9 | 22.4 |

TABLE 5-continued

Plasma Concentration in Female CD-1 Nude Mice

| Formulation Group | Sample ID | Time point (h) | Calc. Conc. (ng/mL) | Calc. Conc. (nM) | Mean (nM) | SD | CV (%) |
|---|---|---|---|---|---|---|---|
| B | 7 | 2 | 420.5 | 748.0 | | | |
| B | 8 | 2 | 446.2 | 793.6 | | | |
| B | 9 | 2 | 355.4 | 632.1 | | | |
| B | 10 | 2 | 488.1 | 868.2 | | | |
| C | 11 | 2 | 1504.5 | 2676.0 | 2249.9 | 511.6 | 22.7 |
| C | 12 | 2 | 819.5 | 1457.7 | | | |
| C | 13 | 2 | 1532.2 | 2725.3 | | | |
| C | 14 | 2 | 1264.1 | 2248.5 | | | |
| C | 15 | 2 | 1204.2 | 2141.9 | | | |
| A | 1 | 24 | 555.0 | 987.2 | 414.3 | 325.2 | 78.5 |
| A | 2 | 24 | 172.7 | 307.2 | | | |
| A | 3 | 24 | 192.7 | 342.7 | | | |
| A | 4 | 24 | 131.2 | 233.3 | | | |
| A | 5 | 24 | 113.1 | 201.3 | | | |
| B | 6 | 24 | 802.0 | 1426.5 | 776.4 | 487.5 | 62.8 |
| B | 7 | 24 | 124.1 | 220.7 | | | |
| B | 8 | 24 | 627.5 | 1116.1 | | | |
| B | 9 | 24 | 275.6 | 490.3 | | | |
| B | 10 | 24 | 353.2 | 628.2 | | | |
| C | 1 | 8 h | 1636.8 | 2911.4 | N/A | N/A | N/A |
| C | 3 | 6 h | 1659.5 | 2951.8 | | | |
| C | 12 | <24 | 826.3 | 1469.8 | | | |

TABLE 6

Group 1, Individual and mean plasma concentration-time data of 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole FREE BASE after a PO dose of 10 mg/kg in fed female CD1 nude mice

| Sampling time (hr.) | Concentration (μM) Individual | | | Mean (μM) | SD | CV (%) |
|---|---|---|---|---|---|---|
| 0 | BQL | BQL | BQL | BQL | NA | NA |
| 0.083 | 0.02403 | 0.0121 | 0.0181 | 0.0181 | 0.00599 | 33.1 |
| 0.25 | 0.0865 | 0.0853 | 0.0795 | 0.0837 | 0.00375 | 4.48 |
| 0.5 | 0.230 | 0.419 | 0.218 | 0.289 | 0.113 | 39.0 |
| 1 | 0.477 | 0.542 | 0.531 | 0.516 | 0.0346 | 6.70 |
| 2 | 0.670 | 0.490 | 0.666 | 0.609 | 0.103 | 16.9 |
| 4 | 0.596 | 0.713 | 0.499 | 0.603 | 0.107 | 17.8 |
| 8 | 0.624 | 0.478 | 0.599 | 0.567 | 0.0784 | 13.8 |
| 24 | 0.0991 | 0.0697 | 0.0974 | 0.0888 | 0.0165 | 18.6 |

| PK parameters | Unit | Estimated Value |
|---|---|---|
| $T_{max}$ | hr. | 2.00 |
| $C_{max}$ | μM | 0.609 |
| Terminal $t_{1/2}$ | hr. | 6.83 |
| $AUC_{last}$ | hr. * μM | 9.61 |
| $AUC_{INF}$ | hr. * μM | 10.5 |

TABLE 7

Group 2, Individual and mean plasma concentration-time data of 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole FREE BASE after a PO dose of 10 mg/kg in fasted female CD1 nude mice

| Sampling time (hr.) | Concentration (μM) Individual | | | Mean (μM) | SD | CV (%) |
|---|---|---|---|---|---|---|
| 0 | BQL | BQL | BQL | BQL | NA | NA |
| 0.083 | 0.03472 | 0.0272 | 0.0248 | 0.0289 | 0.00516 | 17.9 |
| 0.25 | 0.216 | 0.315 | 0.309 | 0.280 | 0.0556 | 19.8 |
| 0.5 | 0.462 | 0.357 | 0.501 | 0.440 | 0.0741 | 16.9 |
| 1 | 0.780 | 0.542 | 0.328 | 0.550 | 0.226 | 41.1 |
| 2 | 1.03 | 0.761 | 1.09 | 0.959 | 0.174 | 18.1 |
| 4 | 0.646 | 0.608 | 0.704 | 0.652 | 0.0488 | 7.47 |
| 8 | 0.864 | 0.460 | 0.558 | 0.627 | 0.211 | 33.6 |
| 24 | 0.324 | 0.155 | 0.199 | 0.226 | 0.088 | 38.7 |

| PK parameters | Unit | Estimated Value |
|---|---|---|
| $T_{max}$ | hr. | 2.00 |
| $C_{max}$ | μM | 0.959 |
| Terminal $t_{1/2}$ | hr. | 12.4 |
| $AUC_{last}$ | hr. * μM | 12.1 |
| $AUC_{INF}$ | hr. * μM | 16.2 |

TABLE 8

Group 3, Individual and mean plasma concentration-time data of 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole MESYLATE SALT after a PO dose of 10 mg/kg in female CD1 nude mice

| Sampling time (hr.) | Concentration (μM) Individual | | | Mean (μM) | SD | CV (%) |
|---|---|---|---|---|---|---|
| 0 | BQL | BQL | BQL | BQL | NA | NA |
| 0.083 | 0.0257 | 0.0222 | 0.0419 | 0.0299 | 0.0105 | 35.1 |
| 0.25 | 0.359 | 0.755 | 0.619 | 0.578 | 0.201 | 34.8 |
| 0.5 | 0.624 | 1.34 | 1.10 | 1.02 | 0.365 | 35.7 |
| 1 | 0.955 | 1.09 | 1.34 | 1.13 | 0.193 | 17.1 |
| 2 | 1.48 | 2.07 | 2.28 | 1.94 | 0.415 | 21.3 |
| 4 | 1.10 | 1.10 | 1.32 | 1.17 | 0.130 | 11.1 |
| 8 | 0.788 | 0.784 | 1.23 | 0.934 | 0.256 | 27.4 |
| 24 | 0.396 | 0.287 | 0.349 | 0.344 | 0.0544 | 15.8 |

| PK parameters | Unit | Estimated Value |
|---|---|---|
| $T_{max}$ | hr. | 2.00 |
| $C_{max}$ | μM | 1.94 |
| Terminal $t_{1/2}$ | hr. | 11.2 |
| $AUC_{last}$ | hr. * μM | 19.9 |
| $AUC_{INF}$ | hr. * μM | 25.5 |

TABLE 9

Group 4, Individual and mean plasma concentration-time data of 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole BESYLATE SALT after a PO dose of 10 mg/kg in female CD1 nude mice

| Sampling time (hr.) | Concentration (μM) Individual | | | Mean (μM) | SD | CV (%) |
|---|---|---|---|---|---|---|
| 0 | BQL | BQL | BQL | BQL | NA | NA |
| 0.083 | 0.00724 | 0.00741 | 0.00527 | 0.00664 | 0.00119 | 17.9 |
| 0.25 | 0.104 | 0.159 | 0.147 | 0.137 | 0.0292 | 21.4 |
| 0.5 | 0.877 | 0.849 | 0.660 | 0.795 | 0.118 | 14.8 |
| 1 | 0.591 | 0.849 | 0.683 | 0.708 | 0.131 | 18.5 |
| 2 | 0.599 | 0.947 | 0.871 | 0.805 | 0.183 | 22.7 |
| 4 | 1.02 | 1.03 | 1.09 | 1.05 | 0.0397 | 3.79 |
| 8 | 0.436 | 0.586 | 0.522 | 0.515 | 0.0749 | 14.6 |
| 24 | 0.222 | 0.185 | 0.245 | 0.217 | 0.0306 | 14.1 |

TABLE 9-continued

Group 4, Individual and mean plasma concentration-time data of
5-(5-methyl-1-(3-(4-(methylsulfonyl)piperidin-1-yl)benzyl)-1H-
1,2,4-triazol-3-yl)-3-(4-(trifluoromethoxy)phenyl)-1,2,4-
oxadiazole BESYLATE SALT after a PO dose of 10 mg/kg
in female CD1 nude mice

| PK parameters | Unit | Estimated Value |
|---|---|---|
| $T_{max}$ | hr. | 4.00 |
| $C_{max}$ | µM | 1.05 |
| Terminal $t_{1/2}$ | hr. | 9.69 |
| $AUC_{last}$ | hr. * µM | 12.1 |
| $AUC_{INF}$ | hr. * µM | 15.1 |

TABLE 10

Group 5, Individual and mean plasma concentration-time data of
5-(5-methyl-1-(3-(4-(methylsulfonyl)piperidin-1-yl)benzyl)-1H-
1,2,4-triazol-3-yl)-3-(4-(trifluoromethoxy)phenyl)-1,2,4-
oxadiazole HYDROCHLORIDE SALT after a PO dose of
10 mg/kg in female CD1 nude mice

| Sampling time (hr.) | Concentration (µM) Individual | | | | Mean (µM) | SD | CV (%) |
|---|---|---|---|---|---|---|---|
| 0 | BQL | BQL | BQL | BQL | BQL | NA | NA |
| 0.083 | 0.821 | 0.242 | 0.258 | 0.440 | 0.330 | 74.9 |
| 0.25 | 4.76 | 1.43 | 3.25 | 3.15 | 1.66 | 52.9 |
| 0.5 | 5.95 | 4.07 | 2.62 | 4.21 | 1.67 | 39.7 |
| 1 | 6.65 | 3.44 | 5.87 | 5.32 | 1.67 | 31.4 |
| 2 | 5.88 | 1.72 | 3.02 | 3.54 | 2.13 | 60.1 |
| 4 | 4.30 | 4.06 | 2.74 | 3.70 | 0.839 | 22.7 |
| 8 | 2.15 | 4.03 | 1.67 | 2.61 | 1.25 | 47.7 |
| 24 | 0.553 | 0.541 | 0.503 | 0.532 | 0.0257 | 4.83 |

| PK parameters | Unit | Estimated Value |
|---|---|---|
| $T_{max}$ | hr. | 1.00 |
| $C_{max}$ | µM | 5.32 |
| Terminal $t_{1/2}$ | hr. | 7.09 |
| $AUC_{last}$ | hr. * µM | 53.1 |
| $AUC_{INF}$ | hr. * µM | 58.5 |

Cell-Based Reporter Assay for $IC_{50}$ Determinations

293T-HRE-GFP-luc cells were routinely maintained in DMEM media (high glucose version with GlutaMAX and HEPES, Gibco, catalog #10564) supplemented with 10% fetal bovine serum and 2 µg/mL puromycin (Invitrogen, catalog #A11138-03) using a humidified incubator (normoxic conditions consisting of 37° C., 5% $CO_2$ and ambient $O_2$).

In preparation for the reporter assay, cells were harvested and resuspended in DMEM media (high glucose version with GlutaMAX and HEPES) supplemented with 10% fetal bovine serum. Cells were inoculated into 384-well white Culturplates (Perkin Elmer catalog #6007680) at a density of 12,000 cells/well in a volume of 30 µL. The microplates were incubated overnight (approximately 17-19 hours) at 37° C. with 5% $CO_2$ and ambient 02. Stock solutions of the test compounds were prepared in DMSO (Sigma, Catalog #D2650) and serially diluted 1:3 using DMSO. Compounds were additionally diluted (1:50) with culture medium and 10 µL were added per well to the Culturplate. Following a 30 min. incubation under normoxic conditions, the plates were incubated in hypoxia for 6 hrs. (37° C., 5% $CO_2$ and 1% $O_2$). Steadylite Plus (Perkin Elmer, catalog #6016751) was then added (40 µL/well), the plates were mixed on an orbital shaker at room temperature in the dark for 15 min., and luminescence was measured using an Envision plate reader (Perkin Elmer). $IC_{50}$ values were calculated using a four-parameter logistic curve fit. Results are shown below in Table 11; ND indicates no data.

TABLE 11

| Example No. | Classification: A = <100 nM B = 100-1000 nM C = 1-10 uM |
|---|---|
| 80 | A |

Diffuse Large B-Cell Lymphoma (DLBCL) Assay

Equal number of TMD8 cells were plated and treated with varying concentrations of the compound of Example 80 for 7 days. Percent of viable cells was determined using Guava ViaCount reagents (EMD Millipore cat #4000-0040) that contains proprietary dyes that enable the determination of the number of live and dead cells in a sample (FIG. 1). TMD8 cells respond robustly to the compound of Example 80, indicating the effectiveness of the compound as an anti-tumor agent in DLBCL.

Acute Myeloid Leukemia

Figure 6:
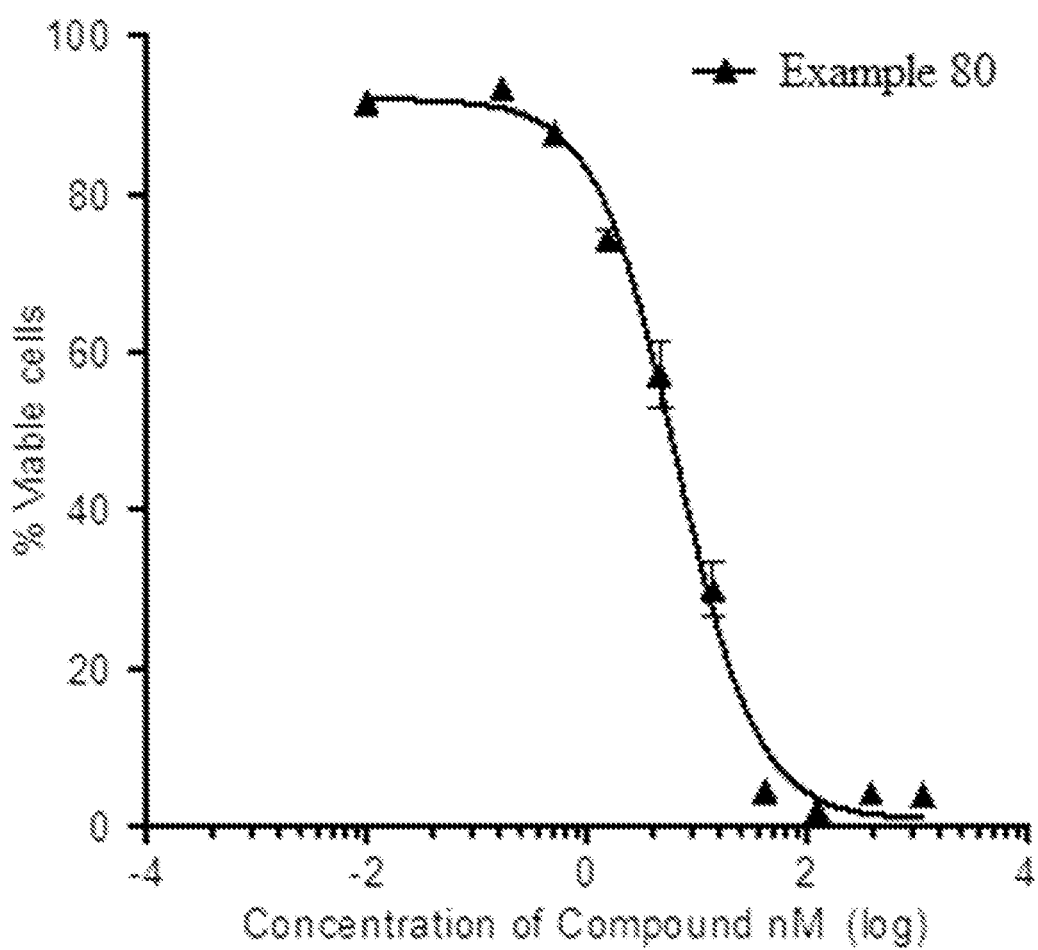
FIG. 6—Compounds of this disclosure inhibit the growth of leukemia OCI-AML3 cells as shown by reduced number of viable cells following treatment with Example 80.
Figure 7:
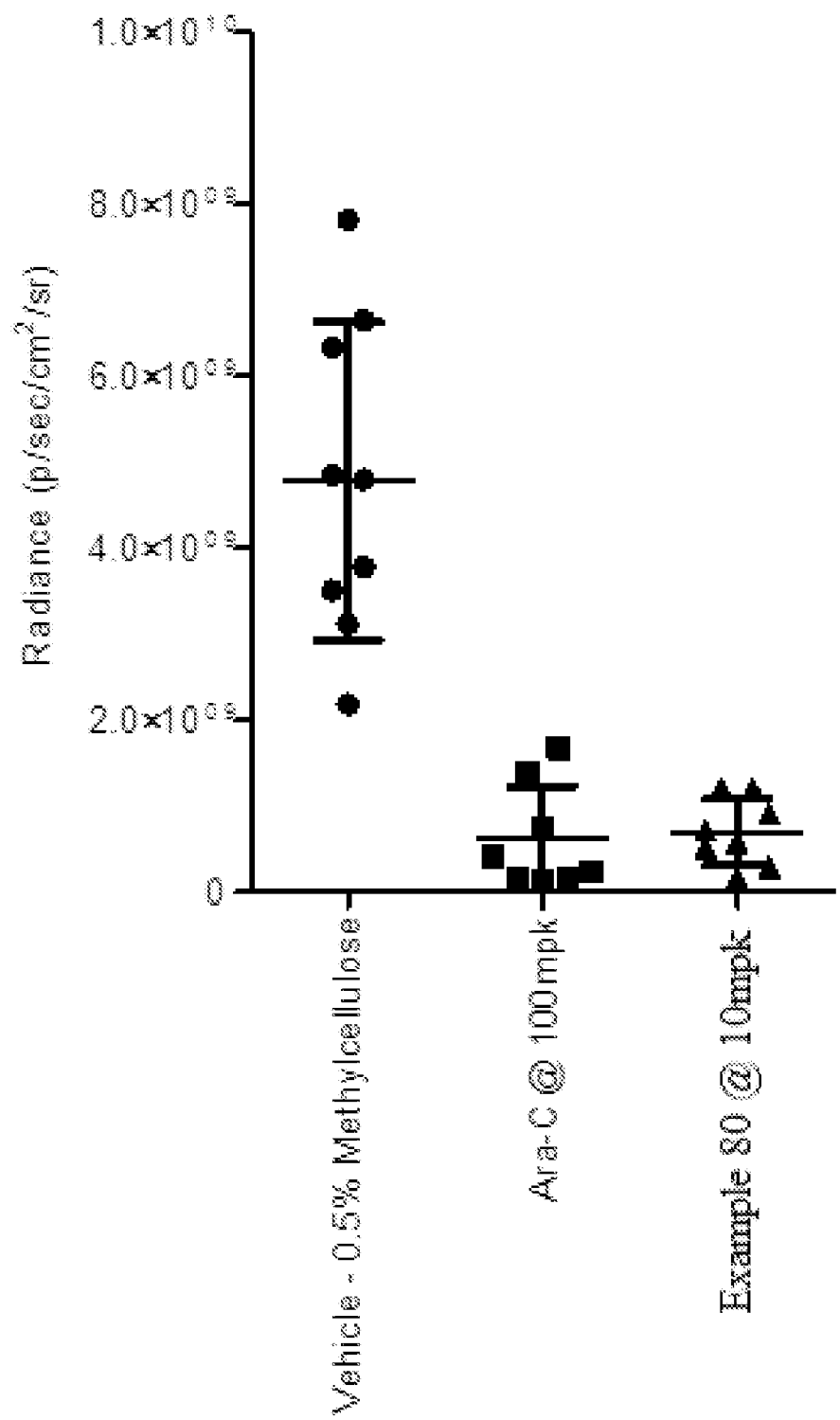
FIG. 7—Compounds of this disclosure reduce disease burden in human leukemia model, daily oral treatment with 10 mg/kg of Example 80 reduces disease burden in OCI-AML3 models in NSG mice as measured by IVIS imaging.
Figure 8:
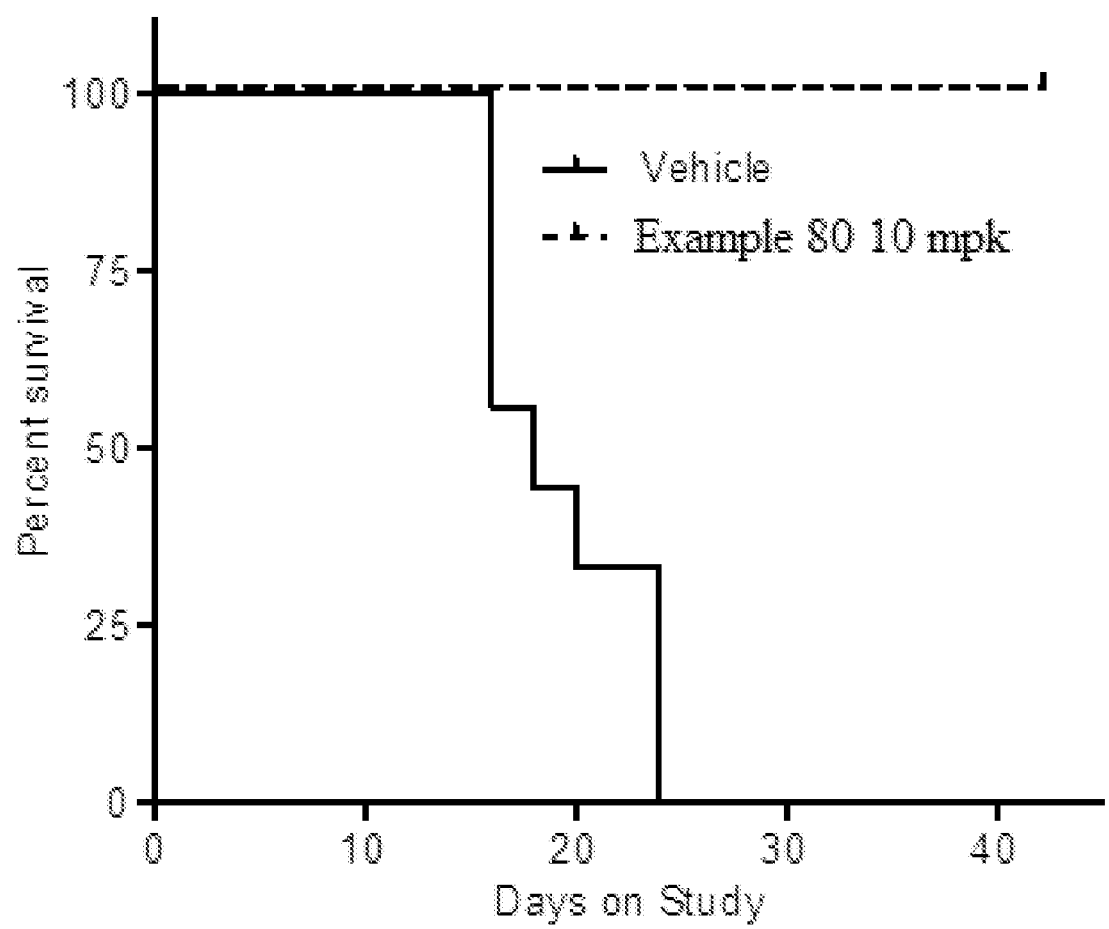
FIG. 8—Compounds of this disclosure prolong the survival in human leukemia model, daily oral treatment with 10 mg/kg of Example 80 extends survival in OCI-AML3 models in NSG mice.
Figure 9:
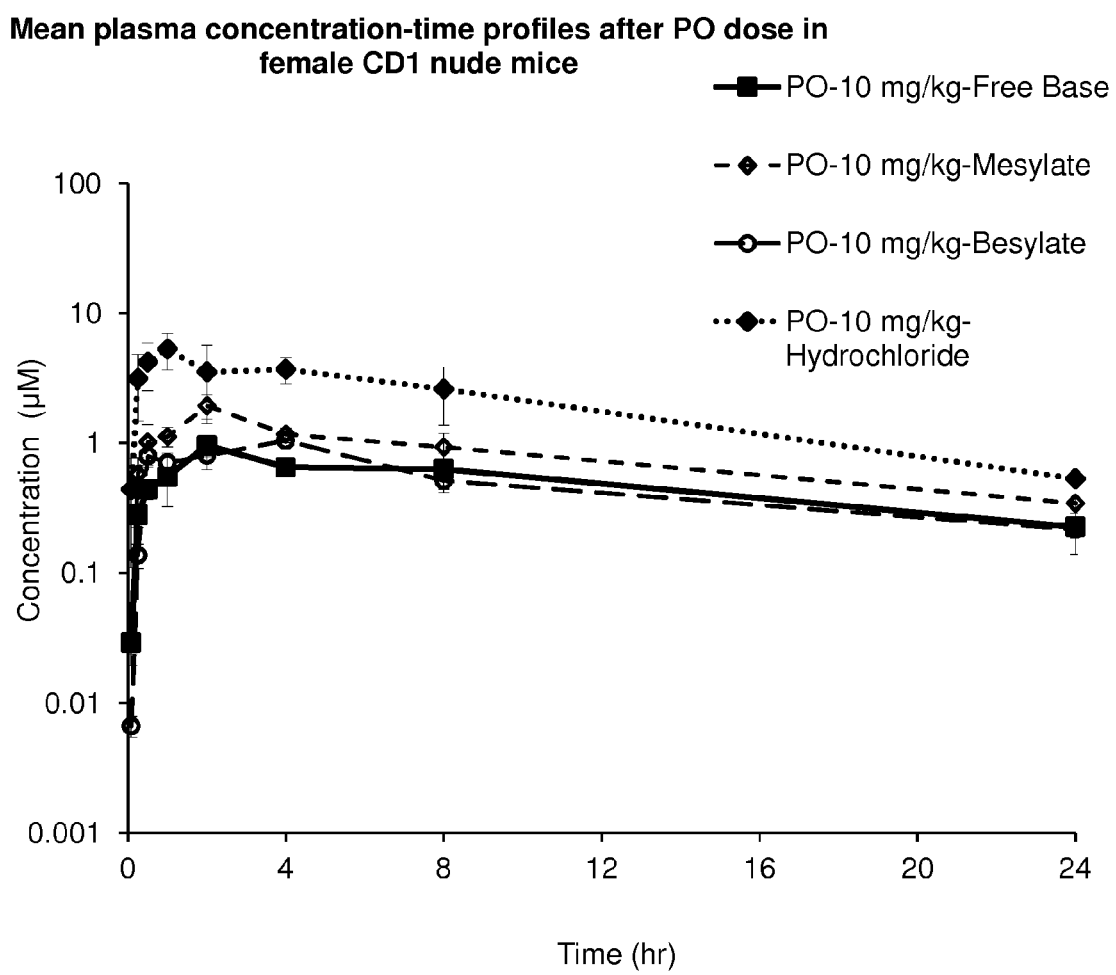
FIG. 9—Mesylate, besylate, and hydrochloride salts of 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole show improved oral bioavailability in comparison to the free base.

The OCI-AML3 cell line was treated with various concentrations of compound for 2 days and the percent of viable cells normalized to control cells treated with DMSO (FIG. 6). OCI-AML3 cells constitutively expressing luciferase were tail vein injected in NSG nude mice. 17 days after cell injection, luciferin was injected into animals and luciferase signal was measured using an IVIS imaging system to determine tumor burden and for randomization of subjects into study groups. On day 18, animals began receiving daily oral doses of vehicle or 10 mpk of the compound of Example 80 which continued throughout the study. On day 28, imaging was performed again to determine tumor burden (FIG. 7). Treatment of tumor cell bearing animals with the compound of Example 80 significantly increased their survival relative to vehicle treated animals (FIG. 8).

Neuroblastoma and Glioblastoma Cellular Assay and Xenograft Model

Figure 2:
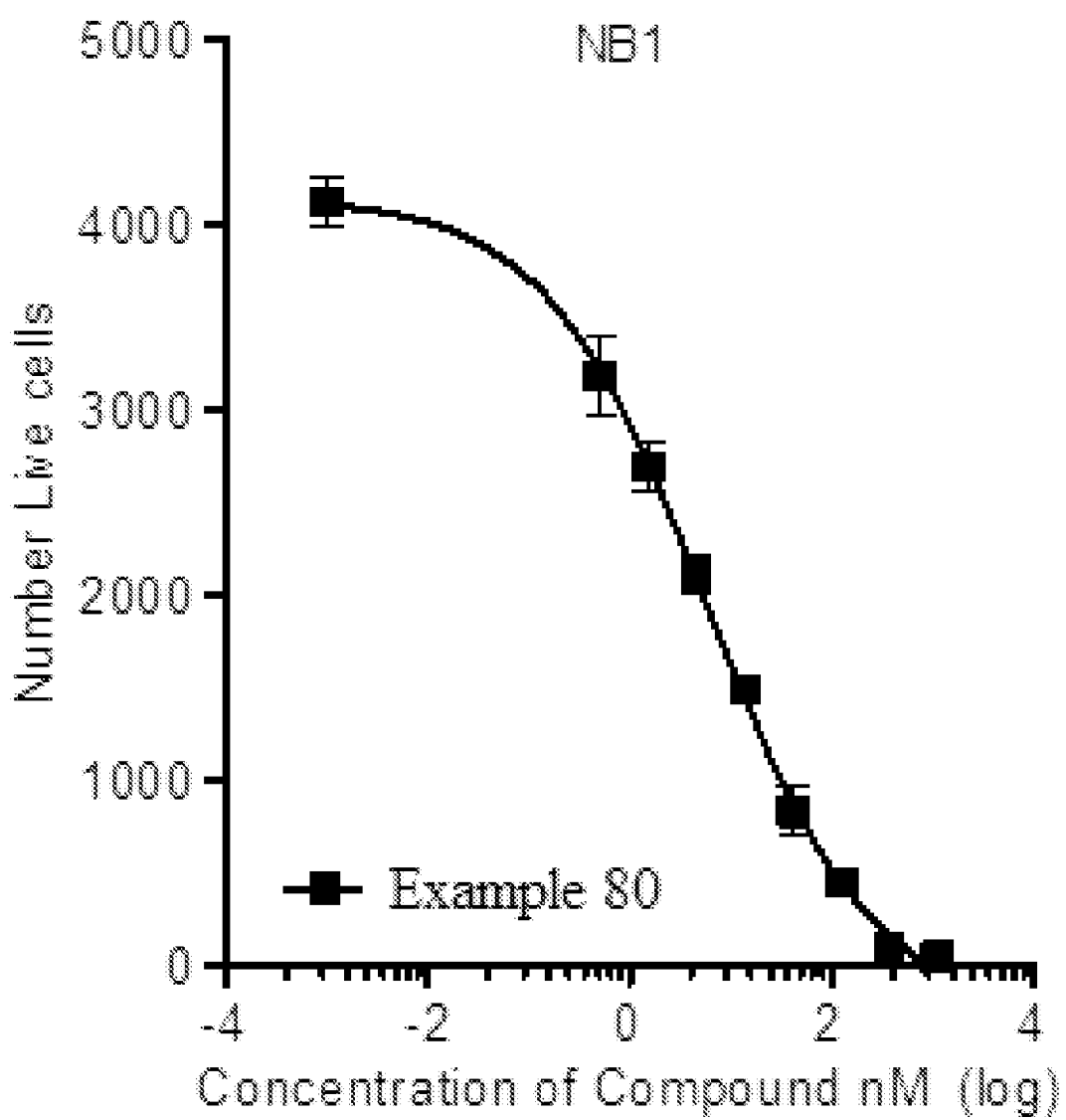
FIG. 2—Compounds of this disclosure inhibit the growth of neuroblastoma NB-1 cells as shown by reduced number of viable cells following treatment with Example 80.
Figure 3:
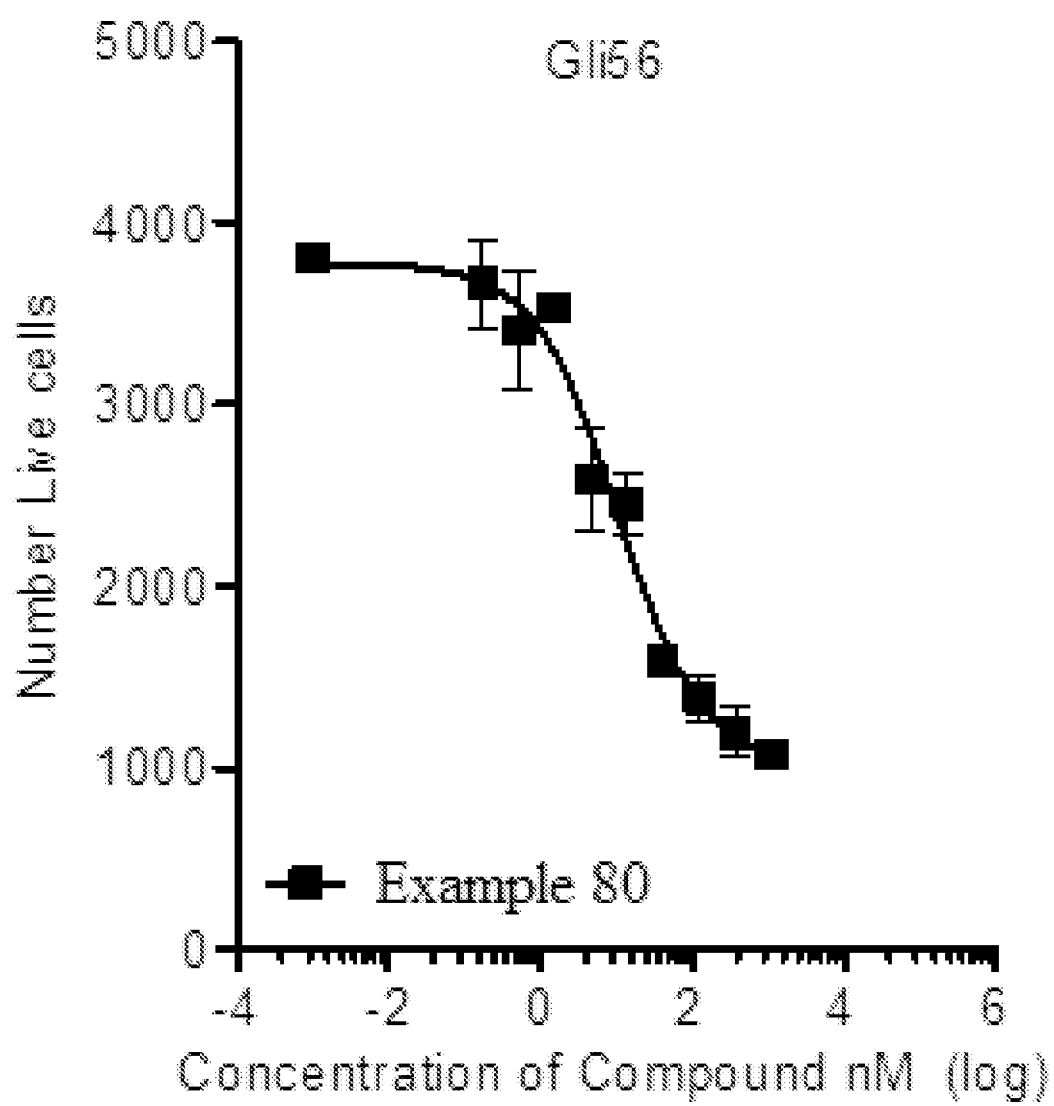
FIG. 3—Compounds of this disclosure inhibit the growth of glioblastoma Gli56 cells as shown by reduced number of viable cells following treatment with Example 80.
Figure 4:
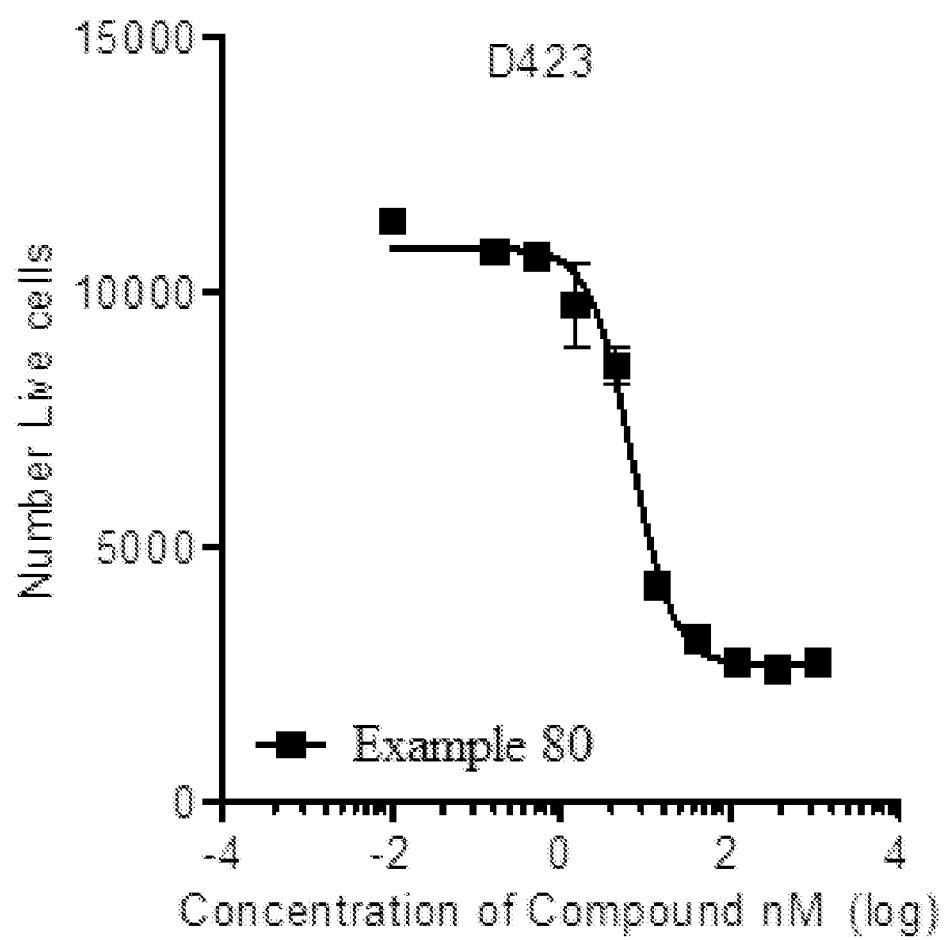
FIG. 4—Compounds of this disclosure inhibit the growth of glioblastoma D423 cells as shown by reduced number of viable cells following treatment with Example 80.

Cellular Assays:

NB-1, Gli56, and D423 cell lines are deleted for ENO-1 (GLI56 and D423) or PGD, which renders them with reduced glycolytic capacity (Muller, F. et al., Nature, 2012, 488, 337-42). When these cell lines are treated with various concentrations of Example 80, cell numbers are significantly reduced with cell death readily apparent in NB-1 and Gli56 (FIG. 2-4).

Figure 5:
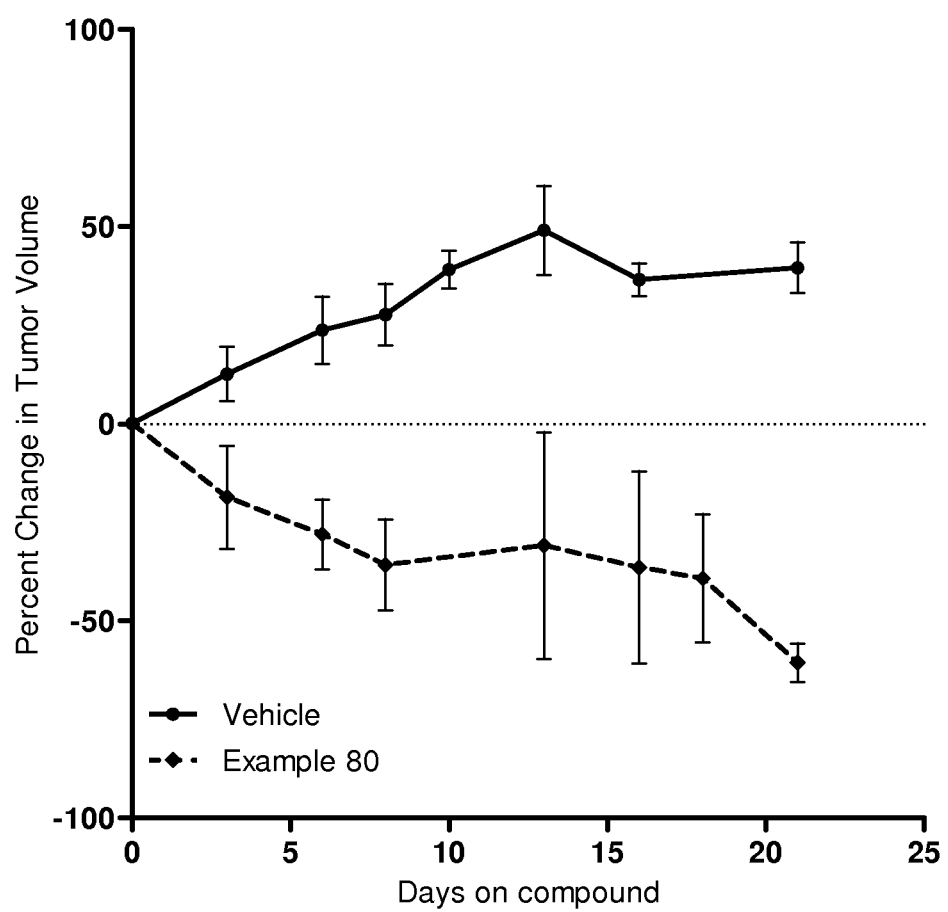
FIG. 5—Compounds of this disclosure inhibit the growth of NB-1 xenografts in vivo, daily oral treatment with 10 mg/kg of Example 80 reduces the tumor growth.

Xenograft Model:

To establish activity and provide in vivo proof of concept, NB-1 cells were implanted into CD-1 nude mice and treated with 40 mpk of the compound of Example 80 po or vehicle daily when tumors reached 400-500 mm³. Tumor size was measured 3x/week using caliper measurements (FIG. 5).

In Vivo Murine Xenograft Models for Tumor Growth Inhibition

The compounds disclosed herein have been evaluated in vivo and shown to inhibit the growth of human cancer xenografts in nude mice.

Non-Small Cell Lung Cancer:

$H_{460}$ cells may be implanted subcutaneously in CD-1 nude mice and treated with 150 mpk qdx14 PO of a compound disclosed herein delivered by oral gavage for 14 days. Animals are randomized into study groups and the study initiated when the average tumor volume is 400 mm³. During treatment, tumor volume is measured three times per week to determine tumor growth over the course of the study. On day 15, 3 hours prior to take down, hypoxyprobe (Hypoxyprobe, Inc. cat # HP3) is injected into mice. Tumor sections are stained (dark areas) for the level of hypoxia utilizing an anti-hypoxyprobe antibody and standard IHC methods. The same tumors are stained for the expression of HIF regulated gene carbonic anhydrase IX (CA9) using standard IHC methods. Treatment of the mice with a free base of a compound disclosed herein has been shown to inhibit the growth of the H460 xenografts over the course of the study, establishing the anti-tumor activity of the compound like those described herein. Target engagement, as measured by elimination of hypoxia and CA9 protein expression in the tumor, was achieved establishing that at the anti-tumor activity level, the compound is inhibiting HIF pathway activity. It is expected that the compounds disclosed herein will be similarly efficacious and in some cases more efficacious.

Head and Neck Cancer:

In one example of an in vivo study, HN5 head and neck cells are injected intramuscularly into CD-1 nude mice. Upon tumors reaching 8.5 mm in diameter, animals are enrolled in the study and received either vehicle or test compound with or without a 4 Gy dose 6 hours after test compound on days 1-5 of the study. Tumor size is measured every other day to determine the rate of growth.

Further examples of xenograft models are given below for glioblastoma cancer.

Glioblastoma Cancer.

In one example of a typical protocol, female athymic nu/nu nude mice, 5 to 6 weeks-old (approx. 18-22 g) may be obtained, for example from Harland Sprague-Dawley, Inc. Nude mice are inoculated with tumor cells. U251, U87-EGFRviii or other human cancer cells, at a concentration of about 1-5×10⁶ in 0.15 ml solution mixed with matrigel and DMEM medium are injected subcutaneously into the right flank of each mouse. When tumor volume reaches around 200 or 600 mm³, animal are randomly assigned to three groups (or more, depending on the number of dose levels of a compound to be evaluated) and treatment started with test article (for example, at 5 mg/kg/day or 10 mg/kg/day) delivered via oral gavage for up to 21 days. Animals in control group receive the vehicle alone under identical conditions. Tumor volumes are measured by a digital caliper and calculated using the formula (L×W×H)×0.5236. Significant differences are expected to be observed compared with control group (P<0.05, using ANOVA). Animal weight is monitored throughout the experiment. It is expected that no significant difference will be observed between control and treated groups, which further indicates the test article is non-toxic in tumor-bearing nude mice at doses used for inhibiting tumor growth.

The foregoing protocols are versatile, and may be modified to substitute virtually any type of human cancer cell line. Examples include the breast cancer cell lines AG11132A, MCF-7, and T47-D; estrogen, progesterone, and HER-2/neu receptor positive breast cancer cell lines HCC-1428 and ZR-75; estrogen, progesterone, and HER-2/neu receptors negative breast cancer cell lines MDA-231 and BT20; prostate cancer cell lines LNCaP, PC-3, and DU145; colon cancer cell lines DLD-1 and LoVo; ovarian cancer cell lines OVCAR-3 and SK-OV-3; lung cancer cell lines H69AR, NCI-H23, and A549; and pancreatic cancer cell lines Capan-1 and BxPC-3. Additionally, the protocol may be altered to assay the prevention of tumor development by pre-treating with test compound. Combinations of compounds may be tested, and dosing schedules altered to deliver compound in other ways, i.e., by oral gavage, or to skip days of treatment to reduce any toxic signals. Those skilled in the art will recognize and appropriately apply the multitude of variations available.

All references, patents or applications, U.S. or foreign, cited in the application are hereby incorporated by reference as if written herein in their entireties. Where any inconsistencies arise, material literally disclosed herein controls.

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A compound of structural Formula III:

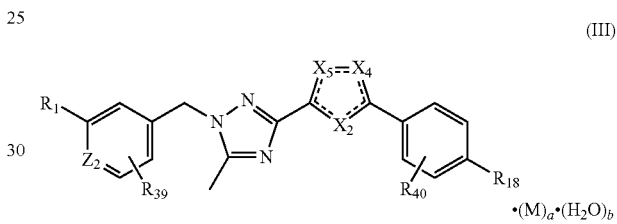

(III)

wherein:

M is selected from the group consisting of an inorganic acid and an organic acid;

with the proviso that M is not trifluoroacetic acid;

a is a fractional or whole number between about 0.5 and about 3.5 inclusive;

b is a fractional or whole number between about 0 and about 10 inclusive;

$X_2$ and $X_4$ are N and $X_5$ is O; $X_4$ and $X_5$ are N and $X_2$ is O; $X_2$ and $X_5$ are N and $X_4$ is O; $X_2$ is CH, $X_4$ is N, and $X_5$ is O; or $X_2$ is CH, $X_4$ is O, and $X_5$ is N;

$Z_2$ is selected from the group consisting of N and $CR_{14}$;

$R_1$ is selected from the group consisting of heterocycloalkyl, alkoxyalkoxy, alkylsulfonylalkoxy, heterocycloalkyloxy, heterocycloalkylcarbonyl, alkoxyalkylamido, heterocycloalkylsulfonyl, alkoxyalkylsulfonamido, wherein said heterocycloalkyl, heterocycloalkyloxy, heterocycloalkylcarbonyl, and heterocycloalkylsulfonyl is optionally substituted with one or more substituents selected from the group consisting hydrogen, alkyl, and oxo;

$R_{14}$, $R_{39}$, and $R_{40}$ are independently selected from the group consisting of hydrogen, deuterium, halogen, alkyl, haloalkyl, perhaloalkyl, cyano, hydroxy, alkoxy, haloalkoxy, perhaloalkoxy, alkylthio, amino, and saturated 3- to 7-membered cycloalkyl, any of which is optionally substituted; and $R_{18}$ is selected from the group consisting of alkyl, haloalkyl, perhaloalkyl, alkoxy, haloalkoxy, perhaloalkoxy, alkylthio, haloalkylthio, and perhaloalkylthio.

2. The compound as recited in claim 1 wherein $R_1$ is selected from the group consisting of

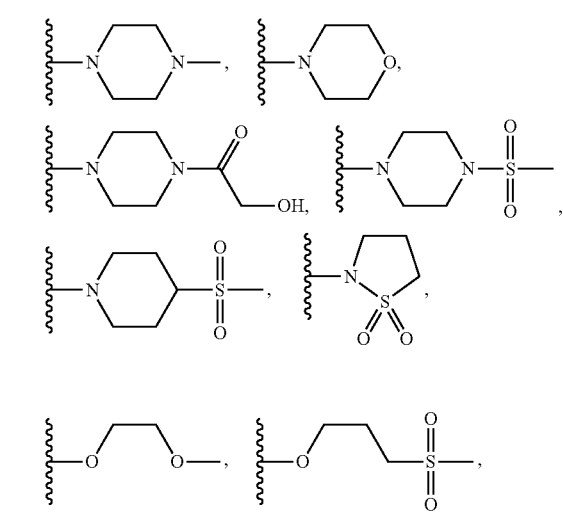

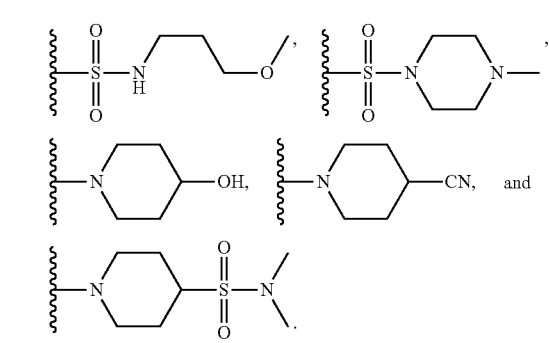

3. The compound as recited in claim 1 wherein R$_{18}$ is selected from the group consisting of isopropyl, tert-butyl, —CF$_3$, —OCF$_3$, —OCHF$_2$, and —SCF$_3$.

4. The compound as recited in claim 1 wherein:
R$_1$ is selected from the group consisting of

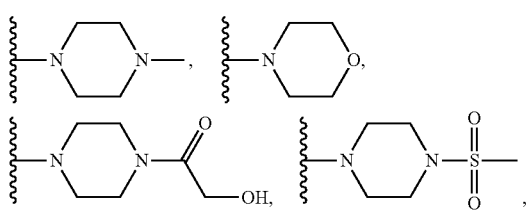

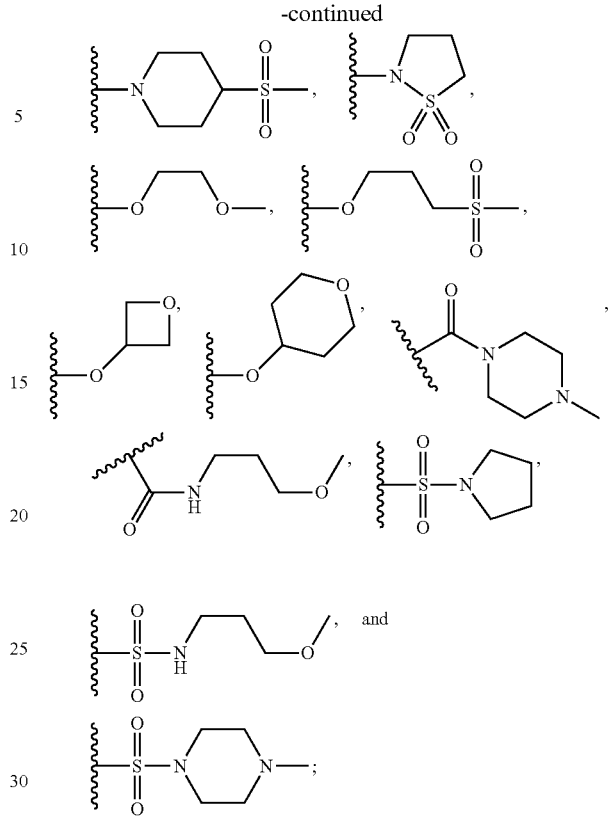

R$_{13}$, R$_{14}$, R$_{16}$, R$_{17}$, and R$_{19}$ are hydrogen; and

R$_{18}$ is selected from the group consisting of isopropyl, tert-butyl, —CF$_3$, —OCF$_3$, —OCHF$_2$, and —SCF$_3$.

5. The compound of claim 1, wherein the compound is in a solid form.

6. The compound of claim 1, wherein the compound is in a crystalline form.

7. The compound of claim 1, wherein M is selected from the group consisting of (+)-camphor-10-sulfonic acid, 2,2-dichloroacetic acid, 2-hydroxyethanesulfonic acid, acetic acid, aspartic acid, benzenesulfonic acid, citric acid, cyclamic acid, di(tert-butyl) naphthalenesulfonic acid, dodecylsulfonic acid, ethanesulfonic acid, formic acid, fumaric acid, glutamic acid, glycerophosphoric acid, glycine, hydroboric acid, hydrobromic acid, hydrochloric acid, lactic acid, maleic acid, malic acid, methanesulfonic acid, naphthalene-2-sulfonic acid, nitric acid, oxalic acid, phosphoric acid, p-toluenesulfonic acid, pyruvic acid, saccharine, succinic acid, sulfuric acid, tartaric acid, and thiocyanic acid.

8. The compound of claim 1, wherein M is selected from the group consisting of hydrochloric acid, benzenesulfonic acid, and methanesulfonic acid.

9. The compound of claim 1, wherein a equals 1 and M is hydrochloric acid.

10. The compound of claim 1, wherein a equals 1 and M is benzenesulfonic acid.

11. The compound of claim 1, wherein a equals 1 and M is methanesulfonic acid.

12. The compound of claim 1, wherein the compound has structural Formula V

V

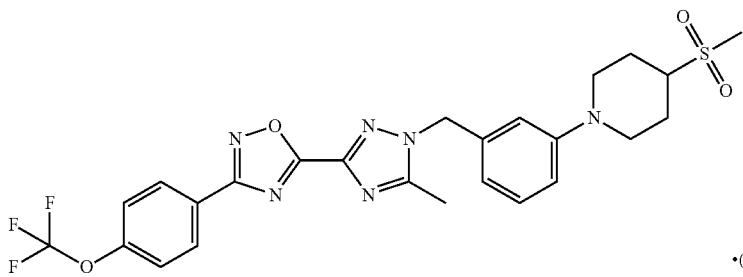

•(M)$_a$•(H$_2$O)$_b$ wherein M is selected from the group consisting of (+)-camphor-10-sulfonic acid, 2,2-dichloroacetic acid, 2-hydroxyethanesulfonic acid, acetic acid, aspartic acid, benzenesulfonic acid, citric acid, cyclamic acid, di(tert-butyl) naphthalenesulfonic acid, dodecylsulfonic acid, ethanesulfonic acid, formic acid, fumaric acid, glutamic acid, glycerophosphoric acid, glycine, hydroboric acid, hydrobromic acid, hydrochloric acid, lactic acid, maleic acid, malic acid, methanesulfonic acid, naphthalene-2-sulfonic acid, nitric acid, oxalic acid, phosphoric acid, p-toluenesulfonic acid, pyruvic acid, saccharine, succinic acid, sulfuric acid, tartaric acid, and thiocyanic acid;

a is a fractional or whole number between about 0.5 and about 3.5 inclusive; and b is a fractional or whole number between about 0 and about 5 inclusive.

13. A compound of Formula V

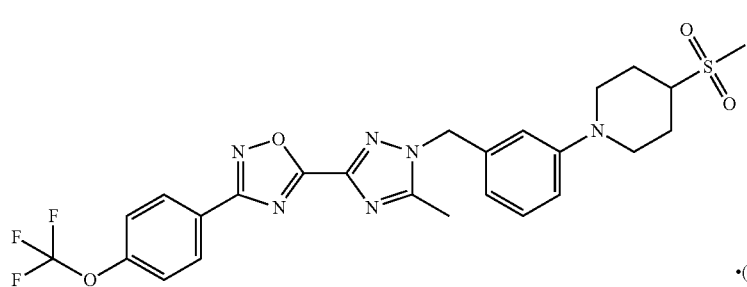

V

•(M)$_a$•(H$_2$O)$_b$ wherein M is selected from the group consisting of hydrochloric acid, di(tert-butyl) naphthalenesulfonic acid, ethanesulfonic acid, 2-hydroxyethanesulfonic acid, cyclamic acid, p-toluenesulfonic acid, thiocyanic acid, nitric acid, methanesulfonic acid, dodecylsulfonic acid, naphthalene-2-sulfonic acid, benzenesulfonic acid, oxalic acid, saccharine, 2,2-dichloroacetic acid, glycerophosphoric acid, phosphoric acid, (+)-camphor-10-sulfonic acid, sulfuric acid, maleic acid, and pyruvic acid;

a is a fractional or whole number between about 0.5 and about 3.5 inclusive; and b is a fractional or whole number between about 0 and about 5 inclusive.

14. The compound of claim 13, wherein M is chosen from hydrochloric acid, sulfuric acid, p-toluenesulfonic acid, nitric acid, methanesulfonic acid, benzenesulfonic acid, oxalic acid, and maleic acid.

15. The compound of claim 14, wherein M is chosen from hydrochloric acid, methanesulfonic acid, and benzenesulfonic acid.

16. The compound of claim 13, wherein:
a is a number between 1 and 2 inclusive; and
b is a number between 0 and about 2 inclusive.

17. The compound of claim 13, wherein a equals 1, and M is hydrochloric acid.

18. The compound of claim 13, wherein a equals 1 and M is benzenesulfonic acid.

19. The compound of claim 13, wherein a equals 1 and M is methanesulfonic acid.

20. A compound of Formula VI

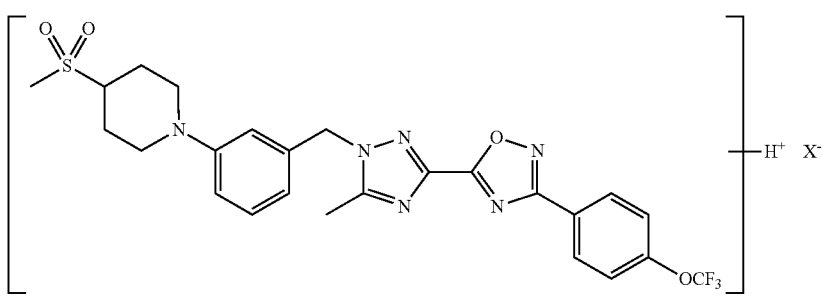

wherein X is chosen from chloride, di(tert-butyl) naphthalenesulfonate, ethanesulfonate, 2-hydroxyethanesulfonate, cyclamate, tosylate, thiocyanate, nitrate, mesylate, dodecylsulfonate, naphthalene-2-sulfonate, besylate, oxalate, saccharate, 2,2-dichloroacetate, glycerophosphorate, phosphorate, (+)-camphor-10-sulfonate, maleate, sulfate, and pyruvate.

21. The compound of claim 20, wherein X is chosen from chloride, sulfate, tosylate, nitrate, mesylate, besylate, and maleate.

22. The compound of claim 20, wherein X is chosen from chloride, mesylate, and besylate.

23. A compound selected from the group consisting of:
5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole hydrochloride;
5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole 2,2,2-trifluoroacetate;
5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole methanesulfonate; and
5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole benzenesulfonate.

24. A pharmaceutical composition comprising a compound as recited in claim 1 together with a pharmaceutically acceptable carrier.

25. The compound 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole hydrochloride.

26. A pharmaceutical composition comprising the compound as recited in claim 25 together with a pharmaceutically acceptable carrier.

27. The compound 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole methanesulfonate.

28. A pharmaceutical composition comprising the compound as recited in claim 27 together with a pharmaceutically acceptable carrier.

29. The compound 5-(5-methyl-1-(3-(4-(methylsulfonyl)piperidin-1-yl)benzyl)-1H-1,2,4-triazol-3-yl)-3-(4-(trifluoromethoxy)phenyl)-1,2,4-oxadiazole benzenesulfonate.

30. A pharmaceutical composition comprising the compound as recited in claim 29 together with a pharmaceutically acceptable carrier.

* * * * *